(12) United States Patent
Cartman et al.

(10) Patent No.: US 10,538,788 B2
(45) Date of Patent: Jan. 21, 2020

(54) METHODS, SYNTHETIC HOSTS AND REAGENTS FOR THE BIOSYNTHESIS OF DIENES AND DERIVATIVES THEREOF

(71) Applicant: INVISTA NORTH AMERICA S.A.R.L., Wilmington, DE (US)

(72) Inventors: Stephen Thomas Cartman, Eaglescliffe (GB); Alexander Brett Foster, Yarm (GB); Ana Teresa dos Santos Brito Mendes Roberts, Eaglescliffe (GB); Mark Paul Taylor, Middlesbrough (GB)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 0 days.

(21) Appl. No.: 15/717,065

(22) Filed: Sep. 27, 2017

(65) Prior Publication Data
US 2018/0094282 A1    Apr. 5, 2018

Related U.S. Application Data

(60) Provisional application No. 62/402,209, filed on Sep. 30, 2016.

(51) Int. Cl.
| | | |
|---|---|---|
| *C12N 9/88* | (2006.01) | |
| *C12P 5/00* | (2006.01) | |
| *C12R 1/01* | (2006.01) | |
| *C07C 11/12* | (2006.01) | |
| *C08F 136/08* | (2006.01) | |
| *C12N 9/90* | (2006.01) | |
| *C12N 15/74* | (2006.01) | |

(52) U.S. Cl.
CPC ............. *C12P 5/007* (2013.01); *C07C 11/12* (2013.01); *C08F 136/08* (2013.01); *C12N 9/88* (2013.01); *C12N 9/90* (2013.01); *C12R 1/01* (2013.01); *C12Y 402/03027* (2013.01); *C12Y 503/03002* (2013.01); *C12N 15/74* (2013.01); *C12N 2330/30* (2013.01)

(58) Field of Classification Search
CPC .................................. C12N 9/88; C12P 5/007
USPC ...................... 435/232, 167, 252.3
See application file for complete search history.

(56) References Cited

U.S. PATENT DOCUMENTS 9,777,300 B2 * 10/2017 Yeh .................. C12P 5/007
2014/0242649 A1 * 8/2014 Yeh .................. C12P 5/007
                                                      435/134

FOREIGN PATENT DOCUMENTS

| EP | 2 913 392 A1 | 9/2015 |
| WO | 2014/100726 A2 | 6/2014 |
| WO | 2014/193473 A1 | 12/2014 |
| WO | 2017/029549 A2 | 2/2017 |
| WO | 2017/029553 A2 | 2/2017 |

OTHER PUBLICATIONS

PCT/US17/53607—written Opinion (dated 2017).*
Zhou et al. Analytical Biochemistry, 440: 130-136 (2013).*
Genbank, "Isoprene Synthase [Populus Alba]", Accession No. BAD98243.1, May 10, 2005, 2 pages.
Kuzuyama, Tomohisa, "Mevalonate and Nonmevalonate Pathways for the Biosynthesis of Isoprene Units", Biosci. Biotechnol. Biochem., vol. 66, No. 8, 2002, pp. 1619-1627.
Whited et al., "Development of a Gas-Phase Bioprocess for Isoprene-Monomer Production Using Metabolic Pathway Engineering", Peer Review, Technology Update, Industrial Biotechnology, vol. 6, No. 3, Jun. 2010, pp. 152-163.

* cited by examiner

*Primary Examiner* — Tekchand Saidha
(74) *Attorney, Agent, or Firm* — Licata & Tyrrell P.C.; Robert B. Furr, Jr.

(57) ABSTRACT

Methods and compositions for synthesizing dienes and derivative thereof, such as isoprene, in *Cupriavidus necator* are provided.

9 Claims, 8 Drawing Sheets

Specification includes a Sequence Listing.

SEQUENCE LISTING

<160> NUMBER OF SEQ ID NOS: 52

<210> SEQ ID NO 1
<211> LENGTH: 182
<212> TYPE: PRT

<213> ORGANISM: E. coli

<400> SEQUENCE: 1

Met Gln Thr Glu His Val Ile Leu Leu Asn Ala Gln Gly Val Pro Thr
1               5                   10                  15

Gly Thr Leu Glu Lys Tyr Ala Ala His Thr Ala Asp Thr Arg Leu His
            20                  25                  30

Leu Ala Phe Ser Ser Trp Leu Phe Asn Ala Lys Gly Gln Leu Leu Val
        35                  40                  45

Thr Arg Arg Ala Leu Ser Lys Lys Ala Trp Pro Gly Val Trp Thr Asn
50                  55                  60

Ser Val Cys Gly His Pro Gln Leu Gly Glu Ser Asn Glu Asp Ala Val
65                  70                  75                  80

Ile Arg Arg Cys Arg Tyr Glu Leu Gly Val Glu Ile Thr Pro Pro Glu
                85                  90                  95

Ser Ile Tyr Pro Asp Phe Arg Tyr Arg Ala Thr Asp Pro Ser Gly Ile
            100                 105                 110

Val Glu Asn Glu Val Cys Pro Val Phe Ala Ala Arg Thr Thr Ser Ala
        115                 120                 125

Leu Gln Ile Asn Asp Asp Glu Val Met Asp Tyr Gln Trp Cys Asp Leu
130                 135                 140

Ala Asp Val Leu His Gly Ile Asp Ala Thr Pro Trp Ala Phe Ser Pro
145                 150                 155                 160

Trp Met Val Met Gln Ala Thr Asn Arg Glu Ala Arg Lys Arg Leu Ser
                165                 170                 175

Ala Phe Thr Gln Leu Lys
            180

<210> SEQ ID NO 2
<211> LENGTH: 350
<212> TYPE: PRT
<213> ORGANISM: B. subtilis

<400> SEQUENCE: 2

Met Val Thr Arg Ala Glu Arg Lys Arg Gln His Ile Asn His Ala Leu
1               5                   10                  15

Ser Ile Gly Gln Lys Arg Glu Thr Gly Leu Asp Asp Ile Thr Phe Val
            20                  25                  30

His Val Ser Leu Pro Asp Leu Ala Leu Glu Gln Val Asp Ile Ser Thr
        35                  40                  45

Lys Ile Gly Glu Leu Ser Ser Ser Pro Ile Phe Ile Asn Ala Met Thr
50                  55                  60

Gly Gly Gly Gly Lys Leu Thr Tyr Glu Ile Asn Lys Ser Leu Ala Arg
65                  70                  75                  80

Ala Ala Ser Gln Ala Gly Ile Pro Leu Ala Val Gly Ser Gln Met Ser
            85                  90                  95

Ala Leu Lys Asp Pro Ser Glu Arg Leu Ser Tyr Glu Ile Val Arg Lys
        100                 105                 110

Glu Asn Pro Asn Gly Leu Ile Phe Ala Asn Leu Gly Ser Glu Ala Thr
    115                 120                 125

Ala Ala Gln Ala Lys Glu Ala Val Glu Met Ile Gly Ala Asn Ala Leu
130                 135                 140

Gln Ile His Leu Asn Val Ile Gln Glu Ile Val Met Pro Glu Gly Asp
145                 150                 155                 160

Arg Ser Phe Ser Gly Ala Leu Lys Arg Ile Glu Gln Ile Cys Ser

```
                165                 170                 175
Arg Val Ser Val Pro Val Ile Val Lys Glu Val Gly Phe Gly Met Ser
            180                 185                 190

Lys Ala Ser Ala Gly Lys Leu Tyr Glu Ala Gly Ala Ala Val Asp
        195                 200                 205

Ile Gly Gly Tyr Gly Gly Thr Asn Phe Ser Lys Ile Glu Asn Leu Arg
210                 215                 220

Arg Gln Arg Gln Ile Ser Phe Phe Asn Ser Trp Gly Ile Ser Thr Ala
225                 230                 235                 240

Ala Ser Leu Ala Glu Ile Arg Ser Glu Phe Pro Ala Ser Thr Met Ile
            245                 250                 255

Ala Ser Gly Gly Leu Gln Asp Ala Leu Asp Val Ala Lys Ala Ile Ala
            260                 265                 270

Leu Gly Ala Ser Cys Thr Gly Met Ala Gly His Phe Leu Lys Ala Leu
        275                 280                 285

Thr Asp Ser Gly Glu Glu Gly Leu Leu Glu Glu Ile Gln Leu Ile Leu
        290                 295                 300

Glu Glu Leu Lys Leu Ile Met Thr Val Leu Gly Ala Arg Thr Ile Ala
305                 310                 315                 320

Asp Leu Gln Lys Ala Pro Leu Val Ile Lys Gly Glu Thr His His Trp
            325                 330                 335

Leu Thr Glu Arg Gly Val Asn Thr Ser Ser Tyr Ser Val Arg
        340                 345                 350

<210> SEQ ID NO 3
<211> LENGTH: 288
<212> TYPE: PRT
<213> ORGANISM: S. cerevisiae

<400> SEQUENCE: 3

Met Thr Ala Asp Asn Asn Ser Met Pro His Gly Ala Val Ser Ser Tyr
1               5                   10                  15

Ala Lys Leu Val Gln Asn Gln Thr Pro Glu Asp Ile Leu Glu Glu Phe
            20                  25                  30

Pro Glu Ile Ile Pro Leu Gln Gln Arg Pro Asn Thr Arg Ser Ser Glu
        35                  40                  45

Thr Ser Asn Asp Glu Ser Gly Glu Thr Cys Phe Ser Gly His Asp Glu
50                  55                  60

Glu Gln Ile Lys Leu Met Asn Glu Asn Cys Ile Val Leu Asp Trp Asp
65                  70                  75                  80

Asp Asn Ala Ile Gly Ala Gly Thr Lys Lys Val Cys His Leu Met Glu
            85                  90                  95

Asn Ile Glu Lys Gly Leu Leu His Arg Ala Phe Ser Val Phe Ile Phe
        100                 105                 110

Asn Glu Gln Gly Glu Leu Leu Leu Gln Gln Arg Ala Thr Glu Lys Ile
    115                 120                 125

Thr Phe Pro Asp Leu Trp Thr Asn Thr Cys Cys Ser His Pro Leu Cys
130                 135                 140

Ile Asp Asp Glu Leu Gly Leu Lys Gly Lys Leu Asp Asp Lys Ile Lys
145                 150                 155                 160

Gly Ala Ile Thr Ala Ala Val Arg Lys Leu Asp His Glu Leu Gly Ile
            165                 170                 175

Pro Glu Asp Glu Thr Lys Thr Arg Gly Lys Phe His Phe Leu Asn Arg
        180                 185                 190
```

Ile His Tyr Met Ala Pro Ser Asn Glu Pro Trp Gly Glu His Glu Ile
            195                 200                 205

Asp Tyr Ile Leu Phe Tyr Lys Ile Asn Ala Lys Glu Asn Leu Thr Val
210                 215                 220

Asn Pro Asn Val Asn Glu Val Arg Asp Phe Lys Trp Val Ser Pro Asn
225                 230                 235                 240

Asp Leu Lys Thr Met Phe Ala Asp Pro Ser Tyr Lys Phe Thr Pro Trp
                245                 250                 255

Phe Lys Ile Ile Cys Glu Asn Tyr Leu Phe Asn Trp Trp Glu Gln Leu
                260                 265                 270

Asp Asp Leu Ser Glu Val Glu Asn Asp Arg Gln Ile His Arg Met Leu
                275                 280                 285

<210> SEQ ID NO 4
<211> LENGTH: 347
<212> TYPE: PRT
<213> ORGANISM: E. faecalis

<400> SEQUENCE: 4

Met Asn Arg Lys Asp Glu His Leu Ser Leu Ala Lys Ala Phe His Lys
1               5                   10                  15

Glu Lys Ser Asn Asp Phe Asp Arg Val Arg Phe Val His Gln Ser Phe
                20                  25                  30

Ala Glu Ser Ala Val Asn Glu Val Asp Ile Ser Thr Ser Phe Leu Ser
            35                  40                  45

Phe Gln Leu Pro Gln Pro Phe Tyr Val Asn Ala Met Thr Gly Gly Ser
        50                  55                  60

Gln Arg Ala Lys Glu Ile Asn Gln Gln Leu Gly Ile Ile Ala Lys Glu
65                  70                  75                  80

Thr Gly Leu Leu Val Ala Thr Gly Ser Val Ser Ala Ala Leu Lys Asp
                85                  90                  95

Ala Ser Leu Ala Asp Thr Tyr Gln Ile Met Arg Lys Glu Asn Pro Asp
            100                 105                 110

Gly Leu Ile Phe Ala Asn Ile Gly Ala Gly Leu Gly Val Glu Glu Ala
        115                 120                 125

Lys Arg Ala Leu Asp Leu Phe Gln Ala Asn Ala Leu Gln Ile His Val
130                 135                 140

Asn Val Pro Gln Glu Leu Val Met Pro Glu Gly Asp Arg Asp Phe Thr
145                 150                 155                 160

Asn Trp Leu Thr Lys Ile Glu Ala Ile Val Gln Ala Val Glu Val Pro
                165                 170                 175

Val Ile Val Lys Glu Val Gly Phe Gly Met Ser Gln Glu Thr Leu Glu
            180                 185                 190

Lys Leu Thr Ser Ile Gly Val Gln Ala Ala Asp Val Ser Gly Gln Gly
        195                 200                 205

Gly Thr Ser Phe Thr Gln Ile Glu Asn Ala Arg Arg Lys Lys Arg Glu
        210                 215                 220

Leu Ser Phe Leu Asp Asp Trp Gly Gln Ser Thr Val Ile Ser Leu Leu
225                 230                 235                 240

Glu Ser Gln Asn Trp Gln Lys Lys Leu Thr Ile Leu Gly Ser Gly Gly
                245                 250                 255

Val Arg Asn Ser Leu Asp Ile Val Lys Gly Leu Ala Leu Gly Ala Lys
            260                 265                 270

Ser Met Gly Val Ala Gly Thr Ile Leu Ala Ser Leu Met Ser Lys Asn
        275                 280                 285

```
Gly Leu Glu Asn Thr Leu Ala Leu Val Gln Gln Trp Gln Glu Glu Val
    290                 295                 300

Lys Met Leu Tyr Thr Leu Leu Gly Lys Lys Thr Thr Glu Glu Leu Thr
305                 310                 315                 320

Ser Thr Ala Leu Val Leu Asp Pro Val Leu Val Asn Trp Cys His Asn
                325                 330                 335

Arg Gly Ile Asp Ser Thr Val Phe Ala Lys Arg
                340                 345

<210> SEQ ID NO 5
<211> LENGTH: 329
<212> TYPE: PRT
<213> ORGANISM: S. pyrogenes

<400> SEQUENCE: 5

Met Thr Asn Arg Lys Asp Asp His Ile Lys Tyr Ala Leu Lys Tyr Gln
1               5                   10                  15

Ser Pro Tyr Asn Ala Phe Asp Asp Ile Glu Leu Ile His His Ser Leu
                20                  25                  30

Pro Ser Tyr Asp Leu Ser Asp Ile Asp Leu Ser Thr His Phe Ala Gly
                35                  40                  45

Gln Asp Phe Asp Phe Pro Phe Tyr Ile Asn Ala Met Thr Gly Gly Ser
            50                  55                  60

Gln Lys Gly Lys Ala Val Asn Glu Lys Leu Ala Lys Val Ala Ala Ala
65                  70                  75                  80

Thr Gly Ile Val Met Val Thr Gly Ser Tyr Ser Ala Ala Leu Lys Asn
                85                  90                  95

Pro Asn Asp Asp Ser Tyr Arg Leu His Glu Val Ala Asp Asn Leu Lys
                100                 105                 110

Leu Ala Thr Asn Ile Gly Leu Asp Lys Pro Val Ala Leu Gly Gln Gln
            115                 120                 125

Thr Val Gln Glu Met Gln Pro Leu Phe Leu Gln Val His Val Asn Val
            130                 135                 140

Met Gln Glu Leu Leu Met Pro Glu Gly Glu Arg Val Phe His Thr Trp
145                 150                 155                 160

Lys Lys His Leu Ala Glu Tyr Ala Ser Gln Ile Pro Val Pro Val Ile
                165                 170                 175

Leu Lys Glu Val Gly Phe Gly Met Asp Val Asn Ser Ile Lys Leu Ala
                180                 185                 190

His Asp Leu Gly Ile Gln Thr Phe Asp Ile Ser Gly Arg Gly Gly Thr
            195                 200                 205

Ser Phe Ala Tyr Ile Glu Asn Gln Arg Gly Gly Asp Arg Ser Tyr Leu
            210                 215                 220

Asn Asp Trp Gly Gln Thr Thr Val Gln Cys Leu Leu Asn Ala Gln Gly
225                 230                 235                 240

Leu Met Asp Gln Val Glu Ile Leu Ala Ser Gly Gly Val Arg His Pro
                245                 250                 255

Leu Asp Met Ile Lys Cys Phe Val Leu Gly Ala Arg Ala Val Gly Leu
                260                 265                 270

Ser Arg Thr Val Leu Glu Leu Val Lys Tyr Pro Thr Glu Arg Val
            275                 280                 285

Ile Ala Ile Val Asn Gly Trp Lys Glu Glu Leu Lys Ile Ile Met Cys
            290                 295                 300

Ala Leu Asp Cys Lys Thr Ile Lys Glu Leu Lys Gly Val Asp Tyr Leu
```

```
                305                 310                 315                 320
Leu Tyr Gly Arg Leu Gln Gln Val Asn
                325

<210> SEQ ID NO 6
<211> LENGTH: 336
<212> TYPE: PRT
<213> ORGANISM: S. pneumonia

<400> SEQUENCE: 6

Met Thr Thr Asn Arg Lys Asp Glu His Ile Leu Tyr Ala Leu Glu Gln
1               5                   10                  15

Lys Ser Ser Tyr Asn Ser Phe Asp Glu Val Glu Leu Ile His Ser Ser
            20                  25                  30

Leu Pro Leu Tyr Asn Leu Asp Glu Ile Asp Leu Ser Thr Glu Phe Ala
        35                  40                  45

Gly Arg Lys Trp Asp Phe Pro Phe Tyr Ile Asn Ala Met Thr Gly Gly
    50                  55                  60

Ser Asn Lys Gly Arg Glu Ile Asn Gln Lys Leu Ala Gln Val Ala Glu
65                  70                  75                  80

Ser Cys Gly Ile Leu Phe Val Thr Gly Ser Tyr Ser Ala Ala Leu Lys
                85                  90                  95

Asn Pro Thr Asp Asp Ser Phe Ser Val Lys Ser Ser His Pro Asn Leu
            100                 105                 110

Leu Leu Gly Thr Asn Ile Gly Leu Asp Lys Pro Val Glu Leu Gly Leu
        115                 120                 125

Gln Thr Val Glu Glu Met Asn Pro Val Leu Leu Gln Val His Val Asn
    130                 135                 140

Val Met Gln Glu Leu Leu Met Pro Glu Gly Glu Arg Lys Phe Arg Ser
145                 150                 155                 160

Trp Gln Ser His Leu Ala Asp Tyr Ser Lys Gln Ile Pro Val Pro Ile
                165                 170                 175

Val Leu Lys Glu Val Gly Phe Gly Met Asp Ala Lys Thr Ile Glu Arg
            180                 185                 190

Ala Tyr Glu Phe Gly Val Arg Thr Val Asp Leu Ser Gly Arg Gly Gly
        195                 200                 205

Thr Ser Phe Ala Tyr Ile Glu Asn Arg Arg Ser Gly Gln Arg Asp Tyr
    210                 215                 220

Leu Asn Gln Trp Gly Gln Ser Thr Met Gln Ala Leu Leu Asn Ala Gln
225                 230                 235                 240

Glu Trp Lys Asp Lys Val Glu Leu Leu Val Ser Gly Gly Val Arg Asn
                245                 250                 255

Pro Leu Asp Met Ile Lys Cys Leu Val Phe Gly Ala Lys Ala Val Gly
            260                 265                 270

Leu Ser Arg Thr Val Leu Glu Leu Val Glu Thr Tyr Thr Val Glu Glu
        275                 280                 285

Val Ile Gly Ile Val Gln Gly Trp Lys Ala Asp Leu Arg Leu Ile Met
    290                 295                 300

Cys Ser Leu Asn Cys Ala Thr Ile Ala Asp Leu Gln Lys Val Asp Tyr
305                 310                 315                 320

Leu Leu Tyr Gly Lys Leu Lys Glu Ala Lys Asp Gln Met Lys Lys Ala
                325                 330                 335

<210> SEQ ID NO 7
<211> LENGTH: 560
```

<212> TYPE: PRT
<213> ORGANISM: Populus alba

<400> SEQUENCE: 7

```
Met Arg Cys Ser Val Ser Thr Glu Asn Val Ser Phe Thr Glu Thr Glu
1               5                   10                  15

Thr Glu Ala Arg Arg Ser Ala Asn Tyr Glu Pro Asn Ser Trp Asp Tyr
            20                  25                  30

Asp Tyr Leu Leu Ser Ser Asp Thr Asp Glu Ser Ile Glu Val Tyr Lys
        35                  40                  45

Asp Lys Ala Lys Lys Leu Glu Ala Glu Val Arg Arg Glu Ile Asn Asn
    50                  55                  60

Glu Lys Ala Glu Phe Leu Thr Leu Leu Glu Leu Ile Asp Asn Val Gln
65                  70                  75                  80

Arg Leu Gly Leu Gly Tyr Arg Phe Glu Ser Asp Ile Arg Gly Ala Leu
                85                  90                  95

Asp Arg Phe Val Ser Ser Gly Gly Phe Asp Ala Val Thr Lys Thr Ser
            100                 105                 110

Leu His Gly Thr Ala Leu Ser Phe Arg Leu Leu Arg Gln His Gly Phe
        115                 120                 125

Glu Val Ser Gln Glu Ala Phe Ser Gly Phe Lys Asp Gln Asn Gly Asn
    130                 135                 140

Phe Leu Glu Asn Leu Lys Glu Asp Ile Lys Ala Ile Leu Ser Leu Tyr
145                 150                 155                 160

Glu Ala Ser Phe Leu Ala Leu Glu Gly Glu Asn Ile Leu Asp Glu Ala
                165                 170                 175

Lys Val Phe Ala Ile Ser His Leu Lys Glu Leu Ser Glu Glu Lys Ile
            180                 185                 190

Gly Lys Glu Leu Ala Glu Gln Val Asn His Ala Leu Glu Leu Pro Leu
    195                 200                 205

His Arg Arg Thr Gln Arg Leu Glu Ala Val Trp Ser Ile Glu Ala Tyr
210                 215                 220

Arg Lys Lys Glu Asp Ala Asn Gln Val Leu Leu Glu Leu Ala Ile Leu
225                 230                 235                 240

Asp Tyr Asn Met Ile Gln Ser Val Tyr Gln Arg Asp Leu Arg Glu Thr
                245                 250                 255

Ser Arg Trp Trp Arg Arg Val Gly Leu Ala Thr Lys Leu His Phe Ala
            260                 265                 270

Arg Asp Arg Leu Ile Glu Ser Phe Tyr Trp Ala Val Gly Val Ala Phe
        275                 280                 285

Glu Pro Gln Tyr Ser Asp Cys Arg Asn Ser Val Ala Lys Met Phe Ser
    290                 295                 300

Phe Val Thr Ile Ile Asp Asp Ile Tyr Asp Val Tyr Gly Thr Leu Asp
305                 310                 315                 320

Glu Leu Glu Leu Phe Thr Asp Ala Val Glu Arg Trp Asp Val Asn Ala
                325                 330                 335

Ile Asn Asp Leu Pro Asp Tyr Met Lys Leu Cys Phe Leu Ala Leu Tyr
            340                 345                 350

Asn Thr Ile Asn Glu Ile Ala Tyr Asp Asn Leu Lys Asp Lys Gly Glu
        355                 360                 365

Asn Ile Leu Pro Tyr Leu Thr Lys Ala Trp Ala Asp Leu Cys Asn Ala
    370                 375                 380

Phe Leu Gln Glu Ala Lys Trp Leu Tyr Asn Lys Ser Thr Pro Thr Phe
385                 390                 395                 400
```

```
Asp Asp Tyr Phe Gly Asn Ala Trp Lys Ser Ser Gly Pro Leu Gln
            405                 410                 415

Leu Val Phe Ala Tyr Phe Ala Val Val Gln Asn Ile Lys Lys Glu Glu
        420                 425                 430

Ile Glu Asn Leu Gln Lys Tyr His Asp Thr Ile Ser Arg Pro Ser His
            435                 440                 445

Ile Phe Arg Leu Cys Asn Asp Leu Ala Ser Ala Ser Ala Glu Ile Ala
        450                 455                 460

Arg Gly Glu Thr Ala Asn Ser Val Ser Cys Tyr Met Arg Thr Lys Gly
465                 470                 475                 480

Ile Ser Glu Glu Leu Ala Thr Glu Ser Val Met Asn Leu Ile Asp Glu
            485                 490                 495

Thr Trp Lys Lys Met Asn Lys Glu Lys Leu Gly Gly Ser Leu Phe Ala
        500                 505                 510

Lys Pro Phe Val Glu Thr Ala Ile Asn Leu Ala Arg Gln Ser His Cys
        515                 520                 525

Thr Tyr His Asn Gly Asp Ala His Thr Ser Pro Asp Glu Leu Thr Arg
        530                 535                 540

Lys Arg Val Leu Ser Val Ile Thr Glu Pro Ile Leu Pro Phe Glu Arg
545                 550                 555                 560

<210> SEQ ID NO 8
<211> LENGTH: 549
<212> TYPE: DNA
<213> ORGANISM: E. coli

<400> SEQUENCE: 8
atgcaaacgg aacacgtcat tttattgaat gcacagggag ttcccacggg tacgctggaa      60
aagtatgccg cacacacggc agacacccgc ttacatctcg cgttctccag ttggctgttt     120
aatgccaaag acaattatt agttacccgc cgcgcactga gcaaaaaagc atggcctggc     180
gtgtggacta actcggtttg tgggcaccca caactgggag aaagcaacga agacgcagtg     240
atccgccgtt gccgttatga gcttggcgtg gaaattacgc tcctgaatc tatctatcct     300 gactttcgct accgcgccac cgatccgagt ggcattgtgg aaaatgaagt gtgtccggta     360
tttgccgcac gcaccactag tgcgttacag atcaatgatg atgaagtgat ggattatcaa     420
tggtgtgatt tagcagatgt attacacggt attgatgcca cgccgtgggc gttcagtccg     480
tggatggtga tgcaggcgac aaatcgcgaa gccagaaaac gattatctgc atttacccag     540
cttaaataa                                                              549

<210> SEQ ID NO 9
<211> LENGTH: 1053
<212> TYPE: DNA
<213> ORGANISM: B. subtilis

<400> SEQUENCE: 9
atggtcacgc gcgcggagcg caagcgccag cacatcaacc acgcgctctc catcggccag      60
aagcgcgaaa ccggcctgga cgacatcacg tttgtgcatg tctcgctgcc ggacctggcc     120
ctcgaacagg tcgacatctc gacgaagatt ggcgagctga gctcctcgtc gccgatcttc     180
atcaacgcga tgaccggcgg tggtggcaag ctgacctacg agatcaacaa gtccctggcg     240
cgcgcggcca gccaggccgg catcccgctg gcggtcggca gccagatgtc ggccctgaag     300
gaccccagcg agcgcctgtc gtacgagatt gtccgcaagg aaaacccgaa cggcctgatc     360
```

```
ttcgccaatc tgggctcgga agccaccgcg gcgcaggcca agaagcggt ggagatgatc     420 ggcgccaacg ccctgcagat ccacctgaac gtgatccaag agatcgtgat gcccgagggc     480
gaccgttcct tctccggcgc cctcaagcgc atcgagcaaa tctgcagccg cgtgtcggtg     540
cccgtcatcg tcaaggaagt gggcttcggc atgtcgaagg ccagcgccgg caagctgtac     600
gaagccggcg cggccgccgt ggacatcggc ggctacggcg gcacgaactt cagcaagatt     660
gagaatctgc cgcgccagcg gcagatcagc ttcttcaact cgtggggcat cagcacggcc     720
gcgtcgctgg cggagatccg gtccgagttc ccggcctcga ccatgatcgc gtccggtggc     780
ctccaagacg ccctggacgt cgccaaggcc atcgccctgg cgcgagctg caccggcatg     840 gccggtcact tcctgaaggc cctgaccgat agcggcgagg aaggcctgct ggaagagatc     900
cagctgatcc tggaagaact gaagctgatc atgacggtgc tgggcgcccg taccatcgcg     960
gatctgcaaa aggcgccgct cgtgatcaag ggcgaaaccc atcactggct caccgagcgg    1020
ggcgtgaaca ccagctcgta ttcggtgcgc tga                                 1053

<210> SEQ ID NO 10
<211> LENGTH: 867
<212> TYPE: DNA
<213> ORGANISM: S. cerevisiae

<400> SEQUENCE: 10
atgactgccg acaacaatag tatgccccat ggtgcagtat ctagttacgc caaattagtg      60
caaaaccaaa cacctgaaga cattttggaa gagtttcctg aaattattcc attacaacaa     120
agacctaata cccgatctag tgagacgtca atgacgaaa gcggagaaac atgtttttct     180
ggtcatgatg aggagcaaat taagttaatg aatgaaaatt gtattgtttt ggattgggac     240
gataatgcta ttggtgccgg taccaagaaa gtttgtcatt aatgaaaaa tattgaaaag     300 ggtttactac atcgtgcatt ctccgtcttt atttttcaatg aacaaggtga attacttta     360 caacaaagag ccactgaaaa ataacttttc cctgatcttt ggactaacac atgctgctct     420
catccactat gtattgatga cgaattaggt ttgaagggta agctagacga taagattaag     480
ggcgctatta ctgcggcggt gagaaaacta gatcatgaat taggtattcc agaagatgaa     540
actaagacaa ggggtaagtt tcactttta aacagaatcc attacatggc accaagcaat     600
gaaccatggg gtgaacatga aattgattac atcctatttt ataagatcaa cgctaaagaa     660
aacttgactg tcaacccaaa cgtcaatgaa gttagagact tcaaatgggt ttcaccaaat     720
gatttgaaaa ctatgtttgc tgacccaagt tacaagttta cgccttggtt taagattatt     780
tgcgagaatt acttattcaa ctggtgggag caattagatg acctttctga agtggaaaat     840
gacaggcaaa ttcatagaat gctataa                                         867

<210> SEQ ID NO 11
<211> LENGTH: 1044
<212> TYPE: DNA
<213> ORGANISM: E. faecalis

<400> SEQUENCE: 11
atgaatcgaa aagatgaaca tctatcatta gctaaagcgt tccacaaaga aaaaagtaat      60
gactttgatc gtgtgcgttt tgttcaccaa tcgtttgctg aatccgctgt taacgaagtg     120
gatatttcca cttcgtttct ttcttttcag cttccccaac cttttttatgt caatgcaatg     180 acaggtggta gtcagcgtgc aaaagaaatt aatcagcaat taggcattat tgccaaagaa     240
actggccttt tagttgcgac aggatctgtc tcggcagcgt taaaagatgc tagtttagcg     300
```

```
gatacgtatc aaattatgcg aaaagaaaac ccagatggac tcattttgc caatattggt    360 gcaggcttgg gtgtggaaga agcaaagcga gcgcttgatt tatttcaagc gaatgcctta    420
caaatccatg taaatgtgcc ccaagaattg gtcatgcctg aaggagatcg tgatttcact    480
aattggctaa ccaagattga agctatcgta caggccgtag aagtgcctgt cattgtcaaa    540
gaggttggct ttggcatgag ccaagaaacc ttagaaaaac ttacctctat cggcgttcaa    600
gcagcggatg tgagcggcca aggcggaacg agttttacac aaattgaaaa tgcccggcgg    660
aagaaacgag aactttcttt cttagatgat tgggggcaat caacggtcat ctctcttctg    720
gaatcacaaa attggcaaaa gaaactaact attctcggct ctggcggtgt gcgtaactct    780
cttgatattg tcaaaggact cgctttaggt gccaaaagca tgggagttgc tgggactatc    840
ttagcttccc ttatgagtaa aaatggttta gaaaatacct tagcccttgt acagcaatgg    900
caagaagaag tgaaaatgct ttatactctt ttaggaaaaa agacgacaga agaattgacg    960
agtaccgcac ttgtcctcga tccagtttta gttaattggt gtcataaccg tggtatcgac   1020
agcactgttt tcgcaaaacg ttaa                                           1044

<210> SEQ ID NO 12
<211> LENGTH: 990
<212> TYPE: DNA
<213> ORGANISM: S. pyrogenes

<400> SEQUENCE: 12
atgactaacc gtaaagatga tcacatcaaa tatgctctca agtaccaatc gccttataat     60
gcttttgatg acatagaact catacaccat tccttaccta gctatgattt gtctgatatt    120
gatctcagta tcattttgc tgggcaagac ttcgactttc ccttttacat caatgccatg    180
acaggaggaa gtcaaaaagg caaagctgtc aatgaaaaat tggccaaagt agcagcagca    240
acagggattg tcatggtgac agggtcttat agcgctgctt taaaaaatcc taacgacgat    300
tcctatcgtt tacatgaggt ggcagataac ttgaaactag ccacgaatat tggtctagat    360
aaacctgtgg cgctaggaca acaaacggtt caagaaatgc agcccctctt tttacaggtt    420
catgtgaatg tgatgcaaga gttgctgatg ccagagggtg agcgcgtctt tcatacctgg    480
aaaaaacacc tcgctgaata cgctagtcaa ataccagttc ctgtcattct caaagaagtt    540
ggttttggca tggatgtcaa tagtatcaag ctagcacatg acctaggcat tcaaaccttt    600
gatatttcag gtagaggagg aacttcattt gcttacattg aaaatcaaag aggggagac    660 cgctcttact aaacgattg gggacaaacc actgttcagt gcttactgaa tgcacaagga    720
ctgatggacc aagtggaaat cttagcttcg ggtggtgtca gacacccctt ggacatgatt    780
aagtgttttg tcttaggagc acgtgcagtg ggactctcac gcaccgtttt agaattggtc    840
gaaaaatacc caaccgagcg tgtgattgct atcgttaatg gctggaaaga agaattaaaa    900
atcattatgt gtgctcttga ctgtaaaact attaaagaat aaagggagt cgactactta    960 ctatatggac gcttgcagca ggtcaattag                                     990

<210> SEQ ID NO 13
<211> LENGTH: 1008
<212> TYPE: DNA
<213> ORGANISM: S. pneumonia

<400> SEQUENCE: 13
atgacgacca accgcaagga tgagcacatc ctctacgccc tggagcagaa gtcgtcgtac     60
```

```
aactcgttcg acgaagtgga actgatccac tcgtcgctgc cgctgtataa cctggacgaa    120
atcgacctgt ccaccgagtt cgccggccgc aagtgggatt tcccgttcta catcaatgcc    180
atgaccggcg gtagcaacaa gggccgcgaa atcaatcaga agctggccca ggtcgccgag    240
tcgtgcggca tcctgttcgt caccggcagc tactccgccg cgctgaagaa cccgaccgac    300
gactcgttct cggtcaagag cagccacccg aatctgctgc tgggcacgaa catcggcctc    360
gacaagcccg tcgaactggg cctgcagacc gtggaagaaa tgaacccccgt gctgctccag    420
gtgcatgtga acgtgatgca agagctgctg atgccggagg gcgaacgcaa gttccgcagc    480
tggcagtcgc acctggccga ctactcgaag cagatccccg tgccgatcgt gctgaaagaa    540
gtgggcttcg gcatggacgc caagaccatc gagcgtgcct acgagttcgg cgtgcgcacc    600
gtggacctct cgggccgcgg tggcacgagc ttcgcgtaca tcgaaaaccg gcgcagcggc    660
cagcgcgact acctgaacca gtggggccaa tcgaccatgc aggccctgct gaacgcgcaa    720
gaatggaagg acaaggtcga gctgctggtg tcggcggcg tgcgtaaccc gctcgacatg    780
atcaagtgcc tggtgttcgg cgccaaggcc gtgggcctgt cccgcaccgt gctggagctg    840
gtcgaaacct acaccgtcga agaagtcatc ggcattgtcc agggctggaa ggccgacctc    900
cgcctcatca tgtgctccct gaactgcgcc acgatcgcgg acctccagaa ggtggactat    960
ctcctctacg gcaagctcaa agaagccaag gaccagatga agaaggcg               1008

<210> SEQ ID NO 14
<211> LENGTH: 1683
<212> TYPE: DNA
<213> ORGANISM: Populus alba

<400> SEQUENCE: 14
atgcgttgta gcgttagcac cgaaaatgtg tcgtttacgg aaacggaaac cgaagctcgc     60
cgcagcgcaa actatgaacc gaactcgtgg gattacgatt acctccttag cagcgatacg    120
gatgaaagca ttgaagtgta taagacaaa gccaagaaac tggaggccga agtccgtcgc    180
gaaatcaaca atgagaaagc ggagtttctt acgttactgg aattgatcga taacgtgcaa    240
cggttaggcc tcggctaccg ctttgagagc gatatccgtg gtgcactgga ccgcttcgta    300
tcgtctggtg gttttgacgc cgttacgaaa acgagcctgc atggtacagc attgtcttt    360
cggctgttgc gccagcatgg atttgaagtg tcacaggagg cattttcagg cttcaaagac    420
cagaacggga attttttgga gaatttgaaa gaagatatca aagcgatctt atctctgtat    480
gaggcgtcat ttctcgctct ggaagggaa aatattctgg acgaagcgaa agtgttcgca    540
atttcccatc tgaaagaact ttccgaagaa aagattggga agaattggc cgaacaggtg    600
aaccatgcgc tggaactgcc actgcaccgt cgcacccaac gcctcgaagc ggtatggtcg    660
attgaagcgt atcgcaaaaa agaggatgca aatcaggttc tgctggaact ggccattctc    720
gactataaca tgattcagtc cgtctatcaa cgtgatctgc gcgaaactag tcgttggtgg    780
cgccgtgtag gacttgccac taaactgcat tttgcacgtg atcgtctgat tgagtcgttc    840
tattgggcgg ttggtgtagc gtttgagccg cagtattctg attgccgcaa tagtgtggcg    900
aaaatgttct cctttgtgac catcattgac gatatttacg acgtgtatgg caccctggat    960
gaactggaat tattcaccga tgcagtagaa cgctgggacg tcaacgcgat caatgatttg   1020
ccggattaca tgaaactgtg ttttctggcc ctgtataaca ccattaacga aattgcctat   1080
gacaacctca agacaagggg tgaaaatatc ctgccctatc tgactaaagc ttgggctgat   1140
ctgtgtaacg cgttcttaca ggaagccaaa tggctctaca acaagagtac gcctactttc   1200
```

```
gatgactact ttggcaacgc ttggaaaagc tctagcggcc ctttacaact ggtgttcgcg      1260
tatttcgccg ttgttcagaa tatcaagaaa gaagagattg agaacctcca aaagtaccac      1320
gatacgattt cgcgtccgtc acacatcttt cgcctttgca atgatttggc cagtgcatct      1380
gcagagattg cgcgcggtga aactgccaac tccgtcagtt gctacatgcg taccaaaggc      1440
atcagcgagg aactggctac cgagtcggtg atgaacttaa tcgatgaaac ctggaagaag      1500
atgaacaaag agaacttggt ggcagtctgt tttgctaaac cgttcgttga cacagcgatt      1560
aatctggcgc gtcaaagcca ctgcacctac cacaatggcg atgcccacac atccccagac      1620
gaattaaccc ggaaacgtgt cctgagtgtc atcaccgaac ccattctgcc gttcgaacgc      1680
taa                                                                   1683

<210> SEQ ID NO 15
<211> LENGTH: 7399
<212> TYPE: DNA
<213> ORGANISM: Artificial sequence
<220> FEATURE:
<223> OTHER INFORMATION: Synthetic

<400> SEQUENCE: 15
tagattaatt aacctccagc gcggggatct catgctggag ttcttcgccc accccagac       60 aagctgtgac cgtctccggg agctgcatgt gtcagaggtt ttcaccgtca tcaccgaaac     120
gcgcgaggca gcagatcaat tcgcgcgcga aggcgaagcg gcatgcataa tgtgcctgtc     180
aaatggacga agcagggatt ctgcaaaccc tatgctactc cgtcaagccg tcaattgtct     240
gattcgttac caattatgac aacttgacgg ctacatcatt cacttttttct tcacaaccgg     300 cacggaactc gctcgggctg gccccggtgc atttttttaaa tacccgcgag aaatagagtt     360
gatcgtcaaa accaacattg cgaccgacgg tggcgatagg catccgggtg gtgctcaaaa     420
gcagcttcgc ctggctgata cgttggtcct cgcgccagct taagacgcta atccctaact     480
gctggcggaa aagatgtgac agacgcgacg gcgacaagca acatgctgt gcgacgctgg     540 cgatatcaaa attgctgtct gccaggtgat cgctgatgta ctgacaagcc tcgcgtaccc     600
gattatccat cggtggatgg agcgactcgt taatcgcttc catgcgccgc agtaacaatt     660
gctcaagcag atttatcgcc agcagctccg aatagcgccc ttccccttgc ccggcgttaa     720
tgatttgccc aaacaggtcg ctgaaatgcg gctggtgcgc ttcatccggg cgaaagaacc     780
ccgtattggc aaatattgac ggccagttaa gccattcatg ccagtaggcg cgcggacgaa     840
agtaaaccca ctggtgatac cattcgcgag cctccggatg acgaccgtag tgatgaatct     900
ctcctggcgg gaacagcaaa atatcacccg gtcggcaaac aaattctcgt ccctgatttt     960
tcaccacccc ctgaccgcga atggtgagat tgagaatata acctttcatt cccagcggtc    1020
ggtcgataaa aaaatcgaga taaccgttgg cctcaatcgg cgttaaaccc gccaccagat    1080
gggcattaaa cgagtatccc ggcagcaggg gatcattttg cgcttcagcc atactttttca    1140 tactcccgcc attcagagaa gaaaccaatt gtccatattg catcagacat tgccgtcact    1200 gcgtcttta ctggctcttc tcgctaacca aaccggtaac cccgcttatt aaaagcattc     1260
tgtaacaaag cgggaccaaa gccatgacaa aaacgcgtaa caaaagtgtc tataatcacg    1320
gcagaaaagt ccacattgat tatttgcacg gcgtcacact ttgctatgcc atagcatttt    1380
tatccataag attagcggat cctacctgac gctttttatc gcaactctct actgtttctc    1440
catacccgtt ttttgggcta gaaataattt tgagctcctt taaggaagga gcgaagcatg    1500
```

```
cgttgtagcg ttagcaccga aaatgtgtcg tttacggaaa cggaaaccga agctcgccgc      1560
agcgcaaact atgaaccgaa ctcgtgggat tacgattacc tccttagcag cgatacggat      1620
gaaagcattg aagtgtataa agacaaagcc aagaaactgg aggccgaagt ccgtcgcgaa      1680
atcaacaatg agaaagcgga gtttcttacg ttactggaat tgatcgataa cgtgcaacgg      1740
ttaggcctcg gctaccgctt tgagagcgat atccgtggtg cactggaccg cttcgtatcg      1800
tctggtggtt ttgacgccgt tacgaaaacg agcctgcatg gtacagcatt gtcttttcgg      1860
ctgttgcgcc agcatggatt tgaagtgtca caggaggcat tttcaggctt caaagaccag      1920
aacgggaatt ttttggagaa tttgaaagaa gatatcaaag cgatcttatc tctgtatgag      1980
gcgtcatttc tcgctctgga aggggaaaat attctggacg aagcgaaagt gttcgcaatt      2040
tcccatctga aagaactttc cgaagaaaag attgggaaag aattggccga acaggtgaac      2100
catgcgctgg aactgccact gcaccgtcgc acccaacgcc tcgaagcggt atggtcgatt      2160
gaagcgtatc gcaaaaaaga ggatgcaaat caggttctgc tggaactggc cattctcgac      2220
tataacatga ttcagtccgt ctatcaacgt gatctgcgcg aaactagtcg ttggtggcgc      2280
cgtgtaggac ttgccactaa actgcatttt gcacgtgatc gtctgattga gtcgttctat      2340
tgggcggttg gtgtagcgtt tgagccgcag tattctgatt gccgcaatag tgtggcgaaa      2400
atgttctcct ttgtgaccat cattgacgat atttacgacg tgtatggcac cctggatgaa      2460
ctggaattat tcaccgatgc agtagaacgc tgggacgtca acgcgatcaa tgatttgccg      2520
gattacatga aactgtgttt tctggccctg tataacacca ttaacgaaat tgcctatgac      2580
aacctcaaag acaagggtga aaatatcctg ccctatctga ctaaagcttg gctgatctg      2640 tgtaacgcgt tcttacagga agccaaatgg ctctacaaca agagtacgcc tactttcgat      2700
gactactttg gcaacgcttg gaaaagctct agcggcccct tacaactggt gttcgcgtat      2760
ttcgccgttg ttcagaatat caagaaagaa gagattgaga acctccaaaa gtaccacgat      2820
acgatttcgc gtccgtcaca catctttcgc ctttgcaatg attttggccag tgcatctgca      2880 gagattgcgc gcggtgaaac tgccaactcc gtcagttgct acatgcgtac caaaggcatc      2940
agcgaggaac tggctaccga gtcggtgatg aacttaatcg atgaaacctg gaagaagatg      3000
aacaaagaga acttggtgg cagtctgttt gctaaaccgt tcgttgagac agcgattaat      3060
ctggcgcgtc aaagccactg cacctaccac aatggcgatg cccacacatc cccagacgaa      3120
ttaacccgga acgtgtcct gagtgtcatc accgaaccca ttctgccgtt cgaacgctaa      3180
gcctgctaac aaagcccgaa aggaagctga gttggctgct gccaccgctg agcactagtg      3240
cggccgcttt gcgcattcac agttctccgc aagaattgat tggctccaat tcttggagtg      3300
gtgaatccgt tagcgaggtg ccgccggctt ccattcaggt cgaggtggcc cggctccatg      3360
caccgcgacg caacgcgggg aggcagacaa ggtatagggc ggcgcctaca atccatgcca      3420
acccgttcca tgtgctcgcc gaggcggcat aaatcgccgt gacgatcagc ggtccagtga      3480
tcgaagttag gctggtaaga gccgcgagcg atccttgaag ctgtccctga tggtcgtcat      3540
ctacctgcct ggacagcatg gcctgcaacg cgggcatccc gatgccgccg aagcgagaa      3600 gaatcataat ggggaaggcc atccagcctc gcgtcgcgaa cgccagcaag acgtagccca      3660
gcgcgtcggc cgccatgccg gcgataatgg cctgcttctc gccgaaacgt ttggtggcgg      3720
gaccagtgac gaaggcttga gcgagggcgt gcaagattcc gaataccgca agcgacaggc      3780
cgatcatcgt cgcgctccag cgaaagcggt cctcgccgaa aatgacccag agcgctgccg      3840
gcacctgtcc tacgagttgc atgataaaga agacagtcat aagtgcggcg acgatagtca      3900
```

```
tgccccgcgc ccaccggaag gagctgactg ggttgaaggc tctcaagggc atcggtcgac   3960
gctctccctt atgcgactcc tgcattagga agcagcccag tagtaggttg aggccgttga   4020
gcaccgccgc cgcaaggaat ggtgcatgca aggagatggc gcccaacagt ccccggcca    4080 cggggcctgc caccataccc acgccgaaac aagcgctcat gagcccgaag tggcgagccc   4140
gatcttcccc atcggtgatg tcggcgatat aggcgccagc aaccgcacct gtggcgccgg   4200
tgatgccggc cacgatgcgt ccggcgtaga ggatccacag gacgggtgtg gtcgccatga   4260
tcgcgtagtc gatagtggct ccaagtagcg aagcgagcag gactgggcgg cggccaaagc   4320
ggtcggacag tgctccgaga acgggtgcgc atagaaattg catcaacgca tatagcgcta   4380
gcagcacgcc atagtgactg gcgatgctgt cggaatggac gatatcccgc aagaggcccg   4440
gcagtaccgc cataaccaag cctatgccta cagcatccag ggtgacggtg ccgaggatga   4500
cgatgagcgc attgttagat tcatacacg gtgcctgact gcgttagcaa tttaactgtg    4560
ataaactacc gcattaaagc ttatcgatga taagctgtca acatgagaa ttcttgaaga    4620 cgaaagggcc tcgtgatacg cctattttta taggttaatg tcatgataat aatggtttct   4680
tagacgtcag gtggcacttt tcggggaaat gtgcgcgccc gcgttcctgc tggcgctggg   4740
cctgtttctg gcgctggact tcccgctgtt ccgtcagcag cttttcgccc acggccttga   4800
tgatcgcggg ggccttggcc tgcatatccc gattcaacgg ccccagggcg tccagaacgg   4860
gcttcaggcg ctcccgaagg tctcgggccg tctcttgggc ttgatcggcc ttcttgcgca   4920
tctcacgcgc tcctgcggcg gcctgtaggg caggctcata cccctgccga accgcttttg   4980
tcagccggtc ggccacggct tccggcgtct caacgcgctt tgagattccc agcttttcgg   5040
ccaatccctg cggtgcatag gcgcgtggct cgaccgcttg cgggctgatg gtgacgtggc   5100
ccactggtgg ccgctccagg gcctcgtaga acgcctgaat gcgcgtgtga cgtgccttgc   5160
tgccctcgat gccccgttgc agccctagat cggccacagc ggccgcaaac gtggtctggt   5220
cgcgggtcat ctgcgctttg ttgccgatga actccttggc cgacagcctg ccgtcctgcg   5280
tcagcggcac cacgaacgcg gtcatgtgcg ggctggtttc gtcacggtgg atgctggccg   5340
tcacgatgcg atccgccccg tacttgtccg ccagccactt gtgcgccttc tcgaagaacg   5400
ccgcctgctg ttcttggctg gccgacttcc accattccgg gctggccgtc atgacgtact   5460
cgaccgccaa cacagcgtcc ttgcgccgct tctctggcag caactcgcgc agtcggccca   5520
tcgcttcatc ggtgctgctg gccgcccagt gctcgttctc tggcgtcctg ctggcgtcag   5580
cgttgggcgt ctcgcgctcg cggtaggcgt gcttgagact ggccgccacg ttcccattt    5640 tcgccagctt cttgcatcgc atgatcgcgt atgccgccat gcctgcccct ccttttggt    5700 gtccaaccgg ctcgacgggg gcagcgcaag gcggtgcctc cggcgggcca ctcaatgctt   5760
gagtatactc actagacttt gcttcgcaaa gtcgtgaccg cctacggcgg ctgcggcgcc   5820
ctacgggctt gctctccggg cttcgccctg cgcggtcgct gcgctccctt gcagcccgt    5880 ggatatgtgg acgatggccg cgagcggcca ccggctggct cgcttcgctc ggcccgtgga   5940
caaccctgct ggacaagctg atggacaggc tgcgcctgcc cacgagcttg accacaggga   6000
ttgcccaccg gctacccagc cttcgaccac atacccaccg gctccaactg cgcggcctgc   6060
ggccttgccc catcaatttt tttaattttc tctggggaaa agcctccggc ctgcggcctg   6120
cgcgcttcgc ttgccggttg gacaccaagt ggaaggcggg tcaaggctcg cgcagcgacc   6180
gcgcagcggc ttggccttga cgcgcctgga acgacccaag cctatgcgag tggggggcagt 6240
```

| | | |
|---|---|---|
| cgaagggcga agcccgcccg cctgccccec gagcctcacg gcggcgagtg cggggggttcc | 6300 |
| aaggggggcag cgccaccttg ggcaaggccg aaggccgcgc agtcgatcaa caagcccegg | 6360 |
| aggggccact tttgccgga ggggagccg cgccgaaggc gtgggggaac cccgcagggg | 6420 |
| tgcccttctt tgggcaccaa agaactagat atagggcgaa atgcgaaaga cttaaaaatc | 6480 |
| aacaacttaa aaaggggggg tacgcaacag ctcattgcgg cacccccgc aatagctcat | 6540 |
| tgcgtaggtt aaagaaaatc tgtaattgac tgccactttt acgcaacgca taattgttgt | 6600 |
| cgcgctgccg aaaagttgca gctgattgcg catggtgccg caaccgtgcg gcacccctac | 6660 |
| cgcatggaga taagcatggc cacgcagtcc agagaaatcg gcattcaagc caagaacaag | 6720 |
| cccggtcact gggtgcaaac ggaacgcaaa gcgcatgagg cgtgggccgg gcttattgcg | 6780 |
| aggaaaccca cggcggcaat gctgctgcat cacctcgtgg cgcagatggg ccaccagaac | 6840 |
| gccgtggtgg tcagccagaa gacactttcc aagctcatcg gacgttcttt gcggacggtc | 6900 |
| caatacgcag tcaaggactt ggtggccgag cgctggatct ccgtcgtgaa gctcaacggc | 6960 |
| cccggcaccg tgtcggccta cgtggtcaat gaccgcgtgg cgtggggcca gccccgcgac | 7020 |
| cagttgcgcc tgtcggtgtt cagtgccgcc gtggtggttg atcacgacga ccaggacgaa | 7080 |
| tcgctgttgg ggcatggcga cctgcgccg atcccgaccc tgtatccggg cgagcagcaa | 7140 |
| ctaccgaccg gcccccggcga ggagccgccc agccagcccg gcattccggg catggaacca | 7200 |
| gacctgccag ccttgaccga aacgaggaa tgggaacggc gcgggcagca gcgcctgccg | 7260 |
| atgcccgatg agccgtgttt tctggacgat ggcgagccgt ggagccgcc gacacgggtc | 7320 |
| acgctgccgc gccggtagca cttgggttgc gcagcaaccc gtaagtgcgc tgttccagac | 7380 |
| tatcggctgt agccgcctc | 7399 |

<210> SEQ ID NO 16
<211> LENGTH: 7960
<212> TYPE: DNA
<213> ORGANISM: Artificial sequence
<220> FEATURE:
<223> OTHER INFORMATION: Synthetic

<400> SEQUENCE: 16

| | | |
|---|---|---|
| ctcgatgccc cgttgcagcc ctagatcggc cacagcggcc gcaaacgtgg tctggtcgcg | 60 |
| ggtcatctgc gctttgttgc cgatgaactc cttggccgac agcctgccgt cctgcgtcag | 120 |
| cggcaccacg aacgcggtca tgtgcgggct ggtttcgtca cggtggatgc tggccgtcac | 180 |
| gatgcgatcc gccccgtact tgtccgccag ccacttgtgc gccttctcga agaacgccgc | 240 |
| ctgctgttct tggctggccg acttccacca ttccgggctg gccgtcatga cgtactcgac | 300 |
| cgccaacaca gcgtccttgc gccgcttctc tggcagcaac tcgcgcagtc ggcccatcgc | 360 |
| ttcatcggtg ctgctggccg cccagtgctc gttctctggc gtcctgctgg cgtcagcgtt | 420 |
| gggcgtctcg cgctcgcggt aggcgtgctt gagactggcc gccacgttgc ccatttttcgc | 480 |
| cagcttcttg catcgcatga tcgcgtatgc cgccatgcct gcccctcccct tttggtgtcc | 540 |
| aaccggctcg acggggcag cgcaaggcgg tgcctccggc gggccactca atgcttgagt | 600 |
| atactcacta gactttgctt cgcaaagtcg tgaccgccta cggcggctgc ggcgccctac | 660 |
| gggcttgctc tccgggcttc gccctgcgcg gtcgctgcgc tcccttgcca gcccgtggat | 720 |
| atgtggacga tggccgcgag cggccaccgg ctggctcgct tcgctcggcc cgtggacaac | 780 |
| cctgctggac aagctgatgg acaggctgcg cctgcccacg agcttgacca cagggattgc | 840 |
| ccaccggcta cccagccttc gaccacatac ccaccggctc caactgcgcg gcctgcggcc | 900 |

```
ttgccccatc aattttttta attttctctg gggaaaagcc tccggcctgc ggcctgcgcg   960
cttcgcttgc cggttggaca ccaagtggaa ggcgggtcaa ggctcgcgca gcgaccgcgc  1020
agcggcttgg ccttgacgcg cctggaacga cccaagccta tgcgagtggg ggcagtcgaa  1080
ggcgaagccc gcccgcctgc cccccgagcc tcacggcggc gagtgcgggg gttccaaggg  1140
ggcagcgcca ccttgggcaa ggccgaaggc cgcgcagtcg atcaacaagc cccggagggg  1200
ccactttttg ccggaggggg agccgcgccg aaggcgtggg ggaaccccgc aggggtgccc  1260
ttctttgggc accaaagaac tagatatagg gcgaaatgcg aaagacttaa aaatcaacaa  1320
cttaaaaaag gggggtacgc aacagctcat tgcggcaccc cccgcaatag ctcattgcgt  1380
aggttaaaga aaatctgtaa ttgactgcca cttttacgca acgcataatt gttgtcgcgc  1440
tgccgaaaag ttgcagctga ttgcgcatgg tgccgcaacc gtgcggcacc ctaccgcatg  1500
gagataagca tggccacgca gtccagagaa atcggcattc aagccaagaa caagcccggt  1560
cactgggtgc aaacggaacg caaagcgcat gaggcgtggg ccgggcttat tgcgaggaaa  1620
cccacggcgg caatgctgct gcatcacctc gtggcgcaga tgggccacca gaacgccgtg  1680
gtggtcagcc agaagacact ttccaagctc atcggacgtt ctttgcggac ggtccaatac  1740
gcagtcaagg acttggtggc cgagcgctgg atctccgtcg tgaagctcaa cggccccggc  1800
accgtgtcgg cctacgtggt caatgaccgc gtggcgtggg gccagccccg cgaccagttg  1860
cgcctgtcgg tgttcagtgc cgccgtggtg gttgatcacg acgaccagga cgaatcgctg  1920
ttggggcatg gcgacctgcg ccgcatcccg accctgtatc cgggcgagca gcaactaccg  1980
accggccccg gcgaggagcc gcccagccag cccggcattc cggcatgga accagacctg  2040
ccagccttga ccgaaacgga ggaatgggaa cggcgcgggc agcagcgcct gccgatgccc  2100
gatgagccgt gttttctgga cgatggcgag ccgttggagc cgccgacacg ggtcacgctg  2160
ccgcgccggt agcacttggg ttgcgcagca cccgtaagt gcgctgttcc agactatcgg  2220
ctgtagccgc ctctagatta attaacctcc agcgcgggga tctcatgctg gagttcttcg  2280
cccaccccca gacaagctgt gaccgtctcc gggagctgca tgtgtcagag gttttcaccg  2340
tcatcaccga aacgcgcgag gcagcagatc aattcgcgcg cgaaggcgaa gcggcatgca  2400
taatgtgcct gtcaaatgga cgaagcaggg attctgcaaa ccctatgcta ctccgtcaag  2460
ccgtcaattg tctgattcgt taccaattat gacaacttga cggctacatc attcactttt  2520
tcttcacaac cggcacggaa ctcgctcggg ctggccccgg tgcattttttt aaatacccgc  2580
gagaaataga gttgatcgtc aaaaccaaca ttgcgaccga cggtggcgat aggcatccgg  2640
gtggtgctca aaagcagctt cgcctggctg atacgttggt cctcgcgcca gcttaagacg  2700
ctaatcccta actgctggcg gaaaagatgt gacagacgcg acggcgacaa gcaaacatgc  2760
tgtgcgacgc tggcgatatc aaaattgctg tctgccaggt gatcgctgat gtactgacaa  2820
gcctcgcgta cccgattatc catcggtgga tggagcgact cgttaatcgc ttccatgcgc  2880
cgcagtaaca attgctcaag cagatttatc gccagcagct ccgaatagcg cccttcccct  2940
tgcccggcgt taatgatttg cccaaacagg tcgctgaaat gcggctggtg cgcttcatcc  3000
gggcgaaaga accccgtatt ggcaaatatt gacggccagt taagccattc atgccagtag  3060
gcgcgcggac gaaagtaaac ccactggtga taccattcgc gagcctccgg atgacgaccg  3120
tagtgatgaa tctctcctgg cgggaacagc aaaatatcac ccggtcggca aacaaattct  3180
cgtccctgat ttttcaccac cccctgaccg cgaatggtga gattgagaat ataacctttc  3240
```

```
attcccagcg gtcggtcgat aaaaaaatcg agataaccgt tggcctcaat cggcgttaaa    3300
cccgccacca gatgggcatt aaacgagtat cccggcagca ggggatcatt ttgcgcttca    3360
gccatacttt tcatactccc gccattcaga gaagaaacca attgtccata ttgcatcaga    3420
cattgccgtc actgcgtctt ttactggctc ttctcgctaa ccaaaccggt aaccccgctt    3480
attaaaagca ttctgtaaca aagcgggacc aaagccatga caaaaacgcg taacaaaagt    3540
gtctataatc acggcagaaa agtccacatt gattatttgc acggcgtcac actttgctat    3600
gccatagcat ttttatccat aagattagcg gatcctacct gacgcttttt atcgcaactc    3660
tctactgttt ctccataccc gtttttgggg ctagaaataa ttttgagctc gccaaggaga    3720
tataatgcaa acggaacacg tcattttatt gaatgcacag ggagttccca cgggtacgct    3780
ggaaaagtat gccgcacaca cggcagacac ccgcttacat ctcgcgttct ccagttggct    3840
gtttaatgcc aaaggacaat tattagttac ccgccgcgca ctgagcaaaa aagcatggcc    3900
tggcgtgtgg actaactcgg tttgtgggca cccacaactg ggagaaagca acgaagacgc    3960
agtgatccgc cgttgccgtt atgagcttgg cgtggaaatt acgcctcctg aatctatcta    4020
tcctgacttt cgctaccgcg ccaccgatcc gagtggcatt gtggaaaatg aagtgtgtcc    4080
ggtatttgcc gcacgcacca ctagtgcgtt acagatcaat gatgatgaag tgatggatta    4140
tcaatggtgt gatttagcag atgtattaca cggtattgat gccacgccgt gggcgttcag    4200
tccgtggatg gtgatgcagg cgacaaatcg cgaagccaga aaacgattat ctgcatttac    4260
ccagcttaaa taactttaag gaaggagcga agcatgcgtt gtagcgttag caccgaaaat    4320
gtgtcgttta cggaaacgga aaccgaagct cgccgcagcg caaactatga accgaactcg    4380
tgggattacg attacctcct tagcagcgat acggatgaaa gcattgaagt gtataaagac    4440
aaagccaaga aactggaggc cgaagtccgt cgcgaaatca acaatgagaa agcggagttt    4500
cttacgttac tggaattgat cgataacgtg caacggttag gcctcggcta ccgctttgag    4560
agcgatatcc gtggtgcact ggaccgcttc gtatcgtctg gtggttttga cgccgttacg    4620
aaaacgagcc tgcatggtac agcattgtct tttcggctgt tgcgccagca tggatttgaa    4680
gtgtcacagg aggcattttc aggcttcaaa gaccagaacg ggaatttttt ggagaatttg    4740
aaagaagata tcaaagcgat cttatctctg tatgaggcgt catttctcgc tctggaaggg    4800
gaaaatattc tggacgaagc gaaagtgttc gcaatttccc atctgaaaga actttccgaa    4860
gaaaagattg ggaaagaatt ggccgaacag gtgaaccatg cgctggaact gccactgcac    4920
cgtcgcaccc aacgcctcga agcggtatgg tcgattgaag cgtatcgcaa aaaagaggat    4980
gcaaatcagg ttctgctgga actggccatt ctcgactata acatgattca gtccgtctat    5040
caacgtgatc tgcgcgaaac tagtcgttgg tggcgccgtg taggacttgc cactaaactg    5100
cattttgcac gtgatcgtct gattgagtcg ttctattggg cggttggtgt agcgtttgag    5160
ccgcagtatt ctgattgccg caatagtgtg gcgaaaatgt tctcctttgt gaccatcatt    5220
gacgatattt acgacgtgta tggcacccctg gatgaactgg aattattcac cgatgcagta    5280
gaacgctggg acgtcaacgc gatcaatgat tgccggatt acatgaaact gtgttttctg    5340
gccctgtata acaccattaa cgaaattgcc tatgacaacc tcaaagacaa gggtgaaaat    5400
atcctgccct atctgactaa agcttgggct gatctgtgta acgcgttctt acaggaagcc    5460
aaatggctct acaacaagag tacgcctact ttcgatgact actttggcaa cgcttggaaa    5520
agctctagcg gcccttttaca actggtgttc gcgtatttcg ccgttgttca gaatatcaag    5580
aaagaagaga ttgagaacct ccaaaagtac cacgatacga tttcgcgtcc gtcacacatc    5640
```

```
tttcgccttt gcaatgattt ggccagtgca tctgcagaga ttgcgcgcgg tgaaactgcc    5700
aactccgtca gttgctacat gcgtaccaaa ggcatcagcg aggaactggc taccgagtcg    5760
gtgatgaact taatcgatga aacctggaag aagatgaaca aagagaaact tggtggcagt    5820
ctgtttgcta aaccgttcgt tgagacacgc attaatctgg cgcgtcaaag ccactgcacc    5880
taccacaatg gcgatgccca cacatcccca gacgaattaa cccggaaacg tgtcctgagt    5940
gtcatcaccg aacccattct gccgttcgaa cgctaagcct gctaacaaag cccgaaagga    6000
agctgagttg gctgctgcca ccgctgagca ctagtgcggc cgctttgcgc attcacagtt    6060
ctccgcaaga attgattggc tccaattctt ggagtggtga atccgttagc gaggtgccgc    6120
cggcttccat tcaggtcgag gtggcccggc tccatgcacc gcgacgcaac gcggggaggc    6180
agacaaggta tagggcggcg cctacaatcc atgccaaccc gttccatgtg ctcgccgagg    6240
cggcataaat cgccgtgacg atcagcggtc cagtgatcga agttaggctg gtaagagccg    6300
cgagcgatcc ttgaagctgt ccctgatggt cgtcatctac ctgcctggac agcatggcct    6360
gcaacgcggg catcccgatg ccgccggaag cgagaagaat cataatgggg aaggccatcc    6420
agcctcgcgt cgcgaacgcc agcaagacgt agcccagcgc gtcggccgcc atgccggcga    6480
taatggcctg cttctcgccg aaacgtttgg tggcgggacc agtgacgaag gcttgagcga    6540
gggcgtgcaa gattccgaat accgcaagcg acaggccgat catcgtcgcg ctccagcgaa    6600
agcggtcctc gccgaaaatg acccagagcg ctgccggcac ctgtcctacg agttgcatga    6660
taaagaagac agtcataagt gcggcgacga tagtcatgcc ccgcgcccac cggaaggagc    6720
tgactgggtt gaaggctctc aagggcatcg gtcgacgctc tcccttatgc gactcctgca    6780
ttaggaagca gcccagtagt aggttgaggc cgttgagcac cgccgccgca aggaatggtg    6840
catgcaagga gatggcgccc aacagtcccc cggccacggg gcctgccacc atacccacgc    6900
cgaaacaagc gctcatgagc ccgaagtggc gagcccgatc ttccccatcg gtgatgtcgg    6960
cgatataggc gccagcaacc gcacctgtgg cgccggtgat gccggccacg atgcgtccgg    7020
cgtagaggat ccacaggacg ggtgtggtcg ccatgatcgc gtagtcgata gtggctccaa    7080
gtagcgaagc gagcaggact gggcggcggc caaagcggtc ggacagtgct ccgagaacgg    7140
gtgcgcatag aaattgcatc aacgcatata gcgctagcag cacgccatag tgactggcga    7200
tgctgtcgga atggacgata tcccgcaaga ggcccggcag taccggcata accaagccta    7260
tgcctacagc atccagggtg acggtgccga ggatgacgat gagcgcattg ttagatttca    7320
tacacggtgc ctgactgcgt tagcaattta actgtgataa actaccgcat taaagcttat    7380
cgatgataag ctgtcaaaca tgagaattct tgaagacgaa agggcctcgt gatacgccta    7440
tttttatagg ttaatgtcat gataataatg gtttcttaga cgtcaggtgg cacttttcgg    7500
ggaaatgtgc gcgcccgcgt tcctgctggc gctgggcctg tttctggcgc tggacttccc    7560
gctgttccgt cagcagcttt tcgcccacgg ccttgatgat cgcggcggcc ttggcctgca    7620
tatcccgatt caacggcccc agggcgtcca gaacgggctt caggcgctcc gaaggtctc    7680
gggccgtctc ttgggcttga tcggccttct tgcgcatctc acgcgctcct gcggcggcct    7740
gtagggcagg ctcataccccc tgccgaaccg cttttgtcag ccggtcggcc acggcttccg    7800
gcgtctcaac gcgctttgag attcccagct tttcggccaa tccctgcggt gcataggcgc    7860
gtggctcgac cgcttgcggg ctgatggtga cgtggcccac tggtggccgc tccagggcct    7920
cgtagaacgc ctgaatgcgc gtgtgacgtg ccttgctgcc                          7960
```

<210> SEQ ID NO 17
<211> LENGTH: 8464
<212> TYPE: DNA
<213> ORGANISM: Artificial sequence
<220> FEATURE:
<223> OTHER INFORMATION: Synthetic

<400> SEQUENCE: 17

```
ctcgatgccc cgttgcagcc ctagatcggc cacagcggcc gcaaacgtgg tctggtcgcg      60
ggtcatctgc gctttgttgc cgatgaactc cttggccgac agcctgccgt cctgcgtcag     120
cggcaccacg aacgcggtca tgtgcgggct ggtttcgtca cggtggatgc tggccgtcac     180
gatgcgatcc gccccgtact tgtccgccag ccacttgtgc gccttctcga agaacgccgc     240
ctgctgttct ggctggccg acttccacca ttccgggctg gccgtcatga cgtactcgac     300
cgccaacaca gcgtccttgc gccgcttctc tggcagcaac tcgcgcagtc ggcccatcgc     360
ttcatcggtg ctgctggccg cccagtgctc gttctctggc gtcctgctgg cgtcagcgtt     420
gggcgtctcg cgctcgcggt aggcgtgctt gagactggcc gccacgttgc ccattttcgc     480
cagcttcttg catcgcatga tcgcgtatgc cgccatgcct gcccctccct tttggtgtcc     540
aaccggctca cggggcag cgcaaggcgg tgcctccggc gggccactca atgcttgagt     600
atactcacta gactttgctt cgcaaagtcg tgaccgccta cggcggctgc ggcgccctac     660
gggcttgctc tccgggcttc gccctgcgcg gtcgctgcgc tcccttgcca gcccgtggat     720
atgtggacga tggccgcgag cggccaccgg ctggctcgct tcgctcggcc cgtggacaac     780
cctgctggac aagctgatgg acaggctgcg cctgcccacg agcttgacca cagggattgc     840
ccaccggcta cccagccttc gaccacatac ccaccggctc caactgcgcg gcctgcggcc     900
ttgccccatc aatttttta attttctctg gggaaaagcc tccggcctgc ggcctgcgcg     960
cttcgcttgc cggttggaca ccaagtggaa ggcgggtcaa ggctcgcgca gcgaccgcgc    1020
agcggcttgg ccttgacgcg cctggaacga cccaagccta tgcgagtggg ggcagtcgaa    1080
ggcgaagccc gcccgcctgc cccccgagcc tcacggcggc gagtgcgggg gttccaaggg    1140
ggcagcgcca ccttgggcaa ggccgaaggc cgcgcagtcg atcaacaagc cccggagggg    1200
ccacttttg ccggaggggg agccgcgccg aaggcgtggg ggaaccccgc aggggtgccc    1260
ttctttgggc accaaagaac tagatatagg gcgaaatgcg aaagacttaa aaatcaacaa    1320
cttaaaaag gggggtacgc aacagctcat tgcggcaccc ccgcaatag ctcattgcgt    1380
aggttaaaga aaatctgtaa ttgactgcca cttttacgca acgcataatt gttgtcgcgc    1440
tgccgaaaag ttgcagctga ttgcgcatgg tgccgcaacc gtgcggcacc ctaccgcatg    1500
gagataagca tggccacgca gtccagagaa atcggcattc aagccaagaa caagcccggt    1560
cactgggtgc aaacggaacg caaagcgcat gaggcgtggg ccgggcttat tgcgaggaaa    1620
cccacggcgg caatgctgct gcatcacctc gtggcgcaga tgggccacca gaacgccgtg    1680
gtggtcagcc agaagacact ttccaagctc atcggacgtt ctttgcggac ggtccaatac    1740
gcagtcaagg acttggtggc cgagcgctgg atctccgtcg tgaagctcaa cggccccggc    1800
accgtgtcgg cctacgtggt caatgaccgc gtggcgtggg ccagccccg cgaccagttg    1860
cgcctgtcgg tgttcagtgc cgccgtggtg gttgatcacg acgaccagga cgaatcgctg    1920
ttggggcatg cgacctgcg ccgcatcccg accctgtatc gggcgagca gcaactaccg    1980
accgccccg cgaggagcc gcccagccag cccggcattc cggcatgga accagacctg    2040
ccagccttga ccgaaacgga ggaatgggaa cggcgcgggc agcagcgcct gccgatgccc    2100
```

```
gatgagccgt gttttctgga cgatggcgag ccgttggagc cgccgacacg ggtcacgctg    2160
ccgcgccggt agcacttggg ttgcgcagca acccgtaagt gcgctgttcc agactatcgg    2220
ctgtagccgc ctctagatta attaacctcc agcgcgggga tctcatgctg gagttcttcg    2280 cccacccca  gacaagctgt gaccgtctcc gggagctgca tgtgtcagag gttttcaccg    2340
tcatcaccga aacgcgcgag gcagcagatc aattcgcgcg cgaaggcgaa gcggcatgca    2400
taatgtgcct gtcaaatgga cgaagcaggg attctgcaaa ccctatgcta ctccgtcaag    2460
ccgtcaattg tctgattcgt taccaattat gacaacttga cggctacatc attcactttt    2520
tcttcacaac cggcacggaa ctcgctcggg ctggccccgg tgcattttt  aaatacccgc    2580 gagaaataga gttgatcgtc aaaaccaaca ttgcgaccga cggtggcgat aggcatccgg    2640
gtggtgctca aaagcagctt cgcctggctg atacgttggt cctcgcgcca gcttaagacg    2700
ctaatcccta actgctggcg gaaaagatgt gacagacgcg acggcgacaa gcaaacatgc    2760
tgtgcgacgc tggcgatatc aaaattgctg tctgccaggt gatcgctgat gtactgacaa    2820
gcctcgcgta cccgattatc catcggtgga tgagcgact  cgttaatcgc ttccatgcgc    2880
cgcagtaaca attgctcaag cagatttatc gccagcagct ccgaatagcg ccctccccct    2940
tgcccggcgt taatgatttg cccaaacagg tcgctgaaat gcggctggtg cgcttcatcc    3000
gggcgaaaga accccgtatt ggcaaatatt gacggcagt  taagccattc atgccagtag    3060
gcgcgcggac gaaagtaaac ccactggtga taccattcgc gagcctccgg atgacgaccg    3120
tagtgatgaa tctctcctgg cgggaacagc aaaatatcac ccggtcggca aacaaattct    3180
cgtccctgat ttttcaccac cccctgaccg cgaatggtga gattgagaat ataacctttc    3240
attcccagcg gtcggtcgat aaaaaaatcg agataaccgt tggcctcaat cggcgttaaa    3300
cccgccacca gatgggcatt aaacgagtat cccggcagca ggggatcatt ttgcgcttca    3360
gccatacttt tcatactccc gccattcaga gaagaaacca attgtccata ttgcatcaga    3420
cattgccgtc actgcgtctt ttactggctc ttctcgctaa ccaaaccggt aaccccgctt    3480
attaaaagca ttctgtaaca aagcgggacc aaagccatga caaaaacgcg taacaaaagt    3540
gtctataatc acggcagaaa agtccacatt gattatttgc acggcgtcac actttgctat    3600
gccatagcat ttttatccat aagattagcg gatcctacct gacgcttttt atcgcaactc    3660
tctactgttt ctccatacc  gttttttggg ctagaaataa ttttgagctc gccaaggaga    3720
tataatggtc acgcgcgcgg agcgcaagcg ccagcacatc aaccacgcgc tctccatcgg    3780
ccagaagcgc gaaaccggcc tggacgacat cacgtttgtg catgtctcgc tgccggacct    3840
ggccctcgaa caggtcgaca tctcgacgaa gattggcgag ctgagctcct cgtcgccgat    3900
cttcatcaac gcgatgaccg gcggtggtgg caagctgacc tacgagatca acaagtccct    3960
ggcgcgcgcg ccagccagg  ccggcatccc gctggcggtc ggcagccaga tgtcggccct    4020
gaaggacccc agcgagcgcc tgtcgtacga gattgtccgc aaggaaaacc gaacggcct    4080 gatcttcgcc aatctgggct cggaagccac cgcggcgcag gccaaagaag cggtggagat    4140
gatcggcgcc aacgccctgc agatccacct gaacgtgatc caagagatcg tgatgcccga    4200
gggcgaccgt tccttctccg cgccctcaa  gcgcatcgag caaatctgca gccgcgtgtc    4260
ggtgcccgtc atcgtcaagg aagtgggctt cggcatgtcg aaggccagcg ccggcaagct    4320
gtacgaagcc ggcgcggccg ccgtggacat cggcggctac ggcggcacga acttcagcaa    4380
gattgagaat ctgcgccgcc agcggcagat cagcttcttc aactcgtggg gcatcagcac    4440
```

-continued

```
ggccgcgtcg ctggcggaga tccggtccga gttcccggcc tcgaccatga tcgcgtccgg    4500
tggcctccaa gacgccctgg acgtcgccaa ggccatcgcc ctgggcgcga gctgcaccgg    4560
catggccggt cacttcctga aggccctgac cgatagcggc gaggaaggcc tgctggaaga    4620
gatccagctg atcctggaag aactgaagct gatcatgacg gtgctgggcg cccgtaccat    4680
cgcggatctg caaaaggcgc cgctcgtgat caagggcgaa acccatcact ggctcaccga    4740
gcggggcgtg aacaccagct cgtattcggt gcgctgactt taaggaagga gcgaagcatg    4800
cgttgtagcg ttagcaccga aaatgtgtcg tttacggaaa cggaaaccga agctcgccgc    4860
agcgcaaact atgaaccgaa ctcgtggat tacgattacc tccttagcag cgatacggat    4920
gaaagcattg aagtgtataa agacaaagcc aagaaactgg aggccgaagt ccgtcgcgaa    4980
atcaacaatg agaaagcgga gtttcttacg ttactggaat tgatcgataa cgtgcaacgg    5040
ttaggcctcg gctaccgctt tgagagcgat atccgtggtg cactggaccg cttcgtatcg    5100
tctggtggtt ttgacgccgt tacgaaaacg agcctgcatg gtacagcatt gtcttttcgg    5160
ctgttgcgcc agcatggatt tgaagtgtca caggaggcat tttcaggctt caaagaccag    5220
aacgggaatt ttttggagaa tttgaaagaa gatatcaaag cgatcttatc tctgtatgag    5280
gcgtcatttc tcgctctgga aggggaaaat attctggacg aagcgaaagt gttcgcaatt    5340
tcccatctga aagaactttc cgaagaaaag attgggaaag aattggccga acaggtgaac    5400
catgcgctgg aactgccact gcaccgtcgc acccaacgcc tcgaagcggt atggtcgatt    5460
gaagcgtatc gcaaaaaaga ggatgcaaat caggttctgc tggaactggc cattctcgac    5520
tataacatga ttcagtccgt ctatcaacgt gatctgcgcg aaactagtcg ttggtggcgc    5580
cgtgtaggac ttgccactaa actgcatttt gcacgtgatc gtctgattga gtcgttctat    5640
tgggcggttg gtgtagcgtt tgagccgcag tattctgatt gccgcaatag tgtggcgaaa    5700
atgttctcct ttgtgaccat cattgacgat atttacgacg tgtatggcac cctggatgaa    5760
ctggaattat tcaccgatgc agtagaacgc tgggacgtca acgcgatcaa tgatttgccg    5820
gattacatga aactgtgttt tctggccctg tataacacca ttaacgaaat tgcctatgac    5880
aacctcaaag acaagggtga aaatatcctg ccctatctga ctaaagcttg gctgatctg    5940 tgtaacgcgt tcttacagga agccaaatgg ctctacaaca agagtacgcc tactttcgat    6000
gactactttg gcaacgcttg gaaaagctct agcggccctt tacaactggt gttcgcgtat    6060
ttcgccgttg ttcagaatat caagaaagaa gagattgaga acctccaaaa gtaccacgat    6120
acgatttcgc gtccgtcaca catctttcgc ctttgcaatg atttggccag tgcatctgca    6180
gagattgcgc gcggtgaaac tgccaactcc gtcagttgct acatgcgtac caaaggcatc    6240
agcgaggaac tggctaccga gtcggtgatg aacttaatcg atgaaacctg aagaagatg    6300 aacaaagaga acttggtgg cagtctgttt gctaaaccgt tcgttgagac agcgattaat    6360
ctggcgcgtc aaagccactg cacctaccac aatggcgatg cccacacatc cccagacgaa    6420
ttaacccgga aacgtgtcct gagtgtcatc accgaaccca ttctgccgtt cgaacgctaa    6480
gcctgctaac aaagcccgaa aggaagctga gttggctgct gccaccgctg agcactagtg    6540
cggccgcttt gcgcattcac agttctccgc aagaattgat tggctccaat tcttggagtg    6600
gtgaatccgt tagcgaggtg ccgccggctt ccattcaggt cgaggtggcc cggctccatg    6660
caccgcgacg caacgcgggg aggcagacaa ggtataggc ggcgcctaca atccatgcca    6720
acccgttcca tgtgctcgcc gaggcggcat aaatcgccgt gacgatcagc ggtccagtga    6780
tcgaagttag gctggtaaga gccgcgagcg atccttgaag ctgtccctga tggtcgtcat    6840
```

-continued

```
ctacctgcct ggacagcatg gcctgcaacg cgggcatccc gatgccgccg aagcgagaa    6900 gaatcataat ggggaaggcc atccagcctc gcgtcgcgaa cgccagcaag acgtagccca    6960
gcgcgtcggc cgccatgccg gcgataatgg cctgcttctc gccgaaacgt ttggtggcgg    7020
gaccagtgac gaaggcttga gcgagggcgt gcaagattcc gaataccgca agcgacaggc    7080
cgatcatcgt cgcgctccag cgaaagcggt cctcgccgaa aatgacccag agcgctgccg    7140
gcacctgtcc tacgagttgc atgataaaga agacagtcat aagtgcgcg acgatagtca    7200 tgccccgcgc ccaccggaag gagctgactg ggttgaaggc tctcaagggc atcggtcgac    7260
gctctccctt atgcgactcc tgcattagga agcagcccag tagtaggttg aggccgttga    7320
gcaccgccgc cgcaaggaat ggtgcatgca aggagatggc gcccaacagt cccccggcca    7380
cggggcctgc caccataccc acgccgaaac aagcgctcat gagcccgaag tggcgagccc    7440
gatcttcccc atcggtgatg tcggcgatat aggcgccagc aaccgcacct gtggcgccgg    7500
tgatgccggc cacgatgcgt ccggcgtaga ggatccacag gacgggtgtg gtcgccatga    7560
tcgcgtagtc gatagtggct ccaagtagcg aagcgagcag gactgggcgg cggccaaagc    7620
ggtcggacag tgctccgaga acgggtgcgc atagaaattg catcaacgca tatagcgcta    7680
gcagcacgcc atagtgactg gcgatgctgt cggaatggac gatatcccgc aagaggcccg    7740
gcagtaccgg cataaccaag cctatgccta cagcatccag ggtgacggtg ccgaggatga    7800
cgatgagcgc attgttagat tcatacacg gtgcctgact gcgttagcaa tttaactgtg    7860
ataaactacc gcattaaagc ttatcgatga taagctgtca acatgagaa ttcttgaaga    7920 cgaaagggcc tcgtgatacg cctattttta taggttaatg tcatgataat aatggtttct    7980
tagacgtcag gtggcacttt tcggggaaat gtgcgcgccc gcgttcctgc tggcgctggg    8040
cctgtttctg gcgctggact tcccgctgtt ccgtcagcag cttttcgccc acggccttga    8100
tgatcgcggc ggccttggcc tgcatatccc gattcaacgg ccccagggcg tccagaacgg    8160
gcttcaggcg ctcccgaagg tctcgggccg tctcttgggc ttgatcggcc ttcttgcgca    8220
tctcacgcgc tcctgcggcg gcctgtaggg caggctcata ccctgccga accgcttttg    8280 tcagccggtc ggccacggct ccggcgtct caacgcgctt tgagattccc agcttttcgg    8340
ccaatccctg cggtgcatag gcgcgtggct cgaccgcttg cgggctgatg gtgacgtggc    8400
ccactggtgg ccgctccagg gcctcgtaga acgcctgaat gcgcgtgtga cgtgccttgc    8460
tgcc                                                                 8464
```

<210> SEQ ID NO 18
<211> LENGTH: 8278
<212> TYPE: DNA
<213> ORGANISM: Artificial sequence
<220> FEATURE:
<223> OTHER INFORMATION: Synthetic

<400> SEQUENCE: 18

```
ctcgatgccc cgttgcagcc ctagatcggc cacagcggcc gcaaacgtgg tctggtcgcg    60
ggtcatctgc gctttgttgc cgatgaactc cttggccgac agcctgccgt cctgcgtcag    120
cggcaccacg aacgcggtca tgtgcgggct ggtttcgtca cggtggatgc tggccgtcac    180
gatgcgatcc gccccgtact tgtccgccag ccacttgtgc gccttctcga agaacgccgc    240
ctgctgttct tggctggccg acttccacca ttccgggctg gccgtcatga cgtactcgac    300
cgccaacaca gcgtccttgc gccgcttctc tggcagcaac tcgcgcagtc ggcccatcgc    360
```

```
ttcatcggtg ctgctggccg cccagtgctc gttctctggc gtcctgctgg cgtcagcgtt      420
gggcgtctcg cgctcgcggt aggcgtgctt gagactggcc gccacgttgc ccattttcgc      480
cagcttcttg catcgcatga tcgcgtatgc cgccatgcct gccccctccct tttggtgtcc     540
aaccggctcg acggggggcag cgcaaggcgg tgcctccggc gggccactca atgcttgagt     600
atactcacta gactttgctt cgcaaagtcg tgaccgccta cggcggctgc ggcgccctac      660
gggcttgctc tccgggcttc gccctgcgcg gtcgctgcgc tcccttgcca gcccgtggat      720
atgtggacga tggccgcgag cggccaccgg ctggctcgct tcgctcggcc cgtggacaac      780
cctgctggac aagctgatgg acaggctgcg cctgcccacg agcttgacca cagggattgc      840
ccaccggcta cccagccttc gaccacatac ccaccggctc caactgcgcg gcctgcggcc      900
ttgcccccatc aattttttta attttctctg gggaaaagcc tccggcctgc ggcctgcgcg     960
cttcgcttgc cggttggaca ccaagtggaa ggcgggtcaa ggctcgcgca gcgaccgcgc     1020
agcggcttgg ccttgacgcg cctggaacga cccaagccta tgcgagtggg ggcagtcgaa     1080
ggcgaagccc gcccgcctgc cccccgagcc tcacggcggc gagtgcgggg gttccaaggg     1140
ggcagcgcca ccttgggcaa ggccgaaggc cgcgcagtcg atcaacaagc cccggagggg     1200
ccacttttttg ccggagggggg agccgcgccg aaggcgtggg ggaaccccgc aggggtgccc    1260
ttctttgggc accaaagaac tagatatagg gcgaaatgcg aaagacttaa aaatcaacaa     1320
cttaaaaaag gggggtacgc aacagctcat tgcggcaccc cccgcaatag ctcattgcgt     1380
aggttaaaga aaatctgtaa ttgactgcca cttttacgca acgcataatt gttgtcgcgc     1440
tgccgaaaag ttgcagctga ttgcgcatgg tgccgcaacc gtgcggcacc ctaccgcatg     1500
gagataagca tggccacgca gtccagagaa atcggcattc aagccaagaa caagcccggt     1560
cactgggtgc aaacggaacg caaagcgcat gaggcgtggg ccgggcttat tgcgaggaaa     1620
cccacggcgg caatgctgct gcatcacctc gtggcgcaga tgggccacca gaacgccgtg     1680
gtggtcagcc agaagacact ttccaagctc atcggacgtt ctttgcggac ggtccaatac     1740
gcagtcaagg acttggtggc cgagcgctgg atctccgtcg tgaagctcaa cggccccggc     1800
accgtgtcgg cctacgtggt caatgaccgc gtggcgtggg gccagccccg cgaccagttg     1860
cgcctgtcgg tgttcagtgc cgccgtggtg gttgatcacg acgaccagga cgaatcgctg     1920
ttggggcatg cgaccctgcg ccgcatcccg accctgtatc cggcgagca gcaactaccg      1980
accggccccg gcgaggagcc gcccagccag cccggcattc cgggcatgga accagacctg     2040
ccagccttga ccgaaacgga ggaatgggaa cggcgcgggc agcagcgcct gccgatgccc     2100
gatgagccgt gttttctgga cgatggcgag ccgttggagc cgccgacacg ggtcacgctg     2160
ccgcgccggt agcacttggg ttgcgcagca acccgtaagt gcgctgttcc agactatcgg     2220
ctgtagccgc ctctagatta attaacctcc agcgcgggga tctcatgctg gagttcttcg     2280
cccaccccca gacaagctgt gaccgtctcc gggagctgca tgtgtcagag gttttcaccg     2340
tcatcaccga aacgcgcgag gcagcagatc aattcgcgcg cgaaggcgaa gcggcatgca     2400
taatgtgcct gtcaaatgga cgaagcaggg attctgcaaa ccctatgcta ctccgtcaag     2460
ccgtcaattg tctgattcgt taccaattat gacaacttga cggctacatc attcactttt     2520
tcttcacaac cggcacggaa ctcgctcggg ctggccccgg tgcattttttt aaatacccgc    2580
gagaaataga gttgatcgtc aaaaccaaca ttgcgaccga cggtggcgat aggcatccgg     2640
gtggtgctca aaagcagctt cgcctggctg atacgttggt cctcgcgcca gcttaagacg     2700
ctaatcccta actgctggcg gaaaagatgt gacagacgcg acggcgacaa gcaaacatgc     2760
```

```
tgtgcgacgc tggcgatatc aaaattgctg tctgccaggt gatcgctgat gtactgacaa    2820
gcctcgcgta cccgattatc catcggtgga tggagcgact cgttaatcgc ttccatgcgc    2880
cgcagtaaca attgctcaag cagatttatc gccagcagct ccgaatagcg cccttcccct    2940
tgcccggcgt taatgatttg cccaaacagg tcgctgaaat gcggctggtg cgcttcatcc    3000
gggcgaaaga accccgtatt ggcaaatatt gacggccagt taagccattc atgccagtag    3060
gcgcgcggac gaaagtaaac ccactggtga taccattcgc gagcctccgg atgacgaccg    3120
tagtgatgaa tctctcctgg cgggaacagc aaaatatcac ccggtcggca aacaaattct    3180
cgtccctgat ttttcaccac cccctgaccg cgaatggtga gattgagaat ataacctttc    3240
attcccagcg gtcggtcgat aaaaaaatcg agataaccgt tggcctcaat cggcgttaaa    3300
cccgccacca gatgggcatt aaacgagtat cccggcagca gggatcatt ttgcgcttca    3360 gccatacttt tcatactccc gccattcaga aagaaaacca attgtccata ttgcatcaga    3420
cattgccgtc actgcgtctt ttactggctc ttctcgctaa ccaaaccggt aaccccgctt    3480
attaaaagca ttctgtaaca aagcgggacc aaagccatga caaaaacgcg taacaaaagt    3540
gtctataatc acggcagaaa agtccacatt gattatttgc acggcgtcac actttgctat    3600
gccatagcat ttttatccat aagattagcg gatcctacct gacgcttttt atcgcaactc    3660
tctactgttt ctccataccc gtttttttggg ctagaaataa ttttgagctc gccaaggaga    3720
tataatgact gccgacaaca atagtatgcc ccatggtgca gtatctagtt acgccaaatt    3780
agtgcaaaac caaacacctg aagcattttt ggaagagttt cctgaaatta ttccattaca    3840
acaaagacct aatacccgat ctagtgagac gtcaaatgac gaaagcggag aaacatgttt    3900
ttctggtcat gatgaggagc aaattaagtt aatgaatgaa aattgtattg ttttggattg    3960
ggacgataat gctattggtg ccggtaccaa gaaagtttgt catttaatgg aaaatattga    4020
aaagggttta ctacatcgtg cattctccgt ctttattttc aatgaacaag gtgaattact    4080
tttacaacaa agagccactg aaaaaataac tttccctgat ctttggacta acacatgctg    4140
ctctcatcca ctatgtattg atgacgaatt aggtttgaag ggtaagctag acgataagat    4200
taagggcgct attactgcgg cggtgagaaa actagatcat gaattaggta ttccagaaga    4260
tgaaactaag acaaggggta agtttcactt tttaaacaga atccattaca tggcaccaag    4320
caatgaacca tggggtgaac atgaaattga ttacatccta ttttataaga tcaacgctaa    4380
agaaaacttg actgtcaacc caaacgtcaa tgaagttaga gacttcaaat gggtttcacc    4440
aaatgatttg aaaactatgt ttgctgaccc aagttacaag tttacgcctt ggtttaagat    4500
tatttgcgag aattacttat tcaactggtg ggagcaatta gatgaccttt ctgaagtgga    4560
aaatgacagg caaattcata gaatgctata actttaagga aggagcgaag catgcgttgt    4620
agcgttagca ccgaaaatgt gtcgtttacg gaaacggaaa ccgaagctcg ccgcagcgca    4680
aactatgaac cgaactcgtg ggattacgat tacctcctta gcagcgatac ggatgaaagc    4740
attgaagtgt ataaagacaa agccaagaaa ctggaggccg aagtccgtcg cgaaatcaac    4800
aatgagaaag cggagtttct tacgttactg gaattgatcg ataacgtgca acggttaggc    4860
ctcggctacc gctttgagag cgatatccgt ggtgcactgg accgcttcgt atcgtctggt    4920
ggttttgacg ccgttacgaa aacgagcctg catggtacag cattgtcttt tcggctgttg    4980
cgccagcatg gatttgaagt gtcacaggag gcattttcag gcttcaaaga ccagaacggg    5040 aatttttttgg agaatttgaa agaagatatc aaagcgatct tatctctgta tgaggcgtca    5100
```

```
tttctcgctc tggaagggga aaatattctg gacgaagcga aagtgttcgc aatttcccat    5160
ctgaaagaac tttccgaaga aaagattggg aaagaattgg ccgaacaggt gaaccatgcg    5220
ctggaactgc cactgcaccg tcgcacccaa cgcctcgaag cggtatggtc gattgaagcg    5280
tatcgcaaaa aagaggatgc aaatcaggtt ctgctggaac tggccattct cgactataac    5340
atgattcagt ccgtctatca acgtgatctg cgcgaaacta gtcgttggtg gcgccgtgta    5400
ggacttgcca ctaaactgca ttttgcacgt gatcgtctga ttgagtcgtt ctattgggcg    5460
gttggtgtag cgtttgagcc gcagtattct gattgccgca atagtgtggc gaaaatgttc    5520
tcctttgtga ccatcattga cgatatttac gacgtgtatg gcaccctgga tgaactggaa    5580
ttattcaccg atgcagtaga acgctgggac gtcaacgcga tcaatgattt gccggattac    5640
atgaaactgt gttttctggc cctgtataac accattaacg aaattgccta tgacaacctc    5700
aaagacaagg gtgaaaatat cctgccctat ctgactaaag cttgggctga tctgtgtaac    5760
gcgttcttac aggaagccaa atggctctac aacaagagta cgcctacttt cgatgactac    5820
tttggcaacg cttggaaaag ctctagcggc cctttacaac tggtgttcgc gtatttcgcc    5880
gttgttcaga atatcaagaa agaagagatt gagaacctcc aaaagtacca cgatacgatt    5940
tcgcgtccgt cacacatctt tcgccttrgc aatgatttgg ccagtgcatc tgcagagatt    6000
gcgcgcggtg aaactgccaa ctccgtcagt tgctacatgc gtaccaaagg catcagcgag    6060
gaactggcta ccgagtcggt gatgaactta atcgatgaaa cctggaagaa gatgaacaaa    6120
gagaaacttg gtggcagtct gtttgctaaa ccgttcgttg agacagcgat taatctggcg    6180
cgtcaaagcc actgcaccta ccacaatggc gatgcccaca catccccaga cgaattaacc    6240
cggaaacgtg tcctgagtgt catcaccgaa cccattctgc cgttcgaacg ctaagcctgc    6300
taacaaagcc cgaaaggaag ctgagttggc tgctgccacc gctgagcact agtgcggccg    6360
ctttgcgcat tcacagttct ccgcaagaat tgattggctc caattcttgg agtggtgaat    6420
ccgttagcga ggtgccgccg gcttccattc aggtcgaggt ggcccggctc catgcaccgc    6480
gacgcaacgc ggggaggcag acaaggtata gggcggcgcc tacaatccat gccaacccgt    6540
tccatgtgct cgccgaggcg gcataaatcg ccgtgacgat cagcggtcca gtgatcgaag    6600
ttaggctggt aagagccgcg agcgatcctt gaagctgtcc ctgatggtcg tcatctacct    6660
gcctggacag catggcctgc aacgcgggca tcccgatgcc gccggaagcg agaagaatca    6720
taatggggaa ggccatccag cctcgcgtcg cgaacgccag caagacgtag cccagcgcgt    6780
cggccgccat gccggcgata atggcctgct tctcgccgaa acgtttggtg gcgggaccag    6840
tgacgaaggc ttgagcgagg gcgtgcaaga ttccgaatac cgcaagcgac aggccgatca    6900
tcgtcgcgct ccagcgaaag cggtcctcgc cgaaaatgac ccagagcgct gccggcacct    6960
gtcctacgag ttgcatgata agaagacag tcataagtgc ggcgacgata gtcatgcccc    7020
gcgcccaccg gaaggagctg actgggttga aggctctcaa gggcatcggt cgacgctctc    7080
ccttatgcga ctcctgcatt aggaagcagc ccagtagtag gttgaggccg ttgagcaccg    7140
ccgccgcaag gaatggtgca tgcaaggaga tggcgcccaa cagtcccccg ccacggggc    7200 ctgccaccat acccacgccg aaacaagcgc tcatgagccc gaagtggcga gcccgatctt    7260
ccccatcggt gatgtcggcg ataggcgc cagcaaccgc acctgtggcg ccggtgatgc    7320
cggccacgat gcgtccggcg tagaggatcc acaggacggg tgtggtcgcc atgatcgcgt    7380
agtcgatagt ggctccaagt agcgaagcga gcaggactgg gcggcggcca aagcggtcgg    7440
acagtgctcc gagaacgggt gcgcatagaa attgcatcaa cgcatatagc gctagcagca    7500
```

```
cgccatagtg actggcgatg ctgtcggaat ggacgatatc ccgcaagagg cccggcagta      7560
ccggcataac caagcctatg cctacagcat ccagggtgac ggtgccgagg atgacgatga      7620
gcgcattgtt agatttcata cacggtgcct gactgcgtta gcaatttaac tgtgataaac      7680
taccgcatta aagcttatcg atgataagct gtcaaacatg agaattcttg aagacgaaag      7740
ggcctcgtga tacgcctatt tttataggtt aatgtcatga taataatggt ttcttagacg      7800
tcaggtggca cttttcgggg aaatgtgcgc ggcccgcgtt ctgctggcgc tgggcctgtt      7860
tctggcgctg gacttcccgc tgttccgtca gcagttttc gcccacggcc ttgatgatcg       7920
cggcggcctt ggcctgcata tcccgattca acggccccag ggcgtccaga acgggcttca      7980
ggcgctcccg aaggtctcgg gccgtctctt gggcttgatc ggccttcttg cgcatctcac      8040
gcgctcctgc ggcggcctgt agggcaggct catacccctg ccgaaccgct tttgtcagcc      8100
ggtcggccac ggcttccggc gtctcaacgc gctttgagat cccagctttt cggccaatc       8160 cctgcggtgc ataggcgcgt ggctcgaccc cttgcgggct gatggtgacg tggcccactg      8220
gtggccgctc cagggcctcg tagaacgcct gaatgcgcgt gtgacgtgcc ttgctgcc        8278

<210> SEQ ID NO 19
<211> LENGTH: 8455
<212> TYPE: DNA
<213> ORGANISM: Artificial sequence
<220> FEATURE:
<223> OTHER INFORMATION: Synthetic

<400> SEQUENCE: 19
ctcgatgccc cgttgcagcc ctagatcggc cacagcggcc gcaaacgtgg tctggtcgcg        60
ggtcatctgc gctttgttgc cgatgaactc cttggccgac agcctgccgt cctgcgtcag      120
cggcaccacg aacgcggtca tgtgcgggct ggtttcgtca cggtggatgc tggccgtcac      180
gatgcgatcc gccccgtact tgtccgccag ccacttgtgc gccttctcga agaacgccgc      240
ctgctgttct tggctggccg acttccacca ttccgggctg gccgtcatga cgtactcgac      300
cgccaacaca gcgtccttgc gccgcttctc tggcagcaac tcgcgcagtc ggcccatcgc      360
ttcatcggtg ctgctggccg cccagtgctc gttctctggc gtcctgctgg cgtcagcgtt      420
gggcgtctcg cgctcgcggt aggcgtgctt gagactggcc gccacgttgc ccattttcgc      480
cagcttcttg catcgcatga tcgcgtatgc cgccatgcct gcccctcct  tttggtgtcc       540 aaccggctcg acggggggcag cgcaaggcgg tgcctccggc gggccactca atgcttgagt      600
atactcacta gactttgctt cgcaaagtcg tgaccgccta cggcggctgc ggcgccctac      660
gggcttgctc tccgggcttc gccctgcgcg gtcgctgcgc tcccttgcca gcccgtggat      720
atgtggacga tggccgcgag cggccaccgg ctggctcgct tcgctcggcc cgtggacaac      780
cctgctggac aagctgatgg acaggctgcg cctgcccacg agcttgacca cagggattgc      840
ccaccggcta cccagccttc gaccacatac ccaccggctc caactgcgcg gcctgcggcc      900
ttgccccatc aatttttta atttctctg ggaaaagcc tccggcctgc ggcctgcgcg         960
cttcgcttgc cggttggaca ccaagtggaa ggcgggtcaa ggctcgcgca gcgaccgcgc      1020
agcggcttgg ccttgacgcg cctggaacga cccaagccta tgcgagtggg ggcagtcgaa      1080
ggcgaagccc gccgcctgc ccccgagcc tcacggcggc gagtgcgggg gttccaaggg       1140
ggcagcgcca ccttgggcaa ggccgaaggc cgcgcagtcg atcaacaagc ccggaggggg     1200 ccacttttg ccggagggg agccgcgccg aaggcgtggg ggaaccccgc aggggtgccc      1260
```

```
ttctttgggc accaaagaac tagatatagg gcgaaatgcg aaagacttaa aaatcaacaa    1320
cttaaaaaag gggggtacgc aacagctcat tgcggcaccc cccgcaatag ctcattgcgt    1380
aggttaaaga aaatctgtaa ttgactgcca cttttacgca acgcataatt gttgtcgcgc    1440
tgccgaaaag ttgcagctga ttgcgcatgg tgccgcaacc gtgcggcacc ctaccgcatg    1500
gagataagca tggccacgca gtccagagaa atcggcattc aagccaagaa caagcccggt    1560
cactgggtgc aaacggaacg caaagcgcat gaggcgtggg ccgggcttat tgcgaggaaa    1620
cccacggcgg caatgctgct gcatcacctc gtggcgcaga tgggccacca gaacgccgtg    1680
gtggtcagcc agaagacact ttccaagctc atcggacgtt ctttgcggac ggtccaatac    1740
gcagtcaagg acttggtggc cgagcgctgg atctccgtcg tgaagctcaa cggccccggc    1800
accgtgtcgg cctacgtggt caatgaccgc gtggcgtggg gccagccccg cgaccagttg    1860
cgcctgtcgg tgttcagtgc cgccgtggtg gttgatcacg acgaccagga cgaatcgctg    1920
ttggggcatg gcgacctgcg ccgcatcccg accctgtatc cgggcgagca gcaactaccg    1980
accggccccg gcgaggagcc gcccagccag cccggcattc cgggcatgga accagacctg    2040
ccagccttga ccgaaacgga ggaatgggaa cggcgcgggc agcagcgcct gccgatgccc    2100
gatgagccgt gttttctgga cgatggcgag ccgttggagc cgccgacacg gtcacgctg    2160 ccgcgccggt agcacttggg ttgcgcagca acccgtaagt gcgctgttcc agactatcgg    2220
ctgtagccgc ctctagatta attaacctcc agcgcgggga tctcatgctg gagttcttcg    2280
cccaccccca gacaagctgt gaccgtctcc gggagctgca tgtgtcagag gttttcaccg    2340
tcatcaccga aacgcgcgag gcagcagatc aattcgcgcg cgaaggcgaa gcggcatgca    2400
taatgtgcct gtcaaatgga cgaagcaggg attctgcaaa ccctatgcta ctccgtcaag    2460
ccgtcaattg tctgattcgt taccaattat gacaacttga cggctacatc attcactttt    2520
tcttcacaac cggcacggaa ctcgctcggg ctggccccgg tgcattttt aaatacccgc    2580 gagaaataga gttgatcgtc aaaaccaaca ttgcgaccga cggtggcgat aggcatccgg    2640
gtggtgctca aaagcagctt cgcctggctg atacgttggt cctcgcgcca gcttaagacg    2700
ctaatcccta actgctggcg gaaaagatgt gacagacgcg acggcgacaa gcaaacatgc    2760
tgtgcgacgc tggcgatatc aaaattgctg tctgccaggt gatcgctgat gtactgacaa    2820
gcctcgcgta cccgattatc catcggtgga tggagcgact cgttaatcgc ttccatgcgc    2880
cgcagtaaca attgctcaag cagatttatc gccagcagct ccgaatagcg cccttcccct    2940
tgcccggcgt taatgatttg cccaaacagg tcgctgaaat gcggctggtg cgcttcatcc    3000
gggcgaaaga accccgtatt ggcaaatatt gacggccagt taagccattc atgccagtag    3060
gcgcgcggac gaaagtaaac ccactggtga taccattcgc gagcctccgg atgacgaccg    3120
tagtgatgaa tctctcctgg cgggaacagc aaaatatcac ccggtcggca aacaaattct    3180
cgtccctgat ttttcaccac cccctgaccg cgaatggtga gattgagaat ataacctttc    3240
attcccagcg gtcggtcgat aaaaaaatcg agataaccgt tggcctcaat cggcgttaaa    3300
cccgccacca gatgggcatt aaacgagtat cccggcagca ggggatcatt ttgcgcttca    3360
gccatacttt tcatactccc gccattcaga gaagaaacca attgtccata ttgcatcaga    3420
cattgccgtc actgcgtctt ttactggctc ttctcgctaa ccaaaccggt aaccccgctt    3480
attaaaagca ttctgtaaca aagcgggacc aaagccatga caaaaacgcg taacaaaagt    3540
gtctataatc acggcagaaa agtccacatt gattatttgc acggcgtcac actttgctat    3600
gccatagcat ttttatccat aagattagcg gatcctacct gacgcttttt atcgcaactc    3660
```

```
tctactgttt ctccataccc gttttttggg ctagaaataa ttttgagctc gccaaggaga    3720
tataatgaat cgaaaagatg aacatctatc attagctaaa gcgttccaca aagaaaaaag    3780
taatgacttt gatcgtgtgc gttttgttca ccaatcgttt gctgaatccg ctgttaacga    3840
agtggatatt tccacttcgt ttctttcttt tcagcttccc caaccttttt atgtcaatgc    3900
aatgacaggt ggtagtcagc gtgcaaaaga aattaatcag caattaggca ttattgccaa    3960
agaaactggc cttttagttg cgacaggatc tgtctcggca gcgttaaaag atgctagttt    4020
agcggatacg tatcaaatta tgcgaaaaga aaacccagat ggactcattt ttgccaatat    4080
tggtgcaggc ttgggtgtgg aagaagcaaa gcgagcgctt gatttatttc aagcgaatgc    4140
cttacaaatc catgtaaatg tgccccaaga attggtcatg cctgaaggag atcgtgattt    4200
cactaattgg ctaaccaaga ttgaagctat cgtacaggcc gtagaagtgc ctgtcattgt    4260
caaagaggtt ggctttggca tgagccaaga aaccttagaa aaacttacct ctatcggcgt    4320
tcaagcagcg gatgtgagcg gccaaggcgg aacgagtttt acacaaattg aaaatgcccg    4380
gcggaagaaa cgagaacttt cttcttaga tgattggggg caatcaacgg tcatctctct    4440
tctggaatca caaaattggc aaaagaaact aactattctc ggctctggcg gtgtgcgtaa    4500
ctctcttgat attgtcaaag gactcgcttt aggtgccaaa agcatgggag ttgctgggac    4560
tatcttagct tcccttatga gtaaaaatgg tttagaaaat accttagccc ttgtacagca    4620
atggcaagaa gaagtgaaaa tgctttatac tcttttagga aaaagacga cagaagaatt    4680 gacgagtacc gcacttgtcc tcgatccagt tttagttaat tggtgtcata ccgtgggtat    4740
cgacagcact gttttcgcaa aacgttaact ttaaggaagg agcgaagcat gcgttgtagc    4800
gttagcaccg aaaatgtgtc gtttacggaa acggaaaccg aagctcgccg cagcgcaaac    4860
tatgaaccga actcgtggga ttacgattac ctccttagca gcgatacgga tgaaagcatt    4920
gaagtgtata aagacaaagc caagaaactg gaggccgaag tccgtcgcga aatcaacaat    4980
gagaaagcgg agtttcttac gttactggaa ttgatcgata acgtgcaacg gttaggcctc    5040
ggctaccgct ttgagagcga tatccgtggt gcactggacc gcttcgtatc gtctggtggt    5100
tttgacgccg ttacgaaaac gagcctgcat ggtacagcat tgtcttttcg gctgttgcgc    5160
cagcatggat ttgaagtgtc acaggaggca ttttcaggct tcaaagacca gaacgggaat    5220
tttttggaga atttgaaaga agatatcaaa gcgatcttat ctctgtatga ggcgtcattt    5280
ctcgctctgg aaggggaaaa tattctggac gaagcgaaag tgttcgcaat ttcccatctg    5340
aaagaacttt ccgaagaaaa gattgggaaa gaattggccg aacaggtgaa ccatgcgctg    5400
gaactgccac tgcaccgtcg cacccaacgc ctcgaagcgg tatggtcgat tgaagcgtat    5460
cgcaaaaaag aggatgcaaa tcaggttctg ctggaactgg ccattctcga ctataacatg    5520
attcagtccg tctatcaacg tgatctgcgc gaaactagtc gttggtggcg ccgtgtagga    5580
cttgccacta aactgcattt tgcacgtgat cgtctgattg agtcgttcta ttgggcggtt    5640
ggtgtagcgt ttgagccgca gtattctgat tgccgcaata gtgtggcgaa aatgttctcc    5700
tttgtgacca tcattgacga tatttacgac gtgtatggca ccctggatga actggaatta    5760
ttcaccgatg cagtagaacg ctgggacgtc aacgcgatca atgatttgcc ggattacatg    5820
aaactgtgtt ttctggccct gtataacacc attaacgaaa ttgcctatga caacctcaaa    5880
gacaagggtg aaaatatcct gcccctatctg actaaagctt gggctgatct gtgtaacgcg    5940
ttcttacagg aagccaaatg gctctacaac aagagtacgc ctactttcga tgactacttt    6000
```

```
ggcaacgctt ggaaaagctc tagcggccct ttacaactgg tgttcgcgta tttcgccgtt    6060
gttcagaata tcaagaaaga agagattgag aacctccaaa agtaccacga tacgatttcg    6120
cgtccgtcac acatctttcg cctttgcaat gatttggcca gtgcatctgc agagattgcg    6180
cgcggtgaaa ctgccaactc cgtcagttgc tacatgcgta ccaaaggcat cagcgaggaa    6240
ctggctaccg agtcggtgat gaacttaatc gatgaaacct ggaagaagat gaacaaagag    6300
aaacttggtg gcagtctgtt tgctaaaccg ttcgttgaga cagcgattaa tctgcgcgt    6360 caaagccact gcacctacca caatggcgat gcccacacat ccccagacga attaacccgg    6420
aaacgtgtcc tgagtgtcat caccgaaccc attctgccgt tcgaacgcta agcctgctaa    6480
caaagcccga aggaagctg agttggctgc tgccaccgct gagcactagt gcggccgctt    6540
tgcgcattca cagttctccg caagaattga ttggctccaa ttcttggagt ggtgaatccg    6600
ttagcgaggt gccgccggct tccattcagg tcgaggtggc ccggctccat gcaccgcgac    6660
gcaacgcggg gaggcagaca aggtataggg cggcgcctac aatccatgcc aacccgttcc    6720
atgtgctcgc cgaggcggca taaatcgccg tgacgatcag cggtccagtg atcgaagtta    6780
ggctggtaag agccgcgagc gatccttgaa gctgtccctg atggtcgtca tctacctgcc    6840
tggacagcat ggcctgcaac gcgggcatcc cgatgccgcc ggaagcgaga agaatcataa    6900
tggggaaggc catccagcct cgcgtcgcga acgccagcaa gacgtagccc agcgcgtcgg    6960
ccgccatgcc ggcgataatg gcctgcttct cgccgaaacg tttggtggcg ggaccagtga    7020
cgaaggcttg agcgagggcg tgcaagattc cgaataccgc aagcgacagg ccgatcatcg    7080
tcgcgctcca gcgaaagcgg tcctcgccga aaatgaccca gagcgctgcc ggcacctgtc    7140
ctacgagttg catgataaag aagacagtca taagtgcggc gacgatagtc atgccccgcg    7200
cccaccggaa ggagctgact gggttgaagg ctctcaaggg catcggtcga cgctctccct    7260
tatgcgactc ctgcattagg aagcagccca gtagtaggtt gaggccgttg agcaccgccg    7320
ccgcaaggaa tggtgcatgc aaggagatgg cgcccaacag tccccggcc acggggcctg    7380 ccaccatacc cacgccgaaa caagcgctca tgagcccgaa gtggcgagcc cgatcttccc    7440
catcggtgat gtcggcgata taggcgccag caaccgcacc tgtggcgccg gtgatgccgg    7500
ccacgatgcg tccggcgtag aggatccaca ggacgggtgt ggtcgccatg atcgcgtagt    7560
cgatagtggc tccaagtagc gaagcgagca ggactgggcg gcggccaaag cggtcggaca    7620
gtgctccgag aacgggtgcg catagaaatt gcatcaacgc atatagcgct agcagcacgc    7680
catagtgact ggcgatgctg tcggaatgga cgatatcccg caagaggccc ggcagtaccg    7740
gcataaccaa gcctatgcct acagcatcca gggtgacggt gccgaggatg acgatgagcg    7800
cattgttaga tttcatacac ggtgcctgac tgcgttagca attaactgt gataaactac    7860 cgcattaaag cttatcgatg ataagctgtc aaacatgaga attcttgaag acgaaagggc    7920
ctcgtgatac gcctattttt ataggttaat gtcatgataa taatggtttc ttagacgtca    7980
ggtggcactt ttcggggaaa tgtgcgcgcc gcgttcctg ctggcgctgg gcctgtttct    8040
ggcgctggac ttcccgctgt tccgtcagca gcttttcgcc cacggccttg atgatcgcgg    8100
cggccttggc ctgcatatcc cgattcaacg gccccagggc gtccagaacg gcttcaggc    8160 gctcccgaag gtctcgggcc gtctcttggg cttgatcggc cttcttgcgc atctcacgcg    8220
ctcctgcgcg ggcctgtagg gcaggctcat acccctgccg aaccgctttt gtcagccggt    8280
cggccacggc ttccggcgtc tcaacgcgct ttgagattcc cagcttttcg gccaatccct    8340
gcggtgcata ggcgcgtggc tcgaccgctt gcgggctgat ggtgacgtgg cccactggtg    8400
```
gccgctccag ggcctcgtag aacgcctgaa tgcgcgtgtg acgtgccttg ctgcc    8455

<210> SEQ ID NO 20
<211> LENGTH: 8400
<212> TYPE: DNA
<213> ORGANISM: Artificial sequence
<220> FEATURE:
<223> OTHER INFORMATION: Synthetic

<400> SEQUENCE: 20
ctcgatgccc cgttgcagcc ctagatcggc cacagcggcc gcaaacgtgg tctggtcgcg      60
ggtcatctgc gctttgttgc cgatgaactc cttggccgac agcctgccgt cctgcgtcag     120
cggcaccacg aacgcggtca tgtgcgggct ggtttcgtca cggtggatgc tggccgtcac     180
gatgcgatcc gccccgtact tgtccgccag ccacttgtgc gccttctcga agaacgccgc     240
ctgctgttct tggctggccg acttccacca ttccgggctg gccgtcatga cgtactcgac     300
cgccaacaca cgtccttgc gccgcttctc tggcagcaac tcgcgcagtc ggcccatcgc     360
ttcatcggtg ctgctggccg cccagtgctc gttctctggc gtcctgctgg cgtcagcgtt     420
gggcgtctcg cgctcgcggt aggcgtgctt gagactggcc gccacgttgc ccattttcgc     480
cagcttcttg catcgcatga tcgcgtatgc cgccatgcct gcccctccct tttggtgtcc     540
aaccggctcg acggggcag cgcaaggcgg tgcctccggc gggccactca atgcttgagt     600
atactcacta gactttgctt cgcaaagtcg tgaccgccta cggcggctgc ggcgccctac     660
gggcttgctc tccgggcttc gcctgcgcg gtcgctgcgc tcccttgcca gcccgtggat     720
atgtggacga tggccgcgag cggccaccgg ctggctcgct tcgctcggcc cgtggacaac     780
cctgctggac aagctgatgg acaggctgcg cctgcccacg agcttgacca cagggattgc     840
ccaccggcta cccagccttc gaccacatac ccaccggctc caactgcgcg gcctgcggcc     900
ttgccccatc aattttttta attttctctg gggaaaagcc tccggcctgc ggcctgcgcg     960
cttcgcttgc cggttggaca ccaagtggaa ggcgggtcaa ggctcgcgca gcgaccgcgc    1020
agcggcttgg ccttgacgcg cctggaacga cccaagccta tgcgagtggg ggcagtcgaa    1080
ggcgaagccc gcccgcctgc cccccgagcc tcacggcggc gagtgcgggg gttccaaggg    1140
ggcagcgcca ccttgggcaa ggccgaaggc cgcgcagtcg atcaacaagc cccggagggg    1200
ccacttttg ccggaggggg agccgcgccg aaggcgtggg ggaaccccgc aggggtgccc    1260
ttctttgggc accaaagaac tagatatagg gcgaaatgcg aaagacttaa aaatcaacaa    1320
cttaaaaaag gggggtacgc aacagctcat tgcggcaccc cccgcaatag ctcattgcgt    1380
aggttaaaga aaatctgtaa ttgactgcca cttttacgca acgcataatt gttgtcgcgc    1440
tgccgaaaag ttgcagctga ttgcgcatgg tgccgcaacc gtgcggcacc ctaccgcatg    1500
gagataagca tggccacgca gtccagagaa atcggcattc aagccaagaa caagcccggt    1560
cactgggtgc aaacgaacg caaagcgcat gaggcgtggg ccgggcttat tgcgaggaaa    1620
cccacggcgg caatgctgct gcatcacctc gtggcgcaga tgggccacca gaacgccgtg    1680
gtggtcagcc agaagacact ttccaagctc atcggacgtt cttttgcggac ggtccaatac    1740
gcagtcaagg acttggtggc cgagcgctgg atctccgtcg tgaagctcaa cggccccggc    1800
accgtgtcgg cctacgtggt caatgaccgc gtggcgtggg ccagccccg cgaccagttg    1860
cgcctgtcgg tgttcagtgc cgccgtggtg gttgatcacg acgaccagga cgaatcgctg    1920
ttggggcatg gcgacctgcg ccgcatcccg accctgtatc cgggcgagca gcaactaccg    1980

```
accggccccg gcgaggagcc gcccagccag cccggcattc cggcatgga accagacctg    2040 ccagccttga ccgaaacgga ggaatgggaa cggcgcgggc agcagcgcct gccgatgccc    2100
gatgagccgt gttttctgga cgatggcgag ccgttggagc cgccgacacg ggtcacgctg    2160
ccgcgccggt agcacttggg ttgcgcagca acccgtaagt gcgctgttcc agactatcgg    2220
ctgtagccgc ctctagatta attaacctcc agcgcgggga tctcatgctg gagttcttcg    2280 cccacccca gacaagctgt gaccgtctcc gggagctgca tgtgtcagag gttttcaccg    2340
tcatcaccga aacgcgcgag gcagcagatc aattcgcgcg cgaaggcgaa gcggcatgca    2400
taatgtgcct gtcaaatgga cgaagcaggg attctgcaaa ccctatgcta ctccgtcaag    2460
ccgtcaattg tctgattcgt taccaattat gacaacttga cggctacatc attcacttttt    2520 tcttcacaac cggcacggaa ctcgctcggg ctggccccgg tgcattttt aaatacccgc    2580 gagaaataga gttgatcgtc aaaaccaaca ttgcgaccga cggtggcgat aggcatccgg    2640
gtggtgctca aaagcagctt cgcctggctg atacgttggt cctcgcgcca gcttaagacg    2700 ctaatccca actgctggcg gaaaagatgt gacagacgcg acggcgacaa gcaaacatgc    2760
tgtgcgacgc tggcgatatc aaaattgctg tctgccaggt gatcgctgat gtactgacaa    2820
gcctcgcgta cccgattatc catcggtgga tggagcgact cgttaatcgc ttccatgcgc    2880
cgcagtaaca attgctcaag cagatttatc gccagcagct ccgaatagcg cccttcccct    2940
tgcccggcgt taatgatttg cccaaacagg tcgctgaaat gcggctggtg cgcttcatcc    3000
gggcgaaaga accccgtatt ggcaaatatt gacggccagt taagccattc atgccagtag    3060
gcgcgcggac gaaagtaaac ccactggtga taccattcgc gagcctccgg atgacgaccg    3120
tagtgatgaa tctctcctgg cgggaacagc aaaatatcac ccgtcggca aacaaattct    3180 cgtccctgat ttttcaccac cccctgaccg cgaatggtga gattgagaat ataacctttc    3240
attcccagcg gtcggtcgat aaaaaaatcg agataaccgt tggcctcaat cggcgttaaa    3300
cccgccacca gatgggcatt aaacgagtat cccggcagca gggatcatt ttgcgcttca    3360 gccatacttt tcatactccc gccattcaga gaagaaacca attgtccata ttgcatcaga    3420
cattgccgtc actgcgtctt ttactggctc ttctcgctaa ccaaaccggt aaccccgctt    3480
attaaaagca ttctgtaaca agcgggacc aaagccatga caaaaacgcg taacaaaagt    3540
gtctataatc acggcagaaa agtccacatt gattatttgc acggcgtcac actttgctat    3600
gccatagcat ttttatccat aagattagcg gatcctacct gacgctttt atcgcaactc    3660 tctactgttt ctccatacc gtttttggg ctagaaataa ttttgagctc gccaaggaga    3720
tataatgact aaccgtaaag atgatcacat caaatatgct ctcaagtacc aatcgcctta    3780
taatgctttt gatgacatag aactcataca ccattcctta cctagctatg atttgtctga    3840
tattgatctc agtactcatt tgctgggca agacttcgac tttcccttttt acatcaatgc    3900 catgacagga ggaagtcaaa aaggcaaagc tgtcaatgaa aaattggcca agtagcagc    3960 agcaacaggg attgtcatgg tgacagggtc ttatagcgct gctttaaaaa atcctaacga    4020
cgattcctat cgtttacatg aggtggcaga taacttgaaa ctagccacga atattggtct    4080
agataaacct gtggcgctag acaacaaac ggttcaagaa atgcagcccc tcttttttaca    4140 ggttcatgtg aatgtgatgc aagagttgct gatgccagag ggtgagcgcg tctttcatac    4200
ctggaaaaaa cacctcgctg aatacgctag tcaaatacca gttcctgtca ttctcaaaga    4260
agttggtttt ggcatggatg tcaatagtat caagctagca catgacctag gcattcaaac    4320 cttttgatatt tcaggtagag gaggaacttc atttgcttac attgaaaatc aaagagggg    4380
```

```
agaccgctct tacttaaacg attggggaca aaccactgtt cagtgcttac tgaatgcaca    4440
aggactgatg gaccaagtgg aaatcttagc ttcgggtggt gtcagacacc ccttggacat    4500
gattaagtgt tttgtcttag gagcacgtgc agtgggactc tcacgcaccg ttttagaatt    4560
ggtcgaaaaa tacccaaccg agcgtgtgat tgctatcgtt aatggctgga agaagaatt     4620 aaaaatcatt atgtgtgctc ttgactgtaa aactattaaa gaattaaagg gagtcgacta    4680
cttactatat ggacgcttgc agcaggtcaa ttagcttaag gaaggagcga agcatgcgtt    4740
gtagcgttag caccgaaaat gtgtcgttta cggaaacgga aaccgaagct cgccgcagcg    4800
caaactatga accgaactcg tgggattacg attacctcct tagcagcgat acggatgaaa    4860
gcattgaagt gtataaagac aaagccaaga aactggaggc cgaagtccgt cgcgaaatca    4920
acaatgagaa agcggagttt cttacgttac tggaattgat cgataacgtg caacggttag    4980
gcctcggcta ccgctttgag agcgatatcc gtggtgcact ggaccgcttc gtatcgtctg    5040
gtggttttga cgccgttacg aaaacgagcc tgcatggtac agcattgtct tttcggctgt    5100
tgcgccagca tggatttgaa gtgtcacagg aggcattttc aggcttcaaa gaccagaacg    5160 ggaattttt ggagaatttg aaagaagata tcaaagcgat cttatctctg tatgaggcgt     5220
catttctcgc tctggaaggg gaaaatattc tggacgaagc gaaagtgttc gcaatttccc    5280
atctgaaaga acttttccgaa gaaaagattg ggaaagaatt ggccgaacag gtgaaccatg   5340
cgctggaact gccactgcac cgtcgcaccc aacgcctcga agcggtatgg tcgattgaag    5400
cgtatcgcaa aaaagaggat gcaaatcagg ttctgctgga actggccatt ctcgactata    5460
acatgattca gtccgtctat caacgtgatc tgcgcgaaac tagtcgttgg tggcgccgtg    5520
taggacttgc cactaaactg cattttgcac gtgatcgtct gattgagtcg ttctattggg    5580
cggttggtgt agcgtttgag ccgcagtatt ctgattgccg caatagtgtg gcgaaaatgt    5640
tctcctttgt gaccatcatt gacgatattt acgacgtgta tggcaccctg gatgaactgg    5700
aattattcac cgatgcagta aacgctgggg acgtcaacgc gatcaatgat ttgccggatt    5760
acatgaaact gtgttttctg gccctgtata acaccattaa cgaaattgcc tatgacaacc    5820
tcaaagacaa gggtgaaaat atcctgccct atctgactaa agcttgggct gatctgtgta    5880
acgcgttctt acaggaagcc aaatggctct acaacaagag tacgcctact ttcgatgact    5940
actttggcaa cgcttggaaa agctctagcg gccctttaca actggtgttc gcgtatttcg    6000
ccgttgttca gaatatcaag aaagaagaga ttgagaacct ccaaaagtac cacgatacga    6060
tttcgcgtcc gtcacacatc tttcgccttt gcaatgattt ggccagtgca tctgcagaga    6120
ttgcgcgcgg tgaaactgcc aactccgtca gttgctacat gcgtaccaaa ggcatcagcg    6180
aggaactggc taccgagtcg gtgatgaact taatcgatga aacctggaag aagatgaaca    6240
aagagaaact tggtggcagt ctgtttgcta aaccgttcgt tgagacagcg attaatctgg    6300
cgcgtcaaag ccactgcacc taccacaatg gcgatgccca cacatcccca gacgaattaa    6360
cccggaaacg tgtcctgagt gtcatcaccg aacccattct gccgttcgaa cgctaagcct    6420
gctaacaaag cccgaaagga agctgagttg gctgctgcca ccgctgagca ctagtgcggc    6480
cgctttgcgc attcacagtt ctccgcaaga attgattggc tccaattctt ggagtggtga    6540
atccgttagc gaggtgccgc cggcttccat tcaggtcgag gtggcccggc tccatgcacc    6600
gcgacgcaac gcggggaggc agacaaggta tagggcggcg cctacaatcc atgccaaccc    6660
gttccatgtg ctcgccgagg cggcataaat cgccgtgacg atcagcggtc cagtgatcga    6720
```

```
agttaggctg gtaagagccg cgagcgatcc ttgaagctgt ccctgatggt cgtcatctac    6780
ctgcctggac agcatggcct gcaacgcggg catcccgatg ccgccggaag cgagaagaat    6840
cataatgggg aaggccatcc agcctcgcgt cgcgaacgcc agcaagacgt agcccagcgc    6900
gtcggccgcc atgccggcga taatggcctg cttctcgccg aaacgtttgg tggcgggacc    6960
agtgacgaag gcttgagcga gggcgtgcaa gattccgaat accgcaagcg acaggccgat    7020
catcgtcgcg ctccagcgaa agcggtcctc gccgaaaatg acccagagcg ctgccggcac    7080
ctgtcctacg agttgcatga taaagaagac agtcataagt gcggcgacga tagtcatgcc    7140
ccgcgcccac cggaaggagc tgactgggtt gaaggctctc aagggcatcg gtcgacgctc    7200
tcccttatgc gactcctgca ttaggaagca gcccagtagt aggttgaggc cgttgagcac    7260
cgccgccgca aggaatggtg catgcaagga gatggcgccc aacagtcccc cggcacgggg    7320
gcctgccacc atacccacgc cgaaacaagc gctcatgagc ccgaagtggc gagcccgatc    7380
ttccccatcg gtgatgtcgg cgatataggc gccagcaacc gcacctgtgg cgccggtgat    7440
gccggccacg atgcgtccgg cgtagaggat ccacaggacg ggtgtggtcg ccatgatcgc    7500
gtagtcgata gtggctccaa gtagcgaagc gagcaggact gggcggcggc caaagcggtc    7560
ggacagtgct ccgagaacgg gtgcgcatag aaattgcatc aacgcatata gcgctagcag    7620
cacgccatag tgactggcga tgctgtcgga atggacgata tcccgcaaga ggcccggcag    7680
taccggcata accaagccta tgcctacagc atccagggtg acggtgccga ggatgacgat    7740
gagcgcattg ttagatttca tacacggtgc ctgactgcgt tagcaattta actgtgataa    7800
actaccgcat taaagcttat cgatgataag ctgtcaaaca tgagaattct tgaagacgaa    7860
agggcctcgt gatacgccta ttttatagg ttaatgtcat gataataatg gtttcttaga    7920
cgtcaggtgg cacttttcgg ggaaatgtgc gcgcccgcgt tcctgctggc gctgggcctg    7980
tttctggcgc tggacttccc gctgttccgt cagcagcttt cgcccacgg ccttgatgat    8040
cgcggcggcc ttggcctgca tatcccgatt caacggcccc agggcgtcca gaacgggctt    8100
caggcgctcc cgaaggtctc gggccgtctc ttgggcttga tcggccttct tgcgcatctc    8160
acgcgctcct gcgcggcct gtagggcagg ctcatacccc tgccgaaccg cttttgtcag    8220
ccggtcggcc acggcttccg gcgtctcaac gcgctttgag attcccagct tttcggccaa    8280
tccctgcggt gcataggcgc gtggctcgac cgcttgcggg ctgatggtga cgtgccccac    8340
tggtggccgc tccagggcct cgtagaacgc ctgaatgcgc gtgtgacgtg ccttgctgcc    8400
```

<210> SEQ ID NO 21
<211> LENGTH: 8443
<212> TYPE: DNA
<213> ORGANISM: Artificial sequence
<220> FEATURE:
<223> OTHER INFORMATION: Synthetic

<400> SEQUENCE: 21

```
ctcgatgccc cgttgcagcc ctagatcggc cacagcggcc gcaaacgtgg tctggtcgcg      60
ggtcatctgc gctttgttgc cgatgaactc cttggccgac agcctgccgt cctgcgtcag     120
cggcaccacg aacgcggtca tgtgcgggct ggtttcgtca cggtggatgc tggccgtcac     180
gatgcgatcc gccccgtact tgtccgccag ccacttgtgc gccttctcga agaacgccgc     240
ctgctgttct tggctggccg acttccacca ttccgggctg ccgtcatga cgtactcgac     300
cgccaacaca gcgtccttgc gccgcttctc tggcagcaac tcgcgcagtc ggcccatcgc     360
ttcatcggtg ctgctggccg cccagtgctc gttctctggc gtcctgctgg cgtcagcgtt     420
```

```
gggcgtctcg cgctcgcggt aggcgtgctt gagactggcc gccacgttgc ccattttcgc    480
cagcttcttg catcgcatga tcgcgtatgc cgccatgcct gcccctccct tttggtgtcc    540
aaccggctcg acgggggcag cgcaaggcgg tgcctccggc gggccactca atgcttgagt    600
atactcacta gactttgctt cgcaaagtcg tgaccgccta cggcggctgc ggcgccctac    660
gggcttgctc tccgggcttc gccctgcgcg gtcgctgcgc tcccttgcca gcccgtggat    720
atgtggacga tggccgcgag cggccaccgg ctggctcgct tcgctcggcc cgtggacaac    780
cctgctggac aagctgatgg acaggctgcg cctgcccacg agcttgacca cagggattgc    840
ccaccggcta cccagccttc gaccacatac ccaccggctc caactgcgcg gcctgcggcc    900
ttgccccatc aattttttta attttctctg gggaaaagcc tccggcctgc ggcctgcgcg    960
cttcgcttgc cggttggaca ccaagtggaa ggcgggtcaa ggctcgcgca gcgaccgcgc   1020
agcggcttgg ccttgacgcg cctggaacga cccaagccta tgcgagtggg ggcagtcgaa   1080
ggcgaagccc gcccgcctgc cccccgagcc tcacggcggc gagtgcgggg gttccaaggg   1140
ggcagcgcca ccttgggcaa ggccgaaggc cgcgcagtcg atcaacaagc cccggagggg   1200
ccactttttg ccggaggggg agccgcgccg aaggcgtggg ggaacccgc aggggtgccc   1260 ttctttgggc accaaagaac tagatatagg gcgaaatgcg aaagacttaa aaatcaacaa   1320
cttaaaaaag gggggtacgc aacagctcat tgcggcaccc cccgcaatag ctcattgcgt   1380
aggttaaaga aaatctgtaa ttgactgcca cttttacgca acgcataatt gttgtcgcgc   1440
tgccgaaaag ttgcagctga ttgcgcatgg tgccgcaacc gtgcggcacc ctaccgcatg   1500
gagataagca tggccacgca gtccagagaa atcggcattc aagccaagaa caagcccggt   1560
cactgggtgc aaacggaacg caaagcgcat gaggcgtggg ccgggcttat tgcgaggaaa   1620
cccacggcgg caatgctgct gcatcacctc gtggcgcaga tgggccacca gaacgccgtg   1680
gtggtcagcc agaagacact ttccaagctc atcggacgtt ctttgcggac ggtccaatac   1740
gcagtcaagg acttggtggc cgagcgctgg atctccgtcg tgaagctcaa cggccccggc   1800
accgtgtcgg cctacgtggt caatgaccgc gtggcgtggg gccagccccg cgaccagttg   1860
cgcctgtcgg tgttcagtgc cgccgtggtg gttgatcacg acgaccagga cgaatcgctg   1920
ttggggcatg gcgacctgcg ccgcatcccg accctgtatc cgggcgagca gcaactaccg   1980
accggccccg cgaggagcc gcccagccag cccggcattc cgggcatgga accagacctg   2040
ccagccttga ccgaaacgga ggaatgggaa cggcgcgggc agcagcgcct gccgatgccc   2100
gatgagccgt gttttctgga cgatggcgag ccgttggagc cgccgacacg ggtcacgctg   2160
ccgcgccggt agcacttggg ttgcgcagca acccgtaagt gcgctgttcc agactatcgg   2220
ctgtagccgc ctctagatta attaacctcc agcgcgggga tctcatgctg gagttcttcg   2280
cccaccccca gacaagctgt gaccgtctcc gggagctgca tgtgtcagag gttttcaccg   2340
tcatcaccga aacgcgcgag gcagcagatc aattcgcgcg cgaaggcgaa gcggcatgca   2400
taatgtgcct gtcaaatgga cgaagcaggg attctgcaaa ccctatgcta ctccgtcaag   2460
ccgtcaattg tctgattcgt taccaattat gacaacttga cggctacatc attcactttt   2520
tcttcacaac cggcacggaa ctcgctcggg ctggccccgg tgcattttttt aaatacccgc   2580 gagaaataga gttgatcgtc aaaaccaaca ttgcgaccga cggtggcgat aggcatccgg   2640
gtggtgctca aaagcagctt cgcctggctg atacgttggt cctcgcgcca gcttaagacg   2700
ctaatcccta actgctggcg gaaaagatgt gacagacgcg acggcgacaa gcaaacatgc   2760
```

-continued

```
tgtgcgacgc tggcgatatc aaaattgctg tctgccaggt gatcgctgat gtactgacaa      2820
gcctcgcgta cccgattatc catcggtgga tggagcgact cgttaatcgc ttccatgcgc      2880
cgcagtaaca attgctcaag cagatttatc gccagcagct ccgaatagcg cccttcccct      2940
tgcccggcgt taatgatttg cccaaacagg tcgctgaaat gcggctggtg cgcttcatcc      3000
gggcgaaaga accccgtatt ggcaaatatt gacggccagt taagccattc atgccagtag      3060
gcgcgcggac gaaagtaaac ccactggtga taccattcgc gagcctccgg atgacgaccg      3120
tagtgatgaa tctctcctgg cgggaacagc aaaatatcac ccggtcggca aacaaattct      3180
cgtccctgat ttttcaccac cccctgaccg cgaatggtga gattgagaat ataacctttc      3240
attcccagcg gtcggtcgat aaaaaaatcg agataaccgt tggcctcaat cggcgttaaa      3300
cccgccacca gatgggcatt aaacgagtat cccggcagca gggatcatt ttgcgcttca      3360 gccatacttt tcatactccc gccattcaga gaagaaacca attgtccata ttgcatcaga      3420
cattgccgtc actgcgtctt ttactggctc ttctcgctaa ccaaaccggt aaccccgctt      3480
attaaaagca ttctgtaaca aagcgggacc aaagccatga caaaaacgcg taacaaaagt      3540
gtctataatc acggcagaaa agtccacatt gattatttgc acggcgtcac actttgctat      3600
gccatagcat ttttatccat aagattacg gatcctacct gacgctttt atcgcaactc       3660 tctactgttt ctccataccc gtttttggg ctagaaataa ttttgagctc gccaaggaga      3720
tataatgacg accaaccgca aggatgagca catcctctac gccctggagc agaagtcgtc      3780
gtacaactcg ttcgacgaag tggaactgat ccactcgtcg ctgccgctgt ataacctgga      3840
cgaaatcgac ctgtccaccg agttcgccgg ccgcaagtgg gatttcccgt tctacatcaa      3900
tgccatgacc ggcggtagca caagggccg cgaaatcaat cagaagctgg cccaggtcgc       3960
cgagtcgtgc ggcatcctgt tcgtcaccgg cagctactcc gccgcgctga agaacccgac      4020
cgacgactcg ttctcggtca agagcagcca cccgaatctg ctgctgggca cgaacatcgg      4080
cctcgacaag cccgtcgaac tgggcctgca gaccgtggaa gaaatgaacc ccgtgctgct      4140
ccaggtgcat gtgaacgtga tgcaagagct gctgatgccg gagggcgaac gcaagttccg      4200
cagctggcag tcgcacctgg ccgactactc gaagcagatc cccgtgccga tcgtgctgaa      4260
agaagtgggc ttcggcatgg acgccaagac catcgagcgt gcctacgagt cggcgtgcg      4320 caccgtggac ctctcgggcc gcggtggcac gagcttcgcg tacatcgaaa accgcgcag      4380 cggccagcgc gactacctga accagtgggg ccaatcgacc atgcaggccc tgctgaacgc      4440
gcaagaatgg aaggacaagg tcgagctgct ggtgtcgggc ggcgtgcgta acccgctcga      4500
catgatcaag tgcctggtgt tcggcgccaa ggccgtgggc ctgtcccgca ccgtgctgga      4560
gctggtcgaa acctacaccg tcgaagaagt catcggcatt gtccagggct ggaaggccga      4620
cctccgcctc atcatgtgct ccctgaactg cgccacgatc gcggacctcc agaaggtgga      4680
ctatctcctc tacggcaagc tcaaagaagc caaggaccag atgaagaagg cgtgacttta      4740
aggaaggagc gaagcatgcg ttgtagcgtt agcaccgaaa atgtgtcgtt tacgaaaacg      4800
gaaaccgaag ctcgccgcag cgcaaactat gaaccgaact cgtgggatta cgattacctc      4860
cttagcagcg atacgatga aagcattgaa gtgtataaag acaaagccaa gaaactggag      4920
gccgaagtcc gtcgcgaaat caacaatgag aaagcggagt tcttacgtt actggaattg      4980 atcgataacg tgcaacggtt aggcctcggc taccgctttg agagcgatat ccgtggtgca      5040
ctggaccgct tcgtatcgtc tggtggtttt gacgccgtta cgaaaacgag cctgcatggt      5100
acagcattgt cttttcggct gttgcgccag catggatttg aagtgtcaca ggaggcattt      5160
```

```
tcaggcttca aagaccagaa cgggaatttt ttggagaatt tgaaagaaga tatcaaagcg    5220
atcttatctc tgtatgaggc gtcatttctc gctctggaag gggaaaatat tctggacgaa    5280
gcgaaagtgt tcgcaatttc ccatctgaaa gaactttccg aagaaaagat tgggaaagaa    5340
ttggccgaac aggtgaacca tgcgctgaaa ctgccactgc accgtcgcac caacgcctc    5400 gaagcggtat ggtcgattga agcgtatcgc aaaaagagg atgcaaatca ggttctgctg    5460
gaactggcca ttctcgacta taacatgatt cagtccgtct atcaacgtga tctgcgcgaa    5520
actagtcgtt ggtggcgccg tgtaggactt gccactaaac tgcattttgc acgtgatcgt    5580
ctgattgagt cgttctattg ggcggttggt gtagcgtttg agccgcagta ttctgattgc    5640
cgcaatagtg tggcgaaaat gttctccttt gtgaccatca ttgacgatat ttacgacgtg    5700
tatggcaccc tggatgaact ggaattattc accgatgcag tagaacgctg ggacgtcaac    5760
gcgatcaatg atttgccgga ttacatgaaa ctgtgttttc tggccctgta taacaccatt    5820
aacgaaattg cctatgacaa cctcaaagac aagggtgaaa atatcctgcc ctatctgact    5880
aaagcttggg ctgatctgtg taacgcgttc ttacaggaag ccaaatggct ctacaacaag    5940
agtacgccta ctttcgatga ctactttggc aacgcttgga aaagctctag cggcccttta    6000
caactggtgt tcgcgtattt cgccgttgtt cagaatatca agaaagaaga gattgagaac    6060
ctccaaaagt accacgatac gatttcgcgt ccgtcacaca tctttcgcct ttgcaatgat    6120
ttggccagtg catctgcaga gattgcgcgc ggtgaaactg ccaactccgt cagttgctac    6180
atgcgtacca aaggcatcag cgaggaactg gctaccgagt cggtgatgaa cttaatcgat    6240
gaaacctgga agaagatgaa caaagagaaa cttggtggca gtctgtttgc taaaccgttc    6300
gttgagacag cgattaatct ggcgcgtcaa agccactgca cctaccacaa tggcgatgcc    6360
cacacatccc cagacgaatt aacccggaaa cgtgtcctga gtgtcatcac cgaacccatt    6420
ctgccgttcg aacgctaagc ctgctaacaa agcccgaaag gaagctgagt tggctgctgc    6480
caccgctgag ttggctgctg ccaccgctga gcactagtgc ggccgctttg cgcattcaca    6540
gttctccgca agaattgatt ggctccaatt cttggagtgg tgaatccgtt agcgaggtgc    6600
cgccggcttc cattcaggtc gaggtggccc ggctccatgc accgcgacgc aacgcgggga    6660
ggcagacaag gtatagggcg cgcctacaa tccatgccaa cccgttccat gtgctcgccg    6720
aggcggcata aatcgccgtg acgatcagcg gtccagtgat cgaagttagg ctggtaagag    6780
ccgcgagcga tccttgaagc tgtccctgat ggtcgtcatc tacctgcctg acagcatgg    6840 cctgcaacgc gggcatcccg atgccgccgg aagcgagaag aatcataatg gggaaggcca    6900
tccagcctcg cgtcgcgaac gccagcaaga cgtagcccag cgcgtcggcc gccatgccgg    6960
cgataatggc ctgcttctcg ccgaaacgtt tggtggcggg accagtgacg aaggcttgag    7020
cgagggcgtg caagattccg aataccgcaa gcgacaggcc gatcatcgtc gcgctccagc    7080
gaaagcggtc ctcgccgaaa atgacccaga gcgctgccgg cacctgtcct acgagttgca    7140
tgataaagaa gacagtcata agtgcggcga cgatagtcat gccccgcgcc caccggaagg    7200
agctgactgg gttgaaggct ctcaagggca tcggtcgacg ctctccctta tgcgactcct    7260
gcattaggaa gcagcccagt agtaggttga ggccgttgag caccgccgcc gcaaggaatg    7320
gtgcatgcaa ggagatggcg cccaacagtc ccccggccac ggggcctgcc accatacccc    7380
cgccgaaaca gcgctcatg agcccgaagt ggcgagcccg atcttcccca tcggtgatgt    7440
cggcgatata ggcgccagca accgcacctg tggcgccggt gatgccggcc acgatgcgtc    7500
```

-continued

| | |
|---|---|
| cggcgtagag gatccacagg acgggtgtgg tcgccatgat cgcgtagtcg atagtggctc | 7560 |
| caagtagcga agcgagcagg actgggcggc ggccaaagcg gtcggacagt gctccgagaa | 7620 |
| cgggtgcgca tagaaattgc atcaacgcat atagcgctag cagcacgcca tagtgactgg | 7680 |
| cgatgctgtc ggaatggacg atatcccgca agaggcccgg cagtaccggc ataaccaagc | 7740 |
| ctatgcctac agcatccagg gtgacggtgc cgaggatgac gatgagcgca ttgttagatt | 7800 |
| tcatacacgg tgcctgactg cgttagcaat ttaactgtga taaactaccg cattaaagct | 7860 |
| tatcgatgat aagctgtcaa acatgagaat tcttgaagac gaaagggcct cgtgatacgc | 7920 |
| ctattttat aggttaatgt catgataata atggtttctt agacgtcagg tggcactttt | 7980 |
| cggggaaatg tgcgcgcccg cgttcctgct ggcgctgggc ctgtttctgg cgctggactt | 8040 |
| cccgctgttc cgtcagcagc ttttcgccca cggccttgat gatcgcggcg gccttggcct | 8100 |
| gcatatcccg attcaacggc cccagggcgt ccagaacggg cttcaggcgc tcccgaaggt | 8160 |
| ctcgggccgt ctcttgggct tgatcggcct tcttgcgcat ctcacgcgct cctgcggcgg | 8220 |
| cctgtagggc aggctcatac ccctgccgaa ccgcttttgt cagccggtcg gccacggctt | 8280 |
| ccggcgtctc aacgcgcttt gagattccca gcttttcggc caatccctgc ggtgcatagg | 8340 |
| cgcgtggctc gaccgcttgc gggctgatgg tgacgtggcc cactggtggc cgctccaggg | 8400 |
| cctcgtagaa cgcctgaatg cgcgtgtgac gtgccttgct gcc | 8443 |

<210> SEQ ID NO 22
<211> LENGTH: 32
<212> TYPE: DNA
<213> ORGANISM: Artificial sequence
<220> FEATURE:
<223> OTHER INFORMATION: Synthetic

<400> SEQUENCE: 22

| | |
|---|---|
| ggaaggagcg aagcatgcgt tgtagcgtta gc | 32 |

<210> SEQ ID NO 23
<211> LENGTH: 38
<212> TYPE: DNA
<213> ORGANISM: Artificial sequence
<220> FEATURE:
<223> OTHER INFORMATION: Synthetic

<400> SEQUENCE: 23

| | |
|---|---|
| gggctttgtt agcaggctta gcgttcgaac ggcagaat | 38 |

<210> SEQ ID NO 24
<211> LENGTH: 21
<212> TYPE: DNA
<213> ORGANISM: Artificial sequence
<220> FEATURE:
<223> OTHER INFORMATION: Synthetic

<400> SEQUENCE: 24

| | |
|---|---|
| gcctgctaac aaagcccgaa a | 21 |

<210> SEQ ID NO 25
<211> LENGTH: 20
<212> TYPE: DNA
<213> ORGANISM: Artificial sequence
<220> FEATURE:
<223> OTHER INFORMATION: Synthetic

<400> SEQUENCE: 25

| | |
|---|---|
| gcttcgctcc ttccttaaag | 20 |

```
<210> SEQ ID NO 26
<211> LENGTH: 19
<212> TYPE: DNA
<213> ORGANISM: Artificial sequence
<220> FEATURE:
<223> OTHER INFORMATION: Synthetic

<400> SEQUENCE: 26
gccgccctat accttgtct                                                  19

<210> SEQ ID NO 27
<211> LENGTH: 20
<212> TYPE: DNA
<213> ORGANISM: Artificial sequence
<220> FEATURE:
<223> OTHER INFORMATION: Synthetic

<400> SEQUENCE: 27
acggcgtcac actttgctat                                                 20

<210> SEQ ID NO 28
<211> LENGTH: 20
<212> TYPE: DNA
<213> ORGANISM: Artificial sequence
<220> FEATURE:
<223> OTHER INFORMATION: Synthetic

<400> SEQUENCE: 28
cgcgtcgcga acgccagcaa                                                 20

<210> SEQ ID NO 29
<211> LENGTH: 20
<212> TYPE: DNA
<213> ORGANISM: Artificial sequence
<220> FEATURE:
<223> OTHER INFORMATION: Synthetic

<400> SEQUENCE: 29
acggggcctg ccaccatacc                                                 20

<210> SEQ ID NO 30
<211> LENGTH: 20
<212> TYPE: DNA
<213> ORGANISM: Artificial sequence
<220> FEATURE:
<223> OTHER INFORMATION: Synthetic

<400> SEQUENCE: 30
cttatcgatg ataagctgtc                                                 20

<210> SEQ ID NO 31
<211> LENGTH: 20
<212> TYPE: DNA
<213> ORGANISM: Artificial sequence
<220> FEATURE:
<223> OTHER INFORMATION: Synthetic

<400> SEQUENCE: 31
cagccctaga tcggccacag                                                 20

<210> SEQ ID NO 32
<211> LENGTH: 20
<212> TYPE: DNA
<213> ORGANISM: Artificial sequence
<220> FEATURE:
```

<223> OTHER INFORMATION: Synthetic

<400> SEQUENCE: 32
tgcctgcccc tcccttttgg                                              20

<210> SEQ ID NO 33
<211> LENGTH: 20
<212> TYPE: DNA
<213> ORGANISM: Artificial sequence
<220> FEATURE:
<223> OTHER INFORMATION: Synthetic

<400> SEQUENCE: 33
gcggcgagtg cggggggttcc                                             20

<210> SEQ ID NO 34
<211> LENGTH: 20
<212> TYPE: DNA
<213> ORGANISM: Artificial sequence
<220> FEATURE:
<223> OTHER INFORMATION: Synthetic

<400> SEQUENCE: 34
ggaaacccac ggcggcaatg                                              20

<210> SEQ ID NO 35
<211> LENGTH: 24
<212> TYPE: DNA
<213> ORGANISM: Artificial sequence
<220> FEATURE:
<223> OTHER INFORMATION: Synthetic

<400> SEQUENCE: 35
atcggctgta gccgcctcta gatt                                         24

<210> SEQ ID NO 36
<211> LENGTH: 20
<212> TYPE: DNA
<213> ORGANISM: Artificial sequence
<220> FEATURE:
<223> OTHER INFORMATION: Synthetic

<400> SEQUENCE: 36
agtaacaatt gctcaagcag                                              20

<210> SEQ ID NO 37
<211> LENGTH: 20
<212> TYPE: DNA
<213> ORGANISM: Artificial sequence
<220> FEATURE:
<223> OTHER INFORMATION: Synthetic

<400> SEQUENCE: 37
attcagagaa gaaaccaatt                                              20

<210> SEQ ID NO 38
<211> LENGTH: 43
<212> TYPE: DNA
<213> ORGANISM: Artificial sequence
<220> FEATURE:
<223> OTHER INFORMATION: Synthetic

<400> SEQUENCE: 38
gctagaaata attttgagct cgccaaggag atataatgca aac                    43

```
<210> SEQ ID NO 39
<211> LENGTH: 41
<212> TYPE: DNA
<213> ORGANISM: Artificial sequence
<220> FEATURE:
<223> OTHER INFORMATION: Synthetic

<400> SEQUENCE: 39
gcttcgctcc ttccttaaag ttatttaagc tgggtaaatg c                41

<210> SEQ ID NO 40
<211> LENGTH: 41
<212> TYPE: DNA
<213> ORGANISM: Artificial sequence
<220> FEATURE:
<223> OTHER INFORMATION: Synthetic

<400> SEQUENCE: 40
gctagaaata attttgagct cgccaaggag atataatggt c                41

<210> SEQ ID NO 41
<211> LENGTH: 38
<212> TYPE: DNA
<213> ORGANISM: Artificial sequence
<220> FEATURE:
<223> OTHER INFORMATION: Synthetic

<400> SEQUENCE: 41
gcttcgctcc ttccttaaag tcagcgcacc gaatacga                    38

<210> SEQ ID NO 42
<211> LENGTH: 55
<212> TYPE: DNA
<213> ORGANISM: Artificial sequence
<220> FEATURE:
<223> OTHER INFORMATION: Synthetic

<400> SEQUENCE: 42
gctagaaata attttgagct cgccaaggag atataatgac tgccgacaac aatag 55

<210> SEQ ID NO 43
<211> LENGTH: 43
<212> TYPE: DNA
<213> ORGANISM: Artificial sequence
<220> FEATURE:
<223> OTHER INFORMATION: Synthetic

<400> SEQUENCE: 43
gcttcgctcc ttccttaaag ttatagcatt ctatgaattt gcc              43

<210> SEQ ID NO 44
<211> LENGTH: 54
<212> TYPE: DNA
<213> ORGANISM: Artificial sequence
<220> FEATURE:
<223> OTHER INFORMATION: Synthetic

<400> SEQUENCE: 44
gctagaaata attttgagct cgccaaggag atataatgaa tcgaaaagat gaac  54

<210> SEQ ID NO 45
<211> LENGTH: 40
<212> TYPE: DNA
<213> ORGANISM: Artificial sequence
<220> FEATURE:
<223> OTHER INFORMATION: Synthetic
```

```
<400> SEQUENCE: 45
gcttcgctcc ttccttaaag ttaacgtttt gcgaaaacag                      40

<210> SEQ ID NO 46
<211> LENGTH: 57
<212> TYPE: DNA
<213> ORGANISM: Artificial sequence
<220> FEATURE:
<223> OTHER INFORMATION: Synthetic

<400> SEQUENCE: 46
gctagaaata attttgagct cgccaaggag atataatgac taaccgtaaa gatgatc   57

<210> SEQ ID NO 47
<211> LENGTH: 39
<212> TYPE: DNA
<213> ORGANISM: Artificial sequence
<220> FEATURE:
<223> OTHER INFORMATION: Synthetic

<400> SEQUENCE: 47
gcttcgctcc ttccttaaag ctaattgacc tgctgcaag                       39

<210> SEQ ID NO 48
<211> LENGTH: 57
<212> TYPE: DNA
<213> ORGANISM: Artificial sequence
<220> FEATURE:
<223> OTHER INFORMATION: Synthetic

<400> SEQUENCE: 48
gctagaaata attttgagct cgccaaggag atataatgac gaccaaccgc aaggatg   57

<210> SEQ ID NO 49
<211> LENGTH: 38
<212> TYPE: DNA
<213> ORGANISM: Artificial sequence
<220> FEATURE:
<223> OTHER INFORMATION: Synthetic

<400> SEQUENCE: 49
gcttcgctcc ttccttaaag tcacgccttc ttcatctg                        38

<210> SEQ ID NO 50
<211> LENGTH: 19
<212> TYPE: DNA
<213> ORGANISM: Artificial sequence
<220> FEATURE:
<223> OTHER INFORMATION: Synthetic

<400> SEQUENCE: 50
gccgccctat accttgtct                                             19

<210> SEQ ID NO 51
<211> LENGTH: 20
<212> TYPE: DNA
<213> ORGANISM: Artificial sequence
<220> FEATURE:
<223> OTHER INFORMATION: Synthetic

<400> SEQUENCE: 51
acggcgtcac actttgctat                                            20

<210> SEQ ID NO 52
<211> LENGTH: 1878
```

<212> TYPE: DNA
<213> ORGANISM: E. coli

<400> SEQUENCE: 52

```
ataggatcct aatacgactc actatagggt tttgtttaac tttaagaagg agatatacca      60
tggctactga actgctgtgt ttgcatcgcc cgatttcact tacacataaa ctgtttcgca     120
atccactgcc gaaggttatt caggcgaccc ctctgacgtt aaaactgcgt tgtagcgtta     180
gcaccgaaaa tgtgtcgttt acggaaacgg aaaccgaagc tcgccgcagc gcaaactatg     240
aaccgaactc gtgggattac gattacctcc ttagcagcga tacggatgaa agcattgaag     300
tgtataaaga caaagccaag aaactggagg ccgaagtccg tcgcgaaatc aacaatgaga     360
aagcggagtt tcttacgtta ctggaattga tcgataacgt gcaacggtta ggcctcggct     420
accgctttga gagcgatatc cgtggtgcac tggaccgctt cgtatcgtct ggtggttttg     480
acgccgttac gaaaacgagc ctgcatggta cagcattgtc ttttcggctg ttgcgccagc     540
atggatttga agtgtcacag gaggcatttt caggcttcaa agaccagaac gggaattttt     600
tggagaattt gaaagaagat atcaaagcga tcttatctct gtatgaggcg tcatttctcg     660
ctctggaagg ggaaaatatt ctggacgaag cgaaagtgtt cgcaatttcc catctgaaag     720
aactttccga agaaaagatt gggaaagaat tggccgaaca ggtgaaccat gcgctggaac     780
tgccactgca ccgtcgcacc caacgcctcg aagcggtatg gtcgattgaa gcgtatcgca     840
aaaaagagga tgcaaatcag gttctgctgg aactggccat tctcgactat aacatgattc     900
agtccgtcta tcaacgtgat ctgcgcgaaa ctagtcgttg gtggcgccgt gtaggacttg     960
ccactaaact gcattttgca cgtgatcgtc tgattgagtc gttctattgg gcggttggtg    1020
tagcgtttga gccgcagtat tctgattgcc gcaatagtgt ggcgaaaatg ttctcctttg    1080
tgaccatcat tgacgatatt tacgacgtgt atggcaccct ggatgaactg gaattattca    1140
ccgatgcagt agaacgctgg gacgtcaacg cgatcaatga tttgccggat tacatgaaac    1200
tgtgtttttct ggccctgtat aacaccatta acgaaattgc ctatgacaac ctcaaagaca    1260
agggtgaaaa tatcctgccc tatctgacta agcttgggc tgatctgtgt aacgcgttct    1320
tacaggaagc caaatggctc tacaacaaga gtacgcctac tttcgatgac tactttggca    1380
acgcttggaa aagctctagc ggcccttttac aactggtgtt cgcgtatttc gccgttgttc    1440
agaatatcaa gaaagaagag attgagaacc tccaaaagta ccacgatacg atttcgcgtc    1500
cgtcacacat ctttcgcctt tgcaatgatt tggccagtgc atctgcagag attgcgcgcg    1560
gtgaaactgc caactccgtc agttgctaca tgcgtaccaa aggcatcagc gaggaactgg    1620
ctaccgagtc ggtgatgaac ttaatcgatg aaacctggaa gaagatgaac aaagagaaac    1680
ttggtggcag tctgtttgct aaaccgttcg ttgagacagc gattaatctg gcgcgtcaaa    1740
gccactgcac ctaccacaat ggcgatgccc acacatcccc agacgaatta acccggaaac    1800
gtgtcctgag tgtcatcacc gaacccattc tgccgttcga acgccatcat caccatcacc    1860
attaatagcc tagggtgt                                                    1878
```

US 10,538,788 B2

METHODS, SYNTHETIC HOSTS AND REAGENTS FOR THE BIOSYNTHESIS OF DIENES AND DERIVATIVES THEREOF

This patent application claims the benefit of priority from U.S. Provisional Application Ser. No. 62/402,209, filed Sep. 30, 2016, teachings of which are hereby incorporated by reference in their entirety.

FIELD

The present invention relates to methods and compositions for synthesizing dienes and derivative thereof, such as isoprene, in *Cupriavidus necator*.

BACKGROUND

Isoprene is an important monomer for the production of specialty elastomers including motor mounts/fittings, surgical gloves, rubber bands, golf balls and shoes. Styrene-isoprene-styrene block copolymers form a key component of hot-melt pressure-sensitive adhesive formulations and cis-poly-isoprene is utilized in the manufacture of tires (Whited et al. Industrial Biotechnology 2010 6(3):152-163). Manufacturers of rubber goods depend on either imported natural rubber from the Brazilian rubber tree or petroleum-based synthetic rubber polymers (Whited et al. 2010, supra).

Given an over-reliance on petrochemical feedstocks, biotechnology offers an alternative approach to the generation of industrially relevant products, via biocatalysis. Biotechnology offers more sustainable methods for producing industrial intermediates, in particular isoprene.

There are known metabolic pathways leading to the synthesis of isoprene in eukaryotes such as *Populus alba* and some prokaryotes such as *Bacillis subtillis* have been reported to emit isoprene (Whited et al. 2010, supra). Isoprene production in prokaryotes is however rare, and no prokaryotic Isoprene synthase (hereafter ISPS) has been described to date.

Generally, two metabolic routes have been described incorporating the molecule dimethylallyl-pyrophosphate (—PP), the precursor to isoprene. These are known as the mevalonate and the non-mevalonate pathways (Kuzuyama Biosci. Biotechnol. Biochem. 2002 66(8):1619-1627), both of which function in terpenoid synthesis in vivo. Both require the introduction of a non-native ISPS in order to divert carbon to isoprene production.

The mevalonate pathway generally occurs in higher eukaryotes and Archaea and incorporates a decarboxylase enzyme, mevalonate diphosphate decarboxylase (hereafter MDD), that introduces the first vinyl-group into the precursors leading to isoprene. The second vinyl-group is introduced by isoprene synthase in the final step in synthesizing isoprene. The non-mevalonate pathway or 2-C-methyl-D-erythritol 4-phosphate (MEP) pathway occurs in many bacteria and dimethylallyl-PP is generated alongside isopentenyl-PP, two molecules which are interconvertible via the action of isopentenyl pyrophophate isomerase or isopentyl diphosphate isomerase (hereafter IDI).

SUMMARY

An aspect of the present invention relates to methods for synthesizing isoprene in *Cupriavidus necator*.

In one nonlimiting embodiment, the method comprises enzymatically converting isopentenyl-pyrophosphate to dimethylallylpyrophosphate using a polypeptide having isopentenyl diphosphate isomerase enzyme activity.

In one nonlimiting embodiment, the method comprises enzymatically converting dimethylallylpyrophosphate to isoprene using a polypeptide having isoprene synthase enzyme activity.

Another aspect of the present invention relates to methods for synthesizing isoprene in *Cupriavidus necator* which comprise enzymatically converting isopentenyl-pyrophosphate to dimethylallylpyrophosphate using a polypeptide having isopentenyl diphosphate isomerase enzyme activity; an enzymatically converting dimethylallylpyrophosphate to isoprene using a polypeptide having isoprene synthase enzyme activity.

Another aspect of the present invention relates to a substantially pure recombinant *Cupriavidus necator* hosts capable of producing isoprene via a methylerythritol phosphate (MEP) pathway.

Another aspect of the present invention relates to bio-derived isoprene produced in a recombinant *Cupriavidus necator* host.

Another aspect of the present invention relates to bio-derived, bio-based, or fermentation-derived products produced from any of the methods or hosts described herein.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and the drawings, and from the claims. The word "comprising" in the claims may be replaced by "consisting essentially of" or with "consisting of," according to standard practice in patent law.

BRIEF DESCRIPTION OF THE FIGURES

FIG. 1A compares isoprene production in *C. necator* strains transfected with vectors pBBR1-ISPS, pBBR1-EC IDI-ISPS, pBBR1-BS IDI-ISPS, pBBR1-SCIDI-ISPS, pBBR1-EFIDI-ISPS, pBBR1-SPyrIDI-ISPS. The *S. pneumonia* IDI construct is shown separately in FIG. 1B wherein it was tested with a different incubation volume and time alongside an *E. coli* IDI, accounting for the difference in isoprene yield.

DETAILED DESCRIPTION

*Cupriavidus necator* is a Gram-negative soil bacterium of the Betaproteobacteria class. This hydrogen-oxidizing bacterium is capable of growing at the interface of anaerobic and aerobic environments and easily adapts between heterotrophic and autotrophic lifestyles. Sources of energy for the bacterium include both organic compounds and hydrogen. *C. necator* does not naturally contain genes for isoprene synthase (ISPS) or isopentyl diphosphate isomerase (IDI) and therefore does not express these enzymes.

The present invention provides methods and compositions for synthesizing isoprene in *C. necator*. In the methods and compositions of the present invention, *C. necator* is used to synthesize isoprene via a methylerythritol phosphate (MEP) pathway.

Figure 1A:
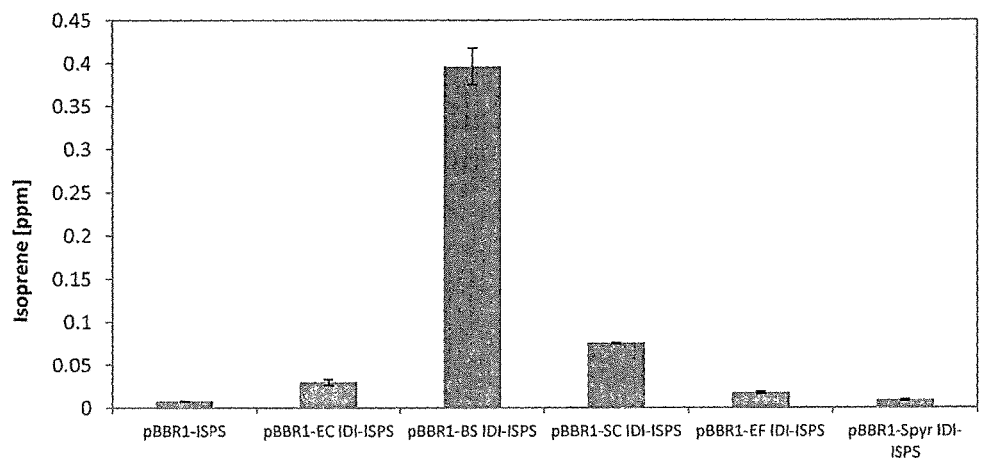
FIGS. 1A and 1B are bargraphs showing isoprene production (ppm) of IDI-ISPS expressing *C. necator* strains compared to a strain expressing ISPS alone.
Figure 1B:
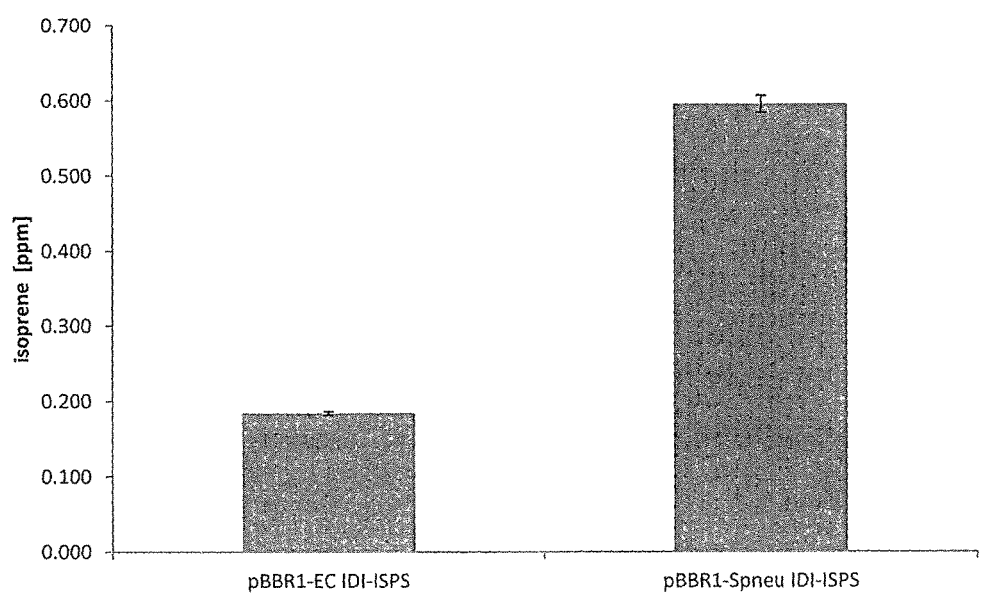
Figure 2A:
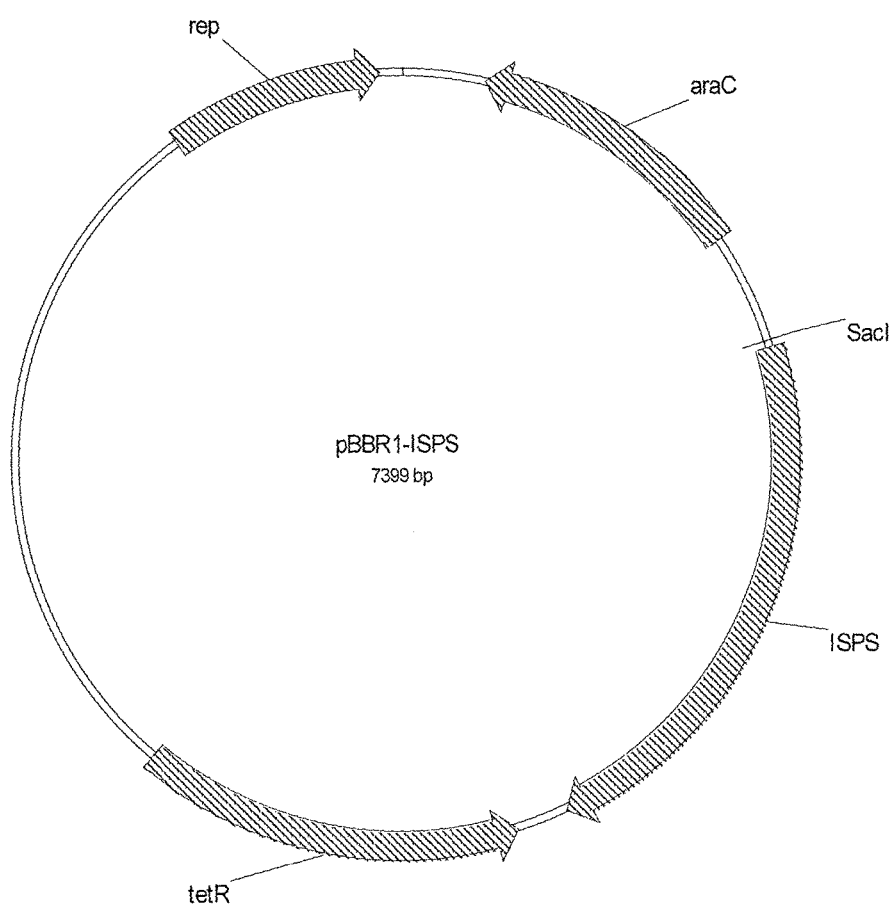
FIGS. 2A through 2G are images of vectors pBBR1-ISPS (FIG. 2A), pBBR1-EC IDI-ISPS (FIG. 2B), pBBR1-BS IDI-ISPS (FIG. 2C), pBBR1-SCIDI-ISPS (FIG. 2D), pBBR1-EFIDI-ISPS (FIG. 2E), pBBR1-SPyrIDI-ISPS (FIG. 2F) and pBBR1-Spneu IDI-ISPS (FIG. 2G). Nucleic acid sequences of these vectors are set forth herein in SEQ ID NOs: 15 through 21, respectively.
Figure 2B:
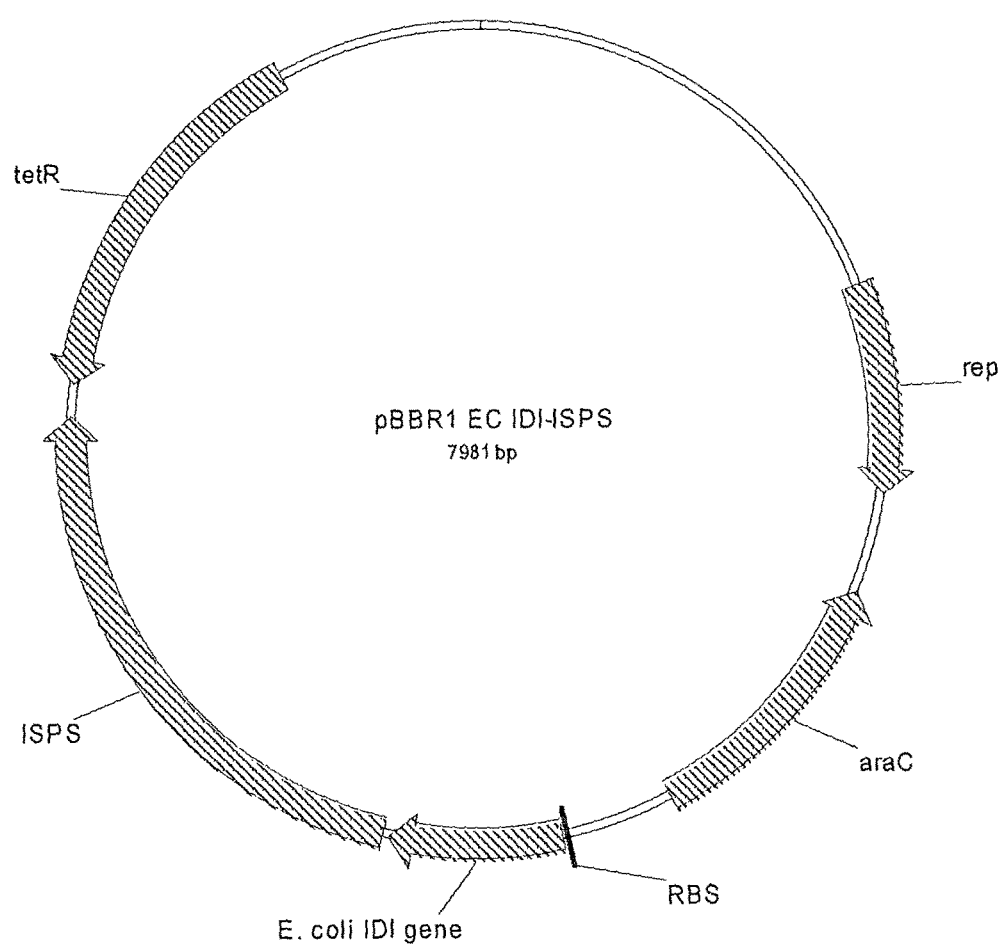
Figure 2C:
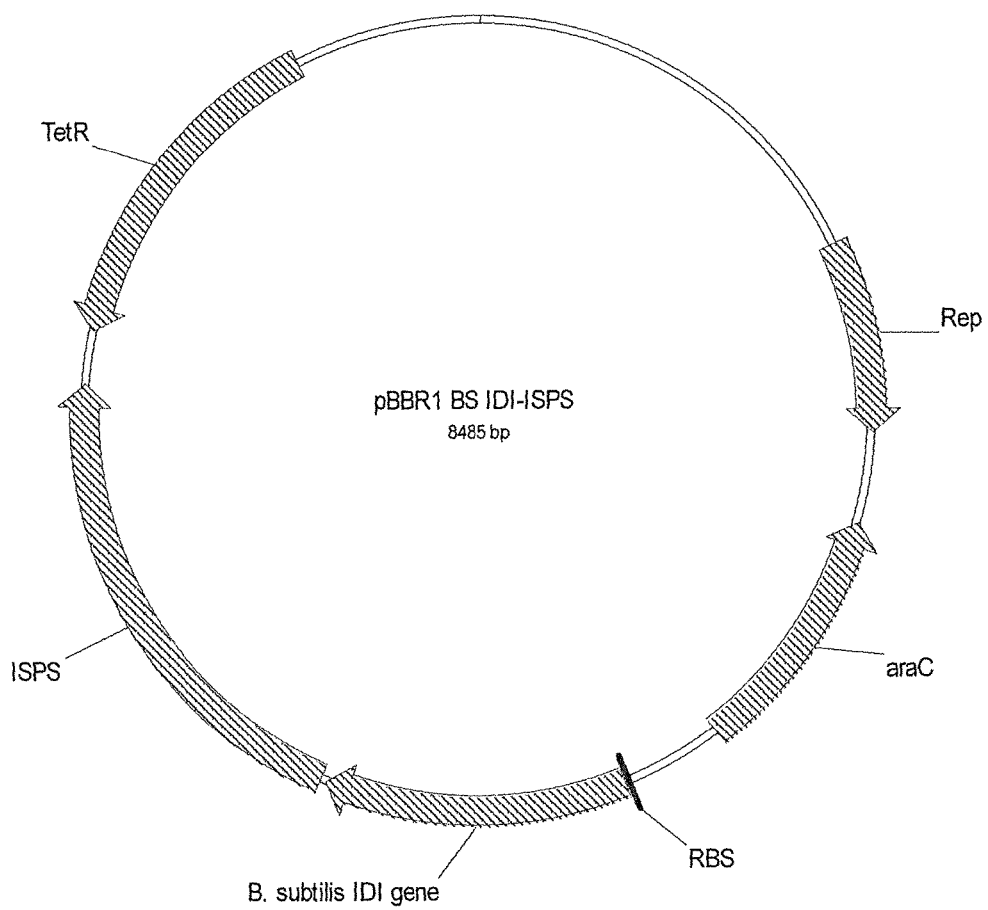
Figure 2D:
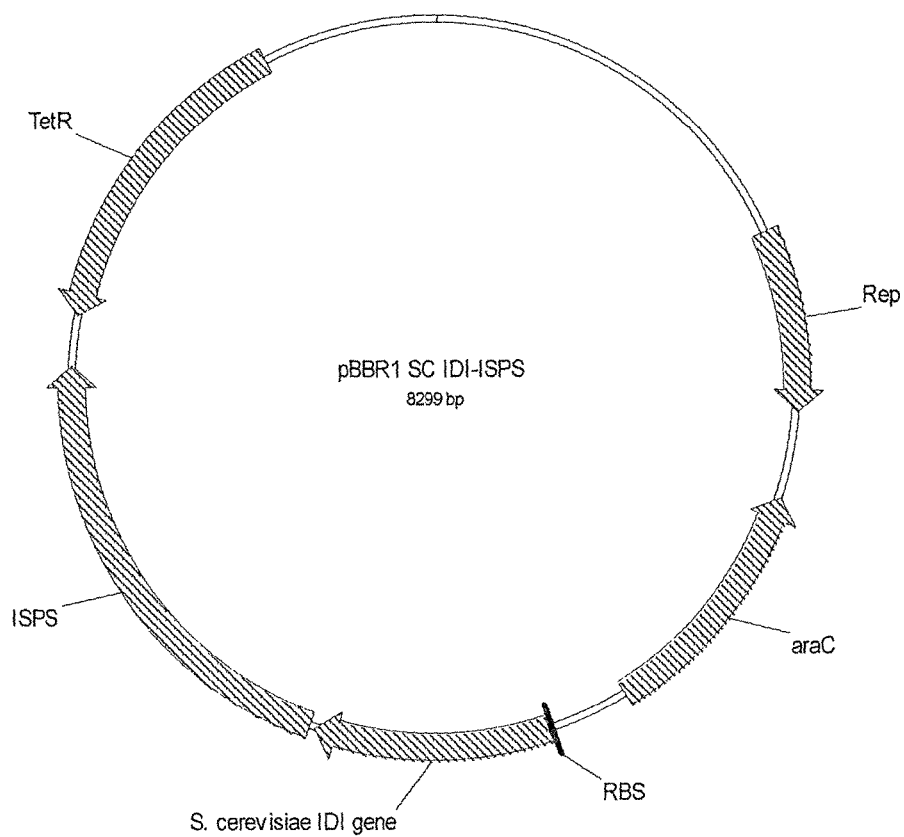
Figure 2E:
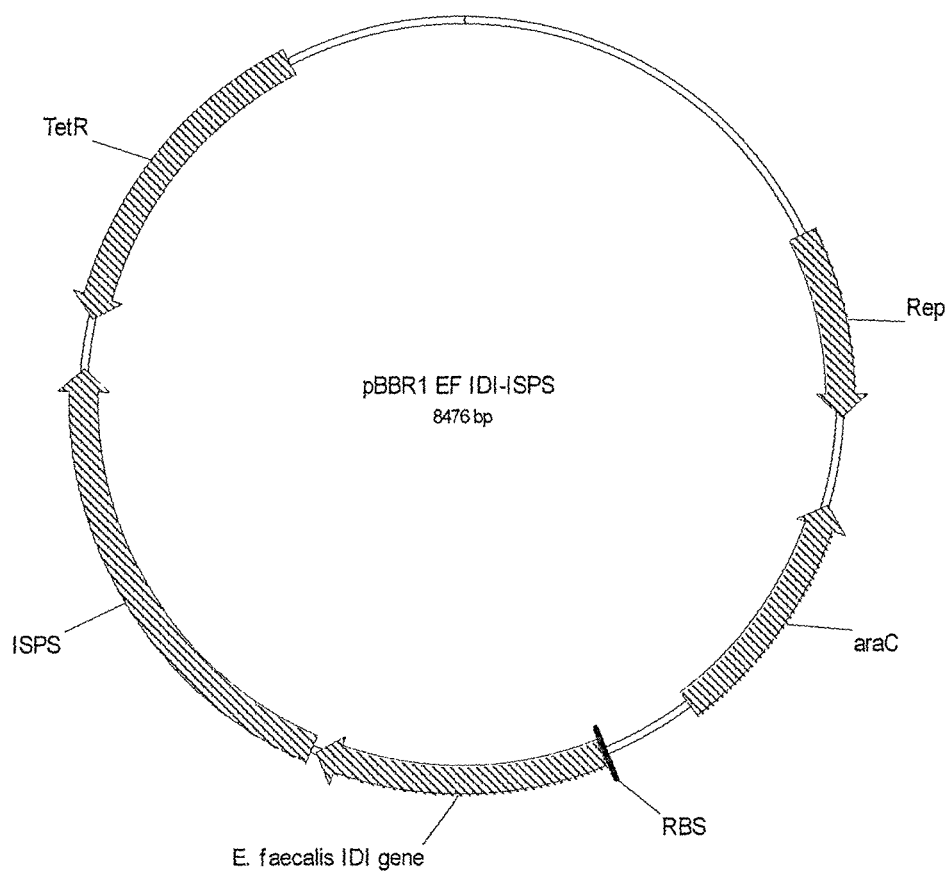
Figure 2F:
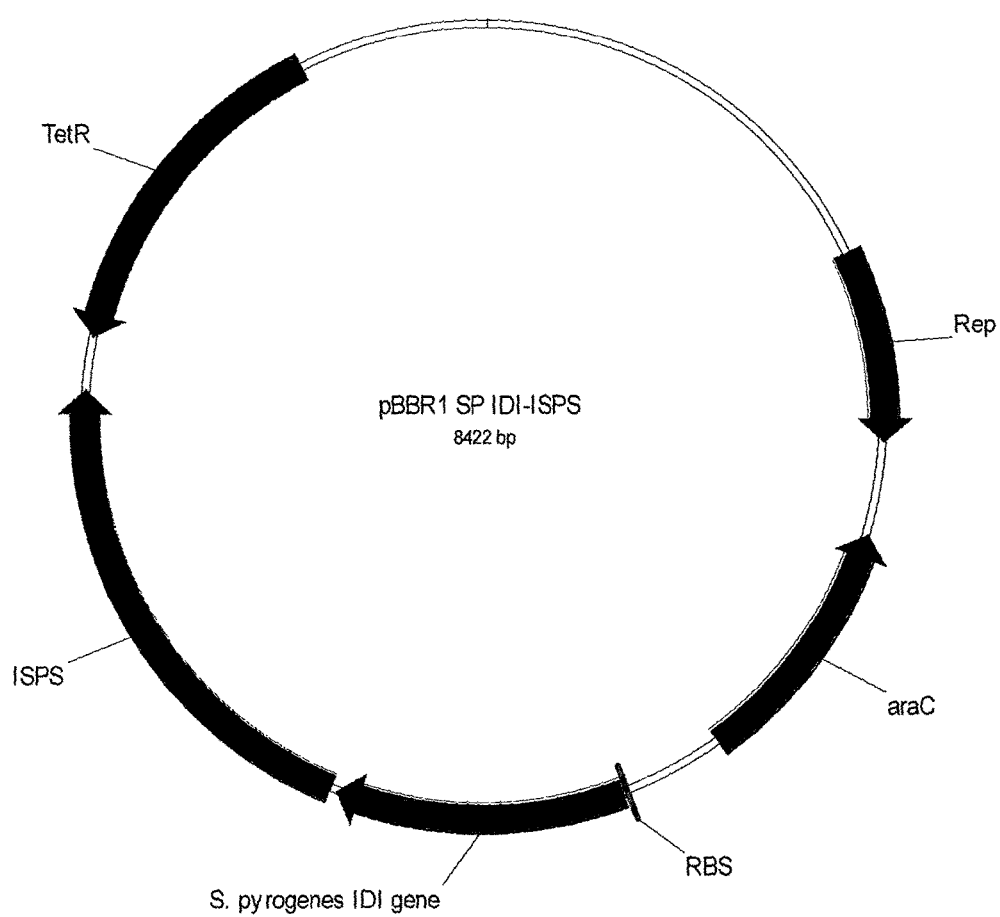
Figure 2G:
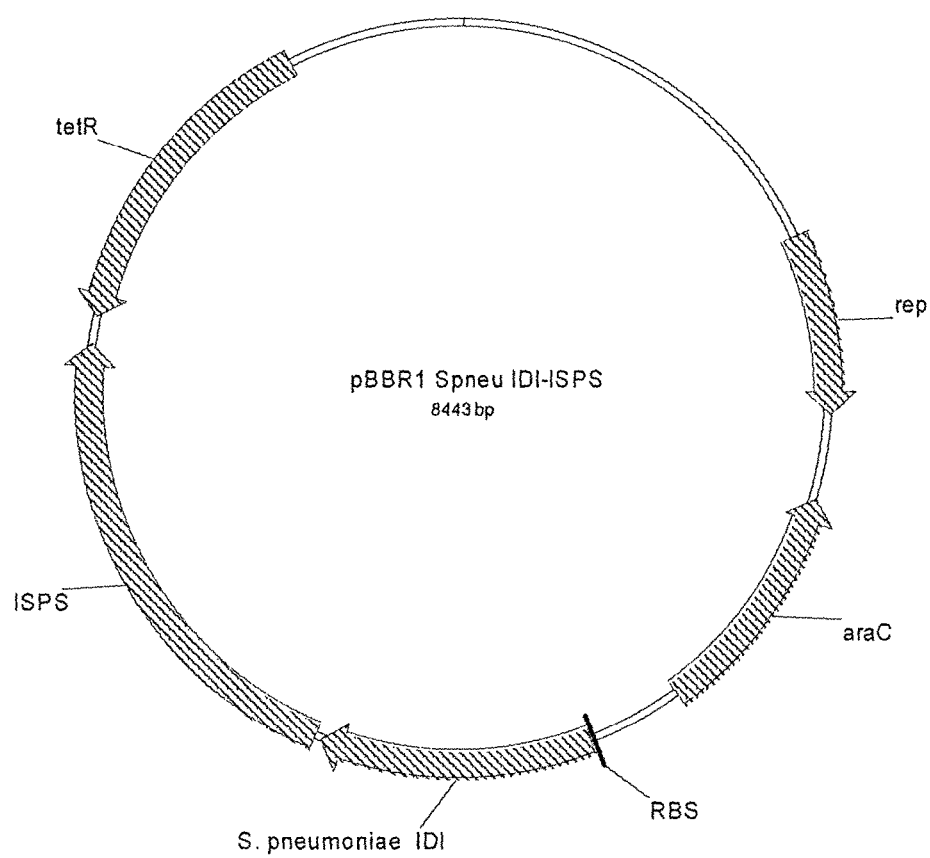

Surprisingly, the inventors herein have found that the overexpression of IDI and ISPS in *C. necator* resulted in the production of isoprene, via the MEP pathway. Various vectors were constructed and confirmed by sequencing. Vectors constructed included pBBR1-ISPS, pBBR1-EC IDI-ISPS, pBBR1-BS IDI-ISPS, pBBR1-SCIDI-ISPS, pBBR1EF-IDI-ISPS, pBBR1-SPyrIDI-ISPS and pBBR1-Spneu IDI-ISPS. Images of the constructed vectors are set forth in FIGS. 2A through 2G, respectively and their nucleic acid sequences are shown in SEQ ID NOs: 15 through 21, respectively. Isoprene production by strains of *C. necator* H16 ΔphaCAB transformed with these vectors is summarized in Table 3 and depicted graphically in FIGS. 1A and 1B. The construction of a bicistronic expression cassette comprising the *P. alba* isoprene synthase and an IDI was demonstrated to be sufficient to achieve isoprene production in *C. necator* H16ΔphaCAB. The IDIs from *E. coli, B. subtilis, S. cerevisiae* and *E. faecalis* were shown to be active in *C. necator* H16 across a greater than ten-fold range of yields (0.03 to 0.4 ppm). The strain containing the IDI from *B. subtilis* produced the most isoprene under these growth conditions, approximately 0.4 ppm. Other functional IDIs generated strains with a range of isoprene yields.

This document thus provides methods and compositions which can convert central precursors including isopentenyl-pyrophosphate and/or dimethylallylpyrophosphate into isoprene.

As used herein, the term "central precursor" is used to denote any metabolite in any metabolic pathway described herein leading to the synthesis of isoprene.

The term "central metabolite" is used herein to denote a metabolite that is produced in all microorganisms to support growth.

A nonlimiting example of a *C. necator* host useful in the present invention is a *C. necator* of the H16 strain. In one nonlimiting embodiment, a *C. necator* host of the H16 strain with the phaCAB gene locus knocked out (ΔphaCAB) is used.

In one nonlimiting embodiment, the method comprises enzymatically converting isopentenyl-pyrophosphate to dimethylallylpyrophosphate using a polypeptide having IDI enzyme activity.

Polypeptides having IDI enzyme activity and nucleic acids encoding IDIs have been identified from various organisms and are readily available in publicly available databases such as GenBank or EMBL. Examples include, but are in no way limited to, IDIs from *E. coli, B. subtilis, S. cerevisiae, E. faecalis, S. pyrogenes* and *S. pneumonia*. In one nonlimiting embodiment, the polypeptide having IDI enzyme activity has at least 70%, 75%, 80%, 85%, 90%, 91%, 92%, 93%, 94%, 95%, 96%, 97%, 98%, 99% or 99.5% sequence identity to an amino acid sequence set forth in any of SEQ ID NOs: 1, 2, 3, 4, 5 or 6 or a functional fragment thereof. In one nonlimiting embodiment, the polypeptide having IDI enzyme activity comprises the amino acid sequence set forth in any of SEQ ID NOs: 1, 2, 3, 4, 5 or 6 or a functional fragment thereof. In one nonlimiting embodiment, the polypeptide having IDI enzyme activity is encoded by a nucleic acid sequence having at least 70%, 75%, 80%, 85%, 90%, 91%, 92%, 93%, 94%, 95%, 96%, 97%, 98%, 99% or 99.5% sequence identity to the nucleic acid sequence set forth in any of SEQ ID NOs: 8, 9, 10, 11, 12 or 13 or a functional fragment thereof. In one nonlimiting embodiment, the polypeptide having IDI enzyme activity is encoded by a nucleic acid sequence comprising the nucleic acid sequence set forth in SEQ ID NOs. 8, 9, 10, 11, 12 or 13 or a functional fragment thereof.

In another nonlimiting embodiment, the method comprises enzymatically converting dimethylallylpyrophosphate to isoprene using a polypeptide having ISPS enzyme activity.

Polypeptides having ISPS enzyme activity and nucleic acids encoding ISPSs have been identified from various organisms and are readily available in publicly available databases such as GenBank or EMBL. A nonlimiting example is the ISPS of *Populus alba*. In one nonlimiting embodiment, the polypeptide having ISPS enzyme activity has at least 70%, 75%, 80%, 85%, 90%, 91%, 92%, 93%, 94%, 95%, 96%, 97%, 98%, 99% or 99.5% sequence identity to the amino acid sequence set forth in SEQ ID NO: 7 or a functional fragment thereof. In one nonlimiting embodiment, the polypeptide having ISPS enzyme activity comprises the amino acid sequence set forth in SEQ ID NO: 7 or a functional fragment thereof. In one nonlimiting embodiment, the polypeptide having ISPS enzyme activity is encoded by a nucleic acid sequence having at least 70%, 75%, 80%, 85%, 90%, 91%, 92%, 93%, 94%, 95%, 96%, 97%, 98%, 99% or 99.5% sequence identity to the nucleic acid sequence set forth in SEQ ID NO: 14 or a functional fragment thereof. In one nonlimiting embodiment, the polypeptide having ISPS enzyme activity is encoded by a nucleic acid sequence comprising the nucleic acid sequence set forth in SEQ ID NOs. 14 or a functional fragment thereof.

In one nonlimiting embodiment, the method for synthesizing isoprene in *Cupriavidus necator* comprises enzymatically converting isopentenyl-pyrophosphate to dimethylallylpyrophosphate using a polypeptide having IDI enzyme activity and enzymatically converting dimethylallylpyrophosphate to isoprene using a polypeptide having ISPS enzyme activity. In this embodiment, any of the polypeptides having IDI enzyme activity or ISPS enzyme activity described supra can be used.

The percent identity (homology) between two amino acid sequences can be determined as follows. First, the amino acid sequences are aligned using the BLAST 2 Sequences (B12seq) program from the stand-alone version of BLAST containing BLASTP version 2.0.14. This stand-alone version of BLAST can be obtained from the U.S. government's National Center for Biotechnology Information web site (www with the extension ncbi.nlm.nih.gov). Instructions explaining how to use the B12seq program can be found in the readme file accompanying BLASTZ. B12seq performs a comparison between two amino acid sequences using the BLASTP algorithm. To compare two amino acid sequences, the options of B12seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq-i c:\seq1.txt-j c:\seq2.txt-p blastp-o c:\output.txt. If the two compared sequences share homology (identity), then the designated output file will present those regions of homology as aligned sequences. If the two compared sequences do not share homology (identity), then the designated output file will not present aligned sequences. Similar procedures can be following for nucleic acid sequences except that blastn is used.

Once aligned, the number of matches is determined by counting the number of positions where an identical amino acid residue is presented in both sequences. The percent identity (homology) is determined by dividing the number of matches by the length of the full-length polypeptide amino acid sequence followed by multiplying the resulting value by 100. It is noted that the percent identity (homology) value is rounded to the nearest tenth. For example, 90.11, 90.12, 90.13, and 90.14 is rounded down to 90.1, while 90.15, 90.16, 90.17, 90.18, and 90.19 is rounded up to 90.2. It also is noted that the length value will always be an integer.

It will be appreciated that a number of nucleic acids can encode a polypeptide having a particular amino acid sequence. The degeneracy of the genetic code is well known to the art; i.e., for many amino acids, there is more than one nucleotide triplet that serves as the codon for the amino acid. For example, codons in the coding sequence for a given enzyme can be modified such that optimal expression in a particular species (e.g., bacteria or fungus) is obtained, using appropriate codon bias tables for that species.

Functional fragments of any of the polypeptides or nucleic acid sequences described herein can also be used in the methods of the document. The term "functional fragment" as used herein refers to a peptide fragment of a polypeptide or a nucleic acid sequence fragment encoding a peptide fragment of a polypeptide that has at least 25% (e.g., at least: 30%; 40%; 50%; 60%; 70%; 75%; 80%; 85%; 90%; 95%; 98%; 99%; 100%; or even greater than 100%) of the activity of the corresponding mature, full-length, polypeptide. The functional fragment can generally, but not always, be comprised of a continuous region of the polypeptide, wherein the region has functional activity.

In one nonlimiting embodiment, methods of the present invention are performed in a recombinant *Cupriavidus necator* host. Recombinant hosts can naturally express none or some (e.g., one or more, two or more) of the enzymes of the pathways described herein. Endogenous genes of the recombinant hosts also can be disrupted to prevent the formation of undesirable metabolites or prevent the loss of intermediates in the pathway through other enzymes acting on such intermediates. Recombinant hosts can be referred to as recombinant host cells, engineered cells, or engineered hosts. Thus, as described herein, recombinant hosts can include exogenous nucleic acids encoding one or more of IDIs and/or ISPSs, as described herein.

The term "exogenous" as used herein with reference to a nucleic acid (or a protein) and a host refers to a nucleic acid that does not occur in (and cannot be obtained from) a cell of that particular type as it is found in nature or a protein encoded by such a nucleic acid. Thus, a non-naturally-occurring nucleic acid is considered to be exogenous to a host once in the host. It is important to note that non-naturally-occurring nucleic acids can contain nucleic acid subsequences or fragments of nucleic acid sequences that are found in nature provided the nucleic acid as a whole does not exist in nature. For example, a nucleic acid molecule containing a genomic DNA sequence within an expression vector is non-naturally-occurring nucleic acid, and thus is exogenous to a host cell once introduced into the host, since that nucleic acid molecule as a whole (genomic DNA plus vector DNA) does not exist in nature. Thus, any vector, autonomously replicating plasmid, or virus (e.g., retrovirus, adenovirus, or herpes virus) that as a whole does not exist in nature is considered to be non-naturally-occurring nucleic acid. It follows that genomic DNA fragments produced by PCR or restriction endonuclease treatment as well as cDNAs are considered to be non-naturally-occurring nucleic acid since they exist as separate molecules not found in nature. It also follows that any nucleic acid containing a promoter sequence and polypeptide-encoding sequence (e.g., cDNA or genomic DNA) in an arrangement not found in nature is non-naturally-occurring nucleic acid. A nucleic acid that is naturally-occurring can be exogenous to a particular host microorganism. For example, an entire chromosome isolated from a cell of yeast x is an exogenous nucleic acid with respect to a cell of yeast y once that chromosome is introduced into a cell of yeast y.

In contrast, the term "endogenous" as used herein with reference to a nucleic acid (e.g., a gene) (or a protein) and a host refers to a nucleic acid (or protein) that does occur in (and can be obtained from) that particular host as it is found in nature. Moreover, a cell "endogenously expressing" a nucleic acid (or protein) expresses that nucleic acid (or protein) as does a host of the same particular type as it is found in nature. Moreover, a host "endogenously producing" or that "endogenously produces" a nucleic acid, protein, or other compound produces that nucleic acid, protein, or compound as does a host of the same particular type as it is found in nature.

In one nonlimiting embodiment of the present invention, the method for isoprene production is performed in a recombinant *Cupriavidus necator* host comprising an exogenous nucleic acid sequence encoding a polypeptide having IDI enzyme activity. In this embodiment, any of the nucleic acid sequences encoding a polypeptide having IDI enzyme activity as described supra can be used.

In another nonlimiting embodiment of the present invention, the method is performed using a recombinant *Cupriavidus necator* host comprising an exogenous nucleic acid encoding a polypeptide having ISPS enzyme activity. In this embodiment, any of the nucleic acid sequences encoding a polypeptide having ISPS enzyme activity as described supra can be used.

In another nonlimiting embodiment, the method is performed using a recombinant *Cupriavidus necator* host comprising an exogenous nucleic acid encoding a polypeptide having IDI enzyme activity and an exogenous nucleic acid encoding a polypeptide having ISPS enzyme activity. In this embodiment, any of the nucleic acid sequences encoding a polypeptide having IDI enzyme activity and any of the nucleic acid sequences having ISPS enzyme activity as described supra can be used.

In another nonlimiting embodiment, the method for isoprene production of the present invention is performed in a recombinant *Cupriavidus necator* host which has been transformed with a vector comprising any of SEQ ID NOs:15, 16, 17, 18, 19, 20 or 21.

In any the methods described herein, a fermentation strategy can be used that entails anaerobic, micro-aerobic or aerobic cultivation. A fermentation strategy can entail nutrient limitation such as nitrogen, phosphate or oxygen limitation. A cell retention strategy using a ceramic hollow fiber membrane can be employed to achieve and maintain a high cell density during fermentation. The principal carbon source fed to the fermentation can derive from a biological or non-biological feedstock. The biological feedstock can be, or can derive from, monosaccharides, disaccharides, lignocellulose, hemicellulose, cellulose, lignin, levulinic acid and formic acid, triglycerides, glycerol, fatty acids, agricultural waste, condensed distillers' solubles or municipal waste. The non-biological feedstock can be, or can derive from, natural gas, syngas, $CO_2/H_2$, methanol, ethanol, non-volatile residue (NVR) a caustic wash waste stream from cyclohexane oxidation processes or waste stream from a chemical or petrochemical industry.

In one nonlimiting embodiment, at least one of the enzymatic conversions of the isoprene production method comprises gas fermentation within the *Cupriavidus necator*. In this embodiment, the gas fermentation may comprise at least one of natural gas, syngas, $CO_2/H_2$, methanol, ethanol, non-volatile residue, caustic wash from cyclohexane oxidation processes, or waste stream from a chemical or petrochemical industry. In one nonlimiting embodiment, the gas fermentation comprises $CO_2/H_2$.

The methods of the present invention may further comprise recovering produced isoprene from the *Cupriavidus necator*.

Once produced, any method can be used to isolate isoprene. For example, isoprene can be recovered from the fermenter off-gas stream as a volatile product as the boiling point of isoprene is 34.1° C. At a typical fermentation temperature of approximately 30° C., isoprene has a high vapor pressure and can be stripped by the gas flow rate through the broth for recovery from the off-gas. Isoprene can be selectively adsorbed onto, for example, an adsorbent and separated from the other off-gas components. Membrane separation technology may also be employed to separate isoprene from the other off-gas compounds. Isoprene may desorbed from the adsorbent using, for example, nitrogen and condensed at low temperature and high pressure.

Compositions for synthesizing isoprene in *C. necator* are also provided by the present invention.

In one nonlimiting embodiment, a substantially pure recombinant *C. necator* host capable of producing isoprene via a methylerythritol phosphate (MEP) pathway is provided.

As used herein, a "substantially pure culture" of a recombinant host microorganism is a culture of that microorganism in which less than about 40% (i.e., less than about 35%; 30%; 25%; 20%; 15%; 100; 5%; 2%; 1%; 0.5%; 0.25%; 0.1%; 0.01%; 0.001%; 0.0001%; or even less) of the total number of viable cells in the culture are viable cells other than the recombinant microorganism, e.g., bacterial, fungal (including yeast), mycoplasmal, or protozoan cells. The term "about" in this context means that the relevant percentage can be 15% of the specified percentage above or below the specified percentage. Thus, for example, about 20% can be 17% to 23%. Such a culture of recombinant microorganisms includes the cells and a growth, storage, or transport medium. Media can be liquid, semi-solid (e.g., gelatinous media), or frozen. The culture includes the cells growing in the liquid or in/on the semi-solid medium or being stored or transported in a storage or transport medium, including a frozen storage or transport medium. The cultures are in a culture vessel or storage vessel or substrate (e.g., a culture dish, flask, or tube or a storage vial or tube).

In one nonlimiting embodiment, the recombinant *C. necator* host comprises an exogenous nucleic acid sequence encoding a polypeptide having IDI enzyme activity. Any nucleic acid sequence encoding a polypeptide having IDI enzyme activity as described supra can be used in this embodiment.

In another nonlimiting embodiment, the recombinant *C. necator* host comprises an exogenous nucleic acid encoding a polypeptide having IPSP enzyme activity. Any nucleic acid sequence encoding a polypeptide having IPSP enzyme activity as described supra can be used in this embodiment.

In another nonlimiting embodiment, the recombinant *C. necator* host comprises an exogenous nucleic acid encoding a polypeptide having IDI enzyme activity and an exogenous nucleic acid encoding a polypeptide having ISPS enzyme activity. Any of the nucleic acid sequences encoding a polypeptide having IDI enzyme activity or IPSP enzyme activity as described supra can be used.

In one nonlimiting embodiment, at least one of the exogenous nucleic acid sequences in the recombinant host is contained within a plasmid.

In one nonlimiting embodiment, at least one of the exogenous nucleic acid sequences is integrated into a chromosome of the host.

In one nonlimiting embodiment, the recombinant *C. necator* host has been transfected with a vector comprising any of SEQ ID NOs:15, 16, 17, 18, 19, 20 or 21.

Also provided by the present invention is isoprene bio-derived from a recombinant *C. necator* host according to any of methods described herein. In one nonlimiting embodiment, the bioderived isoprene has carbon isotope ratio that reflects an atmospheric carbon dioxide uptake source. Examples of such ratios include, but are not limited to, carbon-12, carbon-13, and carbon-14 isotopes.

In addition, the present invention provides bio-derived, bio-based, or fermentation-derived product produced using the methods and/or compositions disclosed herein. Examples of such products include, but are not limited to, compositions comprising at least one bio-derived, bio-based, or fermentation-derived compound or any combination thereof, as well as polymers, rubbers such as cis-polyisoprene rubber, trans-polyisoprene rubber, or liquid polyisoprene rubber, molded substances, formulations and semi-solid or non-semi-solid streams comprising one or more of the bio-derived, bio-based, or fermentation-derived compounds or compositions, combinations or products thereof.

The following section provides further illustration of the methods and compositions of the present invention. These working examples are illustrative only and are not intended to limit the scope of the invention in any way.

EXAMPLES

Example 1: Primers

Primers as listed in Table 1 were used in the following disclosed experiments.

| | Primer Sequence | |
|---|---|---|
| 1 | 5' GGAAGGAGCGAAGCATGCGTTGTAGCGTTAGC 3' | (SEQ ID NO: 22) |
| 2 | 5' GGGCTTTGTTAGCAGGCTTAGCGTTCGAACGGCAGAAT 3' | (SEQ ID NO: 23) |

-continued

| Primer | Sequence |
|---|---|
| 3 | 5' GCCTGCTAACAAAGCCCGAAA 3' (SEQ ID NO: 24) |
| 4 | 5' GCTTCGCTCCTTCCTTAAAG 3' (SEQ ID NO: 25) |
| 5 | 5' GCCGCCCTATACCTTGTCT 3' (SEQ ID NO: 26) |
| 6 | 5' ACGGCGTCACACTTTGCTAT 3' (SEQ ID NO: 27) |
| 7 | 5' CGCGTCGCGAACGCCAGCAA 3' (SEQ ID NO: 28) |
| 8 | 5' ACGGGGCCTGCCACCATACC 3' (SEQ ID NO: 29) |
| 9 | 5' CTTATCGATGATAAGCTGTC 3' (SEQ ID NO: 30) |
| 10 | 5' CAGCCCTAGATCGGCCACAG 3' (SEQ ID NO: 31) |
| 11 | 5' TGCCTGCCCCTCCCTTTTGG 3' (SEQ ID NO: 32) |
| 12 | 5' GCGGCGAGTGCGGGGGTTCC 3' (SEQ ID NO: 33) |
| 13 | 5' GGAAACCCACGGCGGCAATG 3' (SEQ ID NO: 34) |
| 14 | 5' ATCGGCTGTAGCCGCCTCTAGATT 3' (SEQ ID NO: 35) |
| 15 | 5' AGTAACAATTGCTCAAGCAG 3' (SEQ ID NO: 36) |
| 16 | 5' ATTCAGAGAAGAAACCAATT 3' (SEQ ID NO: 37) |
| 17 | 5' GCTAGAAATAATTTTGAGCTCGCCAAGGAGATATAATGCAAAC 3' (SEQ ID NO: 38) |
| 18 | 5' GCTTCGCTCCTTCCTTAAAGTTATTTAAGCTGGGTAAATGC 3' (SEQ ID NO: 39) |
| 19 | 5' GCTAGAAATAATTTTGAGCTCGCCAAGGAGATATAATGGTC 3' (SEQ ID NO: 40) |
| 20 | 5' GCTTCGCTCCTTCCTTAAAGTCAGCGCACCGAATACGA 3' (SEQ ID NO: 41) |
| 21 | 5' GCTAGAAATAATTTTGAGCTCGCCAAGGAGATATAATGACTGCCGACAACAATAG 3' (SEQ ID NO: 42) |
| 22 | 5' GCTTCGCTCCTTCCTTAAAGTTATAGCATTCTATGAATTTGCC 3' (SEQ ID NO: 43) |
| 23 | 5' GCTAGAAATAATTTTGAGCTCGCCAAGGAGATATAATGAATCGAAAAGATGAAC 3' (SEQ ID NO: 44) |
| 24 | 5' GCTTCGCTCCTTCCTTAAAGTTAACGTTTTGCGAAAACAG 3' (SEQ ID NO: 45) |
| 25 | 5' GCTAGAAATAATTTTGAGCTCGCCAAGGAGATATAATGACTAACCGTAAAGATGATC 3' (SEQ ID NO: 46) |
| 26 | 5' GCTTCGCTCCTTCCTTAAAGCTAATTGACCTGCTGCAAG 3' (SEQ ID NO: 47) |
| 27 | 5' GCTAGAAATAATTTTGAGCTCGCCAAGGAGATATAATGACGACCAACCGCAAGGATG 3' (SEQ ID NO: 48) |
| 28 | 5' GCTTCGCTCCTTCCTTAAAGTCACGCCTTCTTCATCTG 3' (SEQ ID NO: 49) |
| 29 | 5' GCCGCCCTATACCTTGTCT 3' (SEQ ID NO: 50) |
| 30 | 5' ACGGCGTCACACTTTGCTAT 3' (SEQ ID NO: 51) |

Example 2: Cloning of Poplar ISPS for Expression in *C. necator* spp.

The protein sequence for the *Populus alba* was obtained from GenBank (BAD98243.1) and the full gene (with an additional promoter and terminator), codon optimized for *E. coli* was purchased from Eurofins MWG (SEQ ID NO:52). This DNA was used as a template for amplification of the gene using primers 1 and 2 (see Table 1) and Phusion polymerase (NEB) with an annealing temperature of 45° C. (the open reading frame (ORF) generated lacked the native plasmid tag; this ORF corresponds to nucleotides 168-1865 of SEQ ID NO:52). The vector backbone of pBBR1MCS3-pBAD was generated with primer 3 and 4 (see Table 1) and with Merck Millipore KOD polymerase with annealing temperatures of 50-55° C. The two fragments were ligated using NEB Gibson Assembly reaction master mix as per the manufacturer's recommended protocol. The ligation mix was transformed into chemically competent *E. coli* NEB5α and correct clones verified via a combination of colony PCR and sequencing with primers 5 and 6 (see Table 1). Subsequently the whole construct was sequenced by MWG-Eurofins using primers 7-16 (see Table 1). A single verified construct was taken forward for further work and designated pBBR1-ISPS (see FIG. 2A; SEQ ID NO:15)

Example 3: Cloning of IDI-ISPS Bicistrons for Expression in C. necator spp.

A unique SacI restriction site was identified in pBBR1-ISPS, upstream of the ribosome binding site and downstream of the predicted transcriptional start site. pBBR1-ISPS was purified from NEB5a alpha using the Qiagen plasmid Midi prep kit, cut with SacI (NEB) and purified using the Qiagen PCR purification kit as per the recommended protocol. Nucleic acid sequences for IDIs from *E. coli* (SEQ ID NO:8), *B. subtilis* (SEQ ID NO:9), *S. cerevisiae* (SEQ ID NO:10), *E. faecalis* (SEQ ID NO:11), *S. pyrogenes* (SEQ ID NO:12) and *S. pneumonia* (SEQ ID NO:13) were obtained from GenBank. Each IDI was amplified from genomic DNA (purchased directly from DSMZ or ATCC) or in the case of the *B. subtilis* and *S. pneumonia* variants, from a codon optimized (*C. necator*) synthetic operon purchased from Eurofins MWG.

PCR products were generated with Merck Millipore KOD polymerase and an annealing temperature of 55° C. and using primers 17-28 (see Table 1) purified using the Qiagen PCR purification kit and the recommended protocol. The PCR products were then used in a Gibson assembly with the SacI digested and purified pBBR1-ISPS and individual ligations transformed to *E. coli* NEB5a. Clones were verified via a combination of colony PCR with Taq polymerase (NEB) and sequencing with primers 29 and 30 (see Table 1). Single verified constructs representing each IDI coupled to ISPS were designated pBBR-EC IDI-ISPS (FIG. 2B; SEQ ID NO:16), pBBR1-BS IDI-ISPS (FIG. 2C; SEQ ID NO:17), pBBR1-SCIDI-ISPS (FIG. 2D; SEQ ID NO:18), pBBR1-EFIDI-ISPS (FIG. 2E; SEQ ID NO:19), pBBR1-SPyrIDI-ISPS (FIG. 2F; SEQ ID NO:20) and pBBR1 SpneuIDI-ISPS (FIG. 2G; SEQ ID NO:21) and further examined.

Example 4: Vector Preparation and Transference to C. necator H16 AphaCAB

Vectors pBBR-EC IDI-ISPS, pBBR1-BS IDI-ISPS, pBBR1-SCIDI-ISPS, pBBR1-EFIDI-ISPS, pBBR1-SPyrIDI-ISPS and pBBR1 SpneuIDI-ISPS were prepared from their respective NEB5α hosts using the Qiagen Midi prep kit and appropriate culture volumes. A *C. necator* H16 strain with the phaCAB gene locus knocked out (AphaCAB) was grown to mid/late exponential phase in tryptic soy broth (TSB) media at 30° C. Cells were made competent with glycerol washes and used immediately. Unexpectedly, competent cells were transformed with at least 1 μg of vector DNA via electroporation and recovered in TSB medium. Transformants were identified on TSB agar with 10 μg/ml tetracycline. Single transformants representative of each IDI-ISPS clone were further examined.

Example 5: Isoprene Production in C. necator H16 AphaCAB

IDI-ISPS clones in *C. necator* H16 AphaCAB, representative of each IDI under study, were grown over 48 hours on TSB agar (without dextrose). The *P. alba* ISPS construct (pBBR1-ISPS) containing strain was also grown on the same media, as a control. Cultures were grown, induced and harvested. Cell pellets were resuspended in a suitable media and normalized in solution based on the wet cell weight. Further incubations with induction were performed in screw cap headspace gas chromatography (GC) vials (Anatune 093640-040-00 and 093640-038-00). Surprisingly, isoprene was produced and could be measured via gas chromatography-mass spectrometry (GCMS), the parameters for which are set out in Table 2. Ions monitored for isoprene were 39, 53 and 67 on an Agilent DB-624 column Agilent.

TABLE 2

GCMS analysis conditions for Isoprene
GCMS CONDITIONS

| PARAMETER | VALUE | |
|---|---|---|
| Carrier Gas | Helium at constant flow (2.0 ml/min) | |
| Injector | Split ratio | Split 10:L |
| | Temperature | 150° C. |
| Detector | Source Temperature | 230° C. |
| | Quad Temperature | 150° C. |
| | Interface | 260° C. |
| | Gain | 1 |
| | Scan Range] | m/z 30-200 |
| | Threshold | 150 |
| | Scan Speed 2^2(A/D samples) | 4 |
| | Sampling Rate 2^n = 2^2 | |
| | Mode | SCAN and SIM |
| Solvent delay * | 2.80 min | |
| Oven Temperature | Initial T: 40° C. × 10 min | |
| Oven Ramp | 40° C./min to 260° C. for 5 min | |
| Injection volume | 50 μl from the HS in the GC 2 ml vial | |
| Incubation time and T | 15 min at 95° C. | |
| Agitator | ON 500 rpm | |
| Injection volume | 500 μl of the Head Space | |
| Gas saver | On after 2 min | |
| Concentration range (μg/ml) | 0.1-5.0 | |
| GC Column | DB-624 (122-1334 Agilent) 60 m × 250 μm × 1.4 μm | |

Results of these isoprene production studies are shown in Table 3 and depicted graphically in FIG. 1.

TABLE 3

Isoprene production results of IDI-ISPS expressing *C. necator* strains

| Culture *C. necator* H16 ΔphaCAB | Mean isoprene ppm | Standard deviation |
|---|---|---|
| pBBR1-ISPS | 0.0078 | 0.000051 |
| pBBR1 - EC IDI-ISPS | 0.030 | 0.0032 |
| pBBR1 - BS IDI-ISPS | 0.40 | 0.021 |
| pBBR1 - SC-IDI-ISPS | 0.076 | 0.0005 |
| pBBR1 - EF IDI-ISPS | 0.018 | 0.0012 |
| pBBR1 - SPyr IDI-ISPS | 0.0089 | 0.00089 |
| pBBR1 - EC IDI-ISPS | 0.184 | 0.003 |
| pBBR1 - Spneu IDI-ISPS | 0.595 | 0.011 |

What is claimed is:

1. A method for synthesizing isoprene or derivatives thereof in *Cupriavidus necator*, said method comprising: enzymatically converting isopentenyl-pyrophosphate to dimethylallylpyrophosphate using a polypeptide having isopentenyl diphosphate isomerase enzyme activity, wherein the polypeptide having isopentenyl diphosphate isomerase enzyme activity is capable of converting isopentenyl-pyrophosphate to dimethylallylpyrophosphate and has at least 90% sequence identity to an amino acid sequence set forth in SEQ ID NO:2 or is encoded by a nucleic acid sequence having at least 90% sequence identity to the nucleic acid sequence set forth in SEQ ID NO:9; and enzymatically converting dimethylallylpyrophosphate to isoprene or derivatives thereof using a polypeptide having isoprene synthase enzyme activity, wherein the polypeptide having isoprene synthase enzyme activity is capable of converting dimethylallylpyrophosphate to isoprene and has at least 90% sequence identity to the amino acid sequence set forth in SEQ ID NO: 7 or is encoded by a nucleic acid sequence having at least 90% sequence identity to the nucleic acid sequence set forth in SEQ ID NO: 14.

2. The method of claim 1 wherein the polypeptide having isopentenyl diphosphate isomerase enzyme activity comprises the amino acid sequence set forth in SEQ ID NO:2 or is encoded by a nucleic acid sequence comprising the nucleic acid sequence set forth in SEQ ID NO:9.

3. The method of claim 1 wherein the polypeptide having isoprene synthase enzyme activity comprises the amino acid sequence set forth in SEQ ID NO: 7;

or is encoded by a nucleic acid sequence comprising the nucleic acid sequence set forth in SEQ ID NO: 14.

4. The method of claim 1, wherein said method is performed in a recombinant *Cupriavidus necator* host.

5. The method of claim 4 wherein the recombinant *Cupriavidus necator* host has been transfected with a vector comprising SEQ ID NO:16.

6. The method of claim 1, wherein at least one of the enzymatic conversions comprises gas fermentation within the *Cupriavidus necator*.

7. The method of claim 6, wherein the gas fermentation comprises at least one of natural gas, syngas, $CO_2/H_2$, methanol, ethanol, non-volatile residue, caustic wash from cyclohexane oxidation processes, or waste stream from a chemical or petrochemical industry.

8. The method of claim 7 wherein the gas fermentation comprises $CO_2/H_2$.

9. The method of claim 1, further comprising recovering produced isoprene.

* * * * *